(12) United States Patent
Jang et al.

(10) Patent No.: US 11,524,947 B2
(45) Date of Patent: Dec. 13, 2022

(54) ORGANIC COMPOUND, LIGHT EMITTING DIODE AND LIGHT EMITTING DEVICE HAVING THE COMPOUND

(71) Applicant: LG Display Co., Ltd., Seoul (KR)

(72) Inventors: So-Young Jang, Paju-si (KR); Hee-Jun Park, Paju-si (KR); Jeong-Dae Seo, Paju-si (KR); Seon-Keun Yoo, Paju-si (KR); Ji-Cheol Shin, Paju-si (KR); Sang-Beom Kim, Paju-si (KR)

(73) Assignee: LG DISPLAY CO., LTD., Seoul (KR)

( * ) Notice: Subject to any disclaimer, the term of this patent is extended or adjusted under 35 U.S.C. 154(b) by 383 days.

(21) Appl. No.: 16/719,467

(22) Filed: Dec. 18, 2019

(65) Prior Publication Data
US 2020/0199090 A1 Jun. 25, 2020

(30) Foreign Application Priority Data
Dec. 21, 2018 (KR) .................. 10-2018-0167004

(51) Int. Cl.
*H01L 51/00* (2006.01)
*C07D 307/91* (2006.01)
(Continued)

(52) U.S. Cl.
CPC ......... *C07D 307/91* (2013.01); *C07D 333/76* (2013.01); *C07D 407/12* (2013.01);
(Continued)

(58) Field of Classification Search
None
See application file for complete search history.

(56) References Cited

U.S. PATENT DOCUMENTS

2005/0067951 A1* 3/2005 Richter .................. C07F 7/081
313/504
2009/0227812 A1 9/2009 Kubo et al.
(Continued)

FOREIGN PATENT DOCUMENTS

JP 2004-59557 A 2/2004

OTHER PUBLICATIONS

Liu et al., "Tetraphenylmethane-Arylamine Hole-Transporting Materials for Perovskite Solar Cells", ChemSusChem, Feb. 10, 2017, pp. 968-975, Wiley Online Library, www.chemsuschem.org.
(Continued)

*Primary Examiner* — Robert S Loewe
(74) *Attorney, Agent, or Firm* — Birch, Stewart, Kolasch & Birch, LLP

(57) ABSTRACT

An organic compound having a tetraphenyl moiety and at least one fused hetero aryl moiety having at least one oxygen and/or sulfur on a ring and bonded to the tetraphenyl moiety directly or indirectly, and a light emitting diode and a light emitting device having the organic compound are disclosed. The organic compound has excellent thermal resistance property and hole mobility property. The organic compound can be incorporated into a hole transfer layer, an electron blocking layer and/or a charge generation layer of the light emitting diode. Therefore, the light emitting diode and light emitting device according to the present invention have decreased driving voltage and enhanced luminous efficiency.

33 Claims, 4 Drawing Sheets

(51) Int. Cl.
*C07D 333/76* (2006.01)
*C07D 407/12* (2006.01)
*C07D 409/12* (2006.01)
*H01L 51/50* (2006.01)

(52) U.S. Cl.
CPC ........ C07D 409/12 (2013.01); H01L 51/0061 (2013.01); H01L 51/0072 (2013.01); H01L 51/0074 (2013.01); H01L 51/5056 (2013.01)

(56) References Cited

U.S. PATENT DOCUMENTS

| | | | | |
|---|---|---|---|---|
| 2009/0256468 | A1* | 10/2009 | Kim | C07D 237/20 313/504 |
| 2012/0248426 | A1* | 10/2012 | Kato | C07D 307/91 257/40 |
| 2015/0243904 | A1* | 8/2015 | Lin | H01L 51/0074 257/40 |
| 2021/0061794 | A1* | 3/2021 | Jo | H01L 51/0061 |

OTHER PUBLICATIONS

Vivo et al., "Hole-Transporting Materials for Printable Perovskite Solar Cells", Materials, 2017, vol. 10, 1087, Sep. 15, 2017, 45 pages, www.mdpi.com/journal/materials.

* cited by examiner

ORGANIC COMPOUND, LIGHT EMITTING DIODE AND LIGHT EMITTING DEVICE HAVING THE COMPOUND

CROSS-REFERENCE TO RELATED APPLICATIONS

This application claims the benefit under 35 U.S.C. § 119(a) of Korean Patent Application No. 10-2018-0167004, filed in the Republic of Korea on Dec. 21, 2018, which is incorporated herein by reference in its entirety.

BACKGROUND

Technical Field

The present disclosure relates to an organic compound, and more specifically, to an organic compound enhancing luminous efficiency and color purity, an organic light emitting diode and an organic light emitting device including the compound.

Description of the Related Art

As a display device has become larger, there exists a need for a flat display device with lower spacing occupation. Among the flat display devices, a display device using an organic light emitting diode (OLED) has come into the spotlight.

In the OLED, when electrical charges are injected into an emission layer between an electron injection electrode (i.e., cathode) and a hole injection electrode (i.e., anode), electrical charges are combined to be paired, and then emit light as the combined electrical charges are disappeared.

The OLED can be formed even on a flexible transparent substrate such as a plastic substrate. In addition, the OLED can be driven at a lower voltage of 10 V or less. Moreover, the OLED has relatively lower power consumption for driving compared to plasma display panel and inorganic electroluminescent devices, and color purity thereof is very high. Further, since the OLED can display various colors such as green, blue, red and the like, the OLED display device has attracted a lot of attention as a next-generation display device that can replace a liquid crystal display device (LCD).

High driving voltage and current density in the OLED may adversely affect the stability of the materials and the lifetime of the diode because of enormous stress applied to the materials in the diode. Therefore, much researches and studies have been made on the material capable of increasing a luminous efficiency of the OLED and lowering power consumption by adjusting energy levels of a charge transfer layer in the OLED.

BRIEF SUMMARY

Accordingly, the present disclosure is directed to an organic compound, a light emitting diode and a light emitting device including the organic compounds that substantially obviate one or more of the problems due to the limitations and disadvantages of the related art.

An object of the present disclosure is to provide an organic compound having excellent charge transportation capability and thermal stability, and a light emitting diode and a light emitting device capable of driving at lower voltages and having improved luminous efficiency and luminous lifetime by introducing the organic compound.

Additional features and advantages of the disclosure will be set forth in the description which follows, and in part will be apparent from the description, or may be learned by practice of the disclosure. The objectives and other advantages of the disclosure will be realized and attained by the structure particularly pointed out in the written description and claims hereof as well as the appended drawings.

According to an aspect, the present disclosure provides an organic compound having the following structure of Chemical Formula 1:

Chemical Formula 1

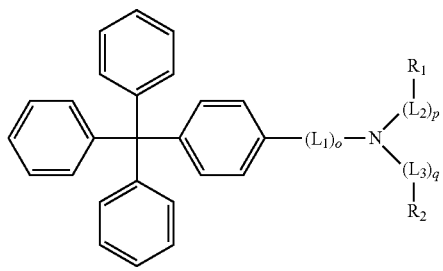

wherein each of $R_1$ and $R_2$ an independently is unsubstituted or substituted $C_5$~$C_{30}$ aryl group or an unsubstituted or substituted $C_4$~$C_{30}$ hetero aryl group, wherein at least one of $R_1$ and $R_2$ is an unsubstituted or substituted $C_{10}$~$C_{30}$ hetero aryl group, which has at least one of oxygen (O) and sulfur (S) in a ring; each of $L_1$, $L_2$, and $L_3$ is independently is an unsubstituted or substituted $C_5$~$C_{30}$ arylene group or an unsubstituted or substituted $C_4$~$C_{30}$ hetero arylene group; and each of o, p and q is independently an integer of 0 to 2.

According to another aspect, the present disclosure provides a light emitting diode that comprises the organic compound in a hole transfer layer.

According to still another aspect, the present disclosure provides a light emitting diode that comprises the organic compound in an electron blocking layer.

According to still another aspect, the present disclosure provides a light emitting diode that comprises the organic compound in a P-type charge generation layer.

According to still another aspect, the present disclosure provides a light emitting device that comprises a substrate and the light emitting diode over the substrate, as described above.

It is to be understood that both the foregoing general description and the following detailed description are examples and are explanatory and are intended to provide further explanation of the disclosure as claimed.

BRIEF DESCRIPTION OF THE DRAWINGS

The accompanying drawings, which are included to provide a further understanding of the disclosure, are incorporated in and constitute a part of this specification, illustrate implementations of the disclosure and together with the description serve to explain the principles of embodiments of the disclosure.

DETAILED DESCRIPTION

Figure 1:
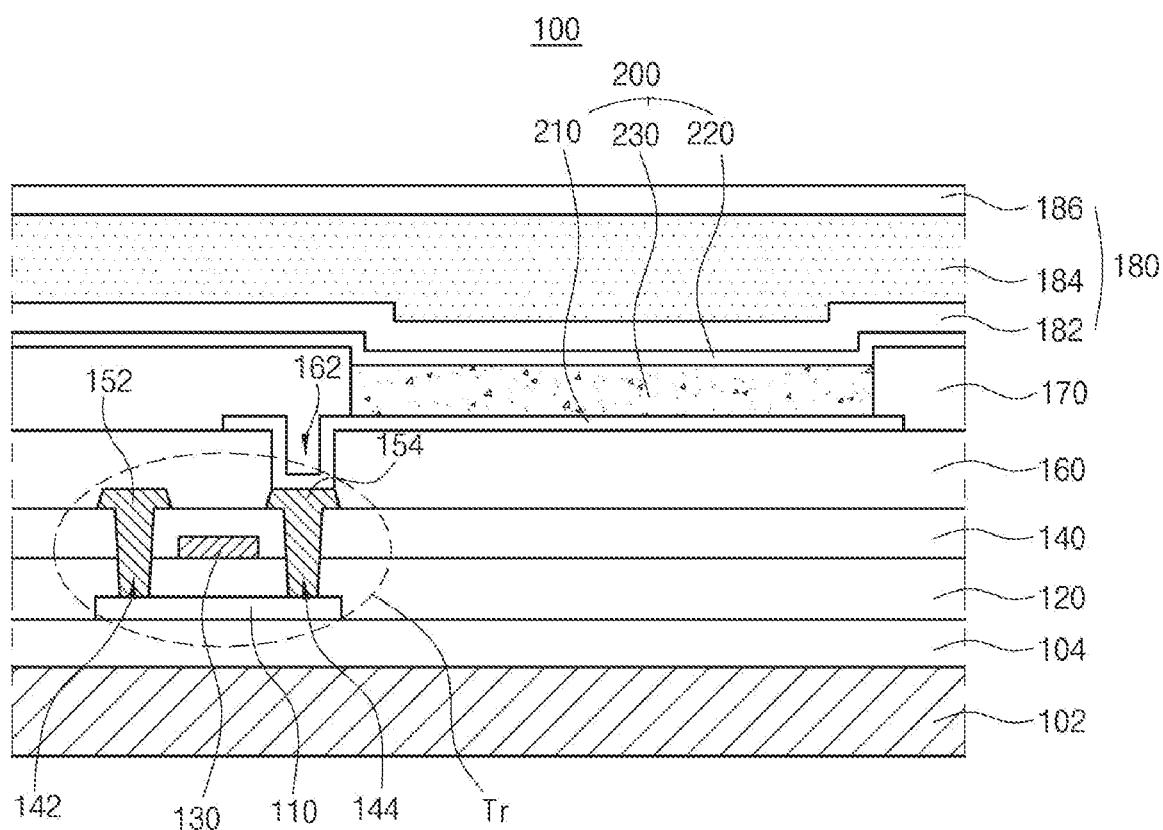
FIG. 1 is a schematic cross-sectional view illustrating a light emitting display device of the present disclosure.

Reference will now be made in detail to aspects of the disclosure, examples of which are illustrated in the accompanying drawings.

[Organic Compound]

An organic compound introduced in a light emitting diode should have excellent luminous property as well as stability even by driving the light emitting diode. An organic compound of the present disclosure includes a tetraphenyl moiety, which has excellent thermal resistance property, and an aryl amino moiety, which has at least one fused hetero aryl group introducing at least one oxygen (O) and/or sulfur (S) on a ring and excellent hole mobility property, bonded directly or indirectly, i.e. through an arylene or hetero arylene linker to the tetraphenyl moiety. The organic compound of the present disclosure may have the following structure of Chemical Formula 1:

Chemical Formula 1

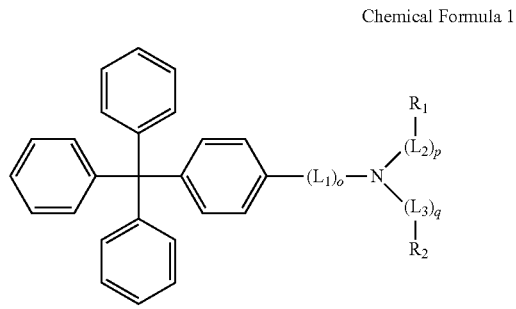

In Chemical Formula 1, each of $R_1$ and $R_2$ an independently is unsubstituted or substituted $C_5$~$C_{30}$ aryl group or an unsubstituted or substituted $C_4$~$C_{30}$ hetero aryl group, wherein at least one of $R_1$ and $R_2$ is an unsubstituted or substituted $C_{10}$~$C_{30}$ hetero aryl group, which has at least one of oxygen (O) and sulfur (S) in a ring. Each of $L_1$, $L_2$, and $L_3$ is independently an unsubstituted or substituted $C_5$~$C_{30}$ arylene group or an unsubstituted or substituted $C_4$~$C_{30}$ hetero arylene group. Each of o, p and q is independently an integer of 0 to 2.

As used herein, the term "unsubstituted" means that hydrogen atom is bonded, and in this case hydrogen atom comprises a protium, deuterium and tritium.

The substituent as used herein the term "substituted" may include, but are not limited to, $C_1$~$C_{20}$ alkyl group unsubstituted or substituted with halogen, $C_1$~$C_{20}$ alkoxy group unsubstituted or substituted with halogen, halogen, cyano group, —$CF_3$, hydroxyl group, carboxyl group, carbonyl group, amino group, $C_1$~$C_{20}$ alkyl amino group, $C_5$~$C_{30}$ aryl amino group, $C_4$~$C_{30}$ hetero aryl amino group, nitro group, hydrazyl group, sulfonyl group, $C_5$—$C_{30}$ alkyl silyl group, $C_5$~$C_{30}$ alkoxy silyl group, $C_3$~$C_{30}$ cycloalkyl silyl group, $C_5$~$C_{30}$ aryl silyl group, $C_4$~$C_{30}$ hetero aryl silyl group, $C_5$~$C_{30}$ aryl group and $C_4$~$C_{30}$ hetero aryl group. As an example, when each of $R_1$ to $R_{15}$ is independently substituted with alkyl group, the alkyl group may be linear or branched $C_1$~$C_{20}$ alkyl group, and preferably linear or branched $C_1$~$C_{10}$ alkyl group.

As used herein, the term "hetero" described in "hetero aromatic ring", "hetero aromatic group", "hetero alicyclic ring", "hetero cyclic alkyl group", "hetero aryl group", "hetero aralkyl group", "hetero aryloxy group", "hetero aryl amino group", "hetero arylene group", "hetero aralkylene group", "hetero aryloxylene group", and the like means that at least one carbon atoms, for example 1 to 5 carbon atoms, forming such aromatic or alicyclic rings are substituted with at least one hetero atoms selected from the group consisting of N, O, S and combination thereof.

In one embodiment, the $C_5$~$C_{30}$ aryl group of $R_1$ and $R_2$ defined in Chemical Formula 1 may include, but are not limited to, a non-fused or fused aryl group such as phenyl, biphenyl, terphenyl, naphthyl, anthracenyl, pentalenyl, indenyl, indenoindenyl, heptaleneyl, biphenylenyl, indacenyl, phenalenyl, phenanthrenyl, benzo-phenanthrenyl, dibenzo-phenathrenyl, azulenyl, pyreneyl, fluoranthenyl, triphenylenyl, chrysenyl, tetraphenylenyl, tetracenyl, pleiadenyl, pycenyl, pentaphenyl, pentacenyl, fluorenyl, indeno-fluorenyl and/or spiro-fluorenyl, each of which may be unsubstituted or substituted.

In another embodiment, the $C_4$~$C_{30}$ hetero aromatic group of $R_1$ to $R_2$ defined in Chemical Formula 1 may include, but are not limited to, unfused or fused hetero aryl group such as pyrrolyl, pyridyl, pyridinyl, pyrimidyl, pyrimidinyl, pyrazinyl, pyridazinyl, triazinyl, imidazolyl, pyrazolyl, indolyl, iso-indolyl, indazolyl, indolizinyl, pyrolizinyl, carbazolyl, benzocarbazolyl, dibenzocarbazolyl, indolocarbazolyl, indenocarbazolyl, benzofurocarbazolyl, benzothienocarbazolyl, quinolinyl, iso-quinolinyl, phthalazinly, quinoxalinyl, cinnolinyl, quinazolinyl, quinozolinyl, quinolizinyl, benzoquinolinyl, benzoiso-quinolinyl, benzoquinoxalinyl, benzoquinazolinyl, acridinyl, phenanthrolinyl, perimidinyl, phenanthridinyl, pteridinyl, naphtharidinyl, furanyl, pyranyl, oxazinyl, oxazolyl, oxadiazolyl, triazolyl, dioxinyl, benzofuranyl, dibenzofuranyl, thiopyranyl, thiazinyl, xanthenyl, chromenyl, iso-chromenyl, thioazinyl, thiophenyl, benzothiophenyl, dibenzothiophenyl, difuropyrazinyl, benzofurobenzofuranyl, benzothienobenzophenyl, benzothienodibenzothiophenyl, benzothienobenzofuranyl, benzothienodibenzofuranyl, phenazinyl, thiophenazinyl, phenoxazinyl, N-substituted spiro fluorenyl, and the like.

In still another exemplary embodiment, when each of $R_1$ and $R_2$ is independently aryl or hetero aryl group other than $C_{10}$~$C_{30}$ fused hetero aryl group, each of the aryl or hetero aryl group may consist of one or two aromatic or hetero aromatic rings. When the number of the aromatic or hetero aromatic rings forming respectively $R_1$ and $R_2$ becomes larger than two, the whole organic compound may have extremely long conjugated structures, and therefore, its energy band gap may be extremely lowered. For example, each of $R_1$ and $R_2$ may be independently, but are not limited to, phenyl, biphenyl and naphthyl, each of which is unsubstituted or substituted with at least one aromatic or hetero aromatic group (e.g. one to three phenyl group, biphenyl group and the like).

The $C_{10}$~$C_{30}$ hetero aryl group, constituting each of $R_1$ and $R_2$, respectively, and including at least one oxygen (O) and/or sulfur (S) on the ring, may include at least three hetero aromatic rings. As an example, the $C_{10}$~$C_{30}$ hetero aryl group of $R_1$ and $R_2$ may include, but are not limited to, a hetero aromatic moiety selected from the group consisting of dibenzofuranyl, dibenzothiophenyl, xanthenyl, dihydrophenazinyl, benzochromenyl, thianthrenyl, phenoxazinyl, phenothiazinyl and phenoxathinyl.

As an example, each of the $C_{10}$~$C_{30}$ fused hetero aryl group of $R_1$ and $R_2$ may independently have a rigid chemical structure of a central 5-membered ring connected to both sides of 6-membering rings, which includes a hetero aryl moiety having an excellent thermal resistance property. As an example, each of the $C_{10}\sim C_{30}$ hetero aryl group of $R_1$ and $R_2$ may have, but are not limited to, a dibenzofuranyl moiety and/or a dibenozothiophenyl moiety. In this case, each of the $C_{10}\sim C_{30}$ hetero aryl group of $R_1$ and $R_2$ may be fused with another aromatic or hetero aromatic ring. As an example, the $C_{10}\sim C_{30}$ fused hetero aryl group having the rigid chemical structure of central 5-membered ring connected to both sides of 6-membering rings may form, but are not limited to, a pyrido-dibenzofuranyl moiety, a pyrido-dibenzothiophenyl moiety, an indeno-dibenzofuranyl moiety, an indeno-dibenzothiophenyl moiety, an indolo-dibenzofuranyl moiety and an indolo-dibenzothiophenyl moiety, each of which is unsubstituted or substituted.

In one non-limiting embodiment, each of $L_1$ and $L_2$ may be an aromatic or hetero aromatic linker. As an example, when each of $L_1$ and $L_2$ defined in Chemical Formula 1 is an unsubstituted or substituted $C_5\sim C_{30}$ arylene, each of $L_1$ and $L_2$ may include, but are not limited to, phenylene, biphenylene, terphenylene, tetraphenylene, indenylene, naphthylene, azulenylene, indacenylene, acenaphthylene, fluorenylene, spiro-fluorenylene, phenalenylene, phenanthrenylene, anthracenylene, fluoranthrenylene, triphenylenylene, pyrenylene, chrysenylene, naphthacenylene, picenylene, perylenylene, pentaphenylene and hexacenylene.

In another embodiment, when each of $L_1$ and $L_2$ defined in Chemical Formula 1 is an unsubstituted or substituted $C_4\sim C_{30}$ hetero arylene, each of $L_1$ and $L_2$ may include, but are not limited to, pyrrolylene, imidazolylene, pyrazolylene, pyridinylene, pyrazinylene, pyrimidinylene, pyridazinylene, iso-indolylene, indolylene, indazolylene, purinylene, quinolinylene, iso-quinolinylene, benzoquinolinylene, phthalazinylene, naphthyridinylene, quinoxalinylene, quinazolinylene, benzoiso-quinolinylene, benzoquinazolinylene, benzoquinoxalinylene, cinnolinylene, phenanthridinylene, acridinylene, phenanthrolinylene, phenazinylene, benzoxazolylene, benzimidazolylene, furanylene, benzofuranylene, thiophenylene, benzothiophenylene, thiazolylene, iso-thiazolylene, benzothiazolylene, iso-oxazolylene, oxazolylene, triazolylene, tetrazolylene, oxadiazolylene, triazinylene, dibenzofuranylene, benzofurodibenzofuranylene, benzothienobenzofuranylene, benzothienodibenzofuranylene, dibenzothiophenylene, benzothienobenzothiophenylene, benzothienodibenzothiophenylene, carbazolylene, benzocarbazolylene, dibenzocarbazolylene, indolocarbazolylene, indenocarbazolylene, benzofurocarbazolylene, benzothienocarbazolylene, imiidazopyrimidinylene and imidazopyridinylene.

In one exemplary embodiment, when the number of the aromatic or hetero aromatic rings forming respectively $L_1$ to $L_3$ becomes too large, the whole organic compound may have extremely long conjugated structures, and therefore, its energy band gap may be extremely lowered. For example, each of $L_1$ to $L_3$ may consist of one or two, preferably one, aromatic or hetero aromatic ring. With regard to the hole injection and hole transport properties, each of $L_1$ to $L_3$ may be independently 5-, 6- or 7-membered aromatic or hetero aromatic ring, and preferably 6-membered aromatic or hetero aromatic ring. As an example, each of $L_1$ to $L_3$ may include, but are not limited to, phenylene, biphenylene, naphthylene, pyrrolylene, imidazolylene, pyrazolylene, pyridinylene, pyrazinylene, pyrimidinylene, pyridazinylene, furanylene and thiophenylene.

The organic compound having the structure of Chemical Formula 1 includes a tetraphenyl moiety, which has an excellent thermal resistance property, and an aryl amino or a hetero aryl amino moiety, which has a high hole mobility or transport property and includes a rigid chemical structure, bonded to the tetraphenyl moiety directly or indirectly, i.e. through an arylene or hetero arylene linker $L_1$. When the organic compound having the structure of Chemical Formula 1 is introduced into a light emitting diode, the light emitting diode can exhibit excellent hole injection and/or transport properties. Hence, the hole injection and hole transportation is not delayed, the light emitting diode can be sufficiently driven even at a low voltage. In addition, when the organic compound having the structure of Chemical Formula 1 is introduced into the light emitting diode, holes and electrons can be injected into the emitting unit in a balance manner, and the light emitting diode can further increase its luminous efficiency.

As an example, when the organic compound of the present disclosure is applied to a hole transport layer or an exciton blocking layer of the light emitting diode, holes can be injected and transported rapidly into an emitting material layer and electron injections into a hole injection area can be prevented. In addition, the organic compound of the present disclosure has excellent hole injection and/or transportation capability. When a compound having deep Lowest Unoccupied Molecular Orbital (LUMO) energy level or a hole injection material is doped with the organic compound to form a charge generation layer, which is disposed adjacently to a hole transfer layer including the organic compound, electrons are moved toward opposite direction (for example, toward anode) of the hole transfer layer including the organic compound, and the holes can be moved toward the direction of the emitting material layer to have charge generation characteristics.

Accordingly, the organic compound having the structure of Chemical Formula 1 may be applied to a charge control layer such as a hole transfer layer, an electron blocking layer and/or a P-type charge generation layer of the light emitting diode. In this case, as holes can be injected rapidly into the emitting material layer, the light emitting diode can drive even at a lower voltage, and thereby reducing its power consumption. In addition, since the stress applied to the materials in the light emitting diode can be reduced so that the light emitting diode can improve its luminous lifetime and improve its luminous efficiency.

In one exemplary embodiment, the organic compound of the present disclosure may include any organic compound having the following structure of Chemical Formula 2:

[Chemical Formula 2]

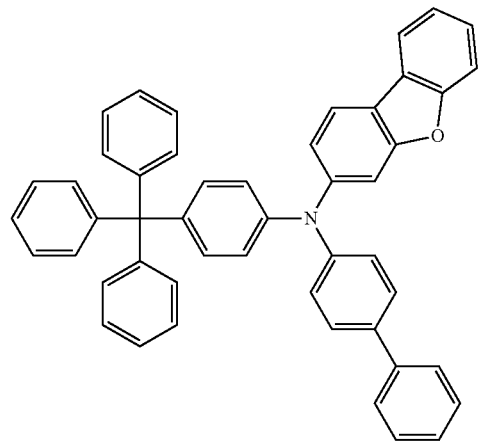

1

2
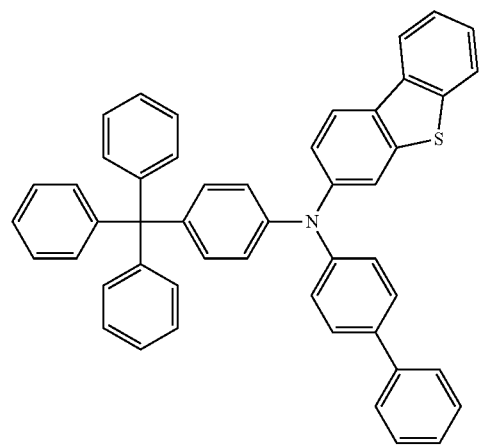
3
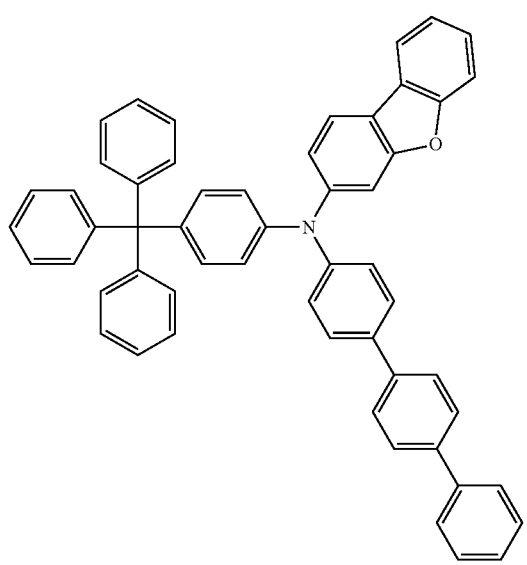
4
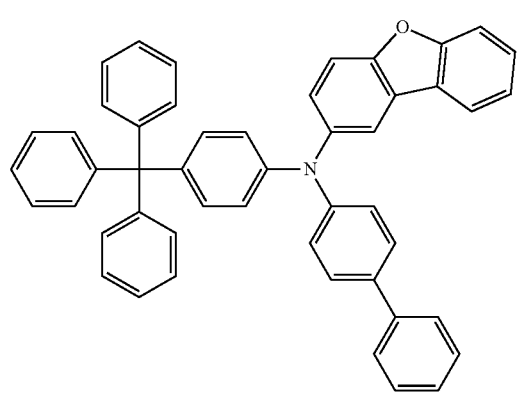
5
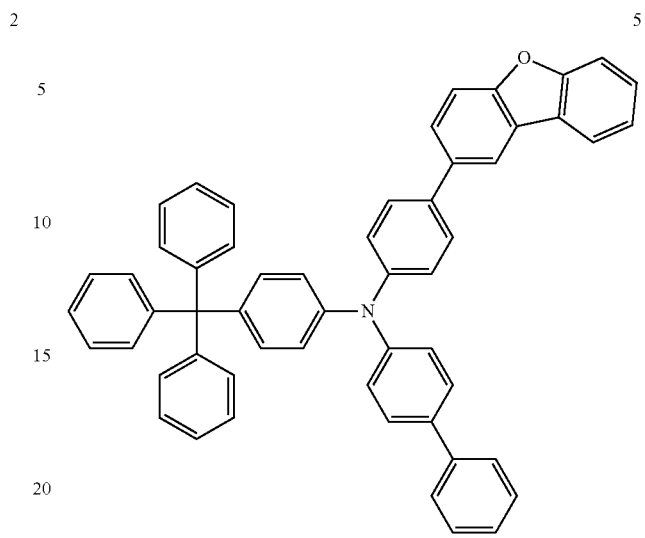
6
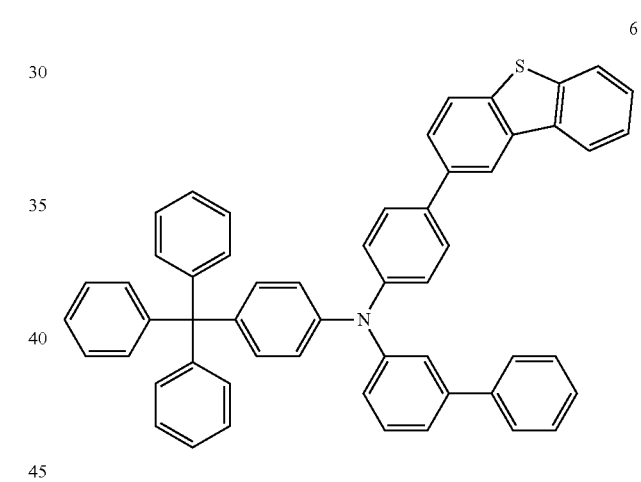
7
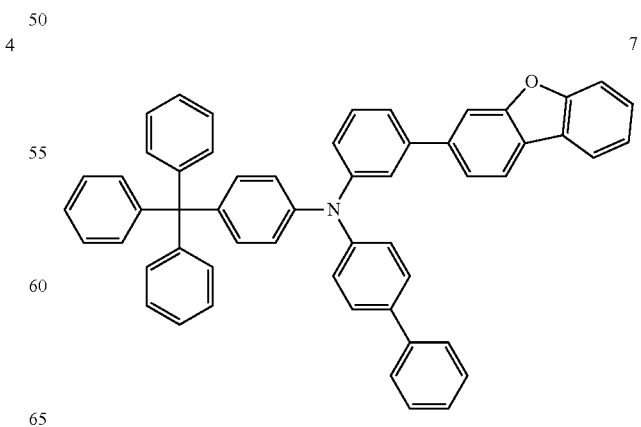

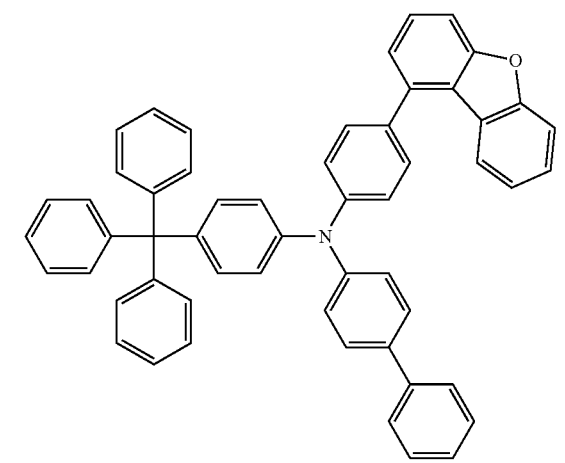
8
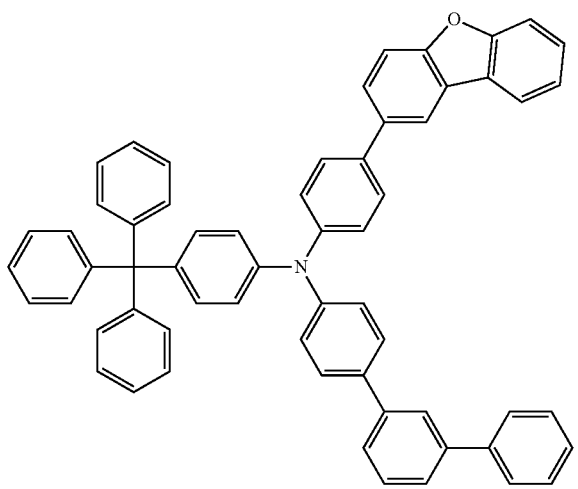
9
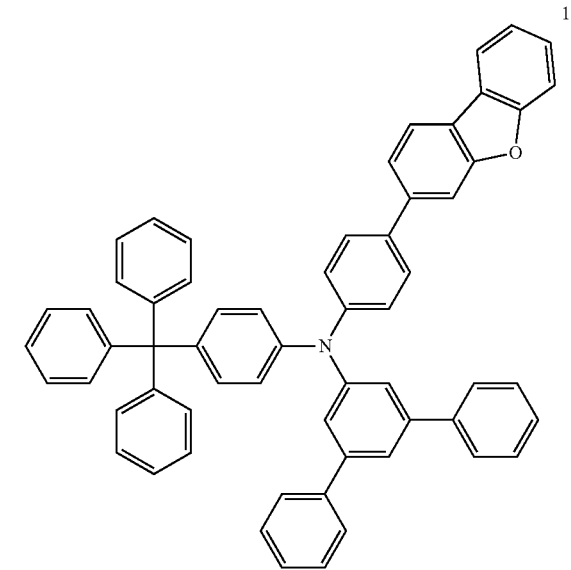
10
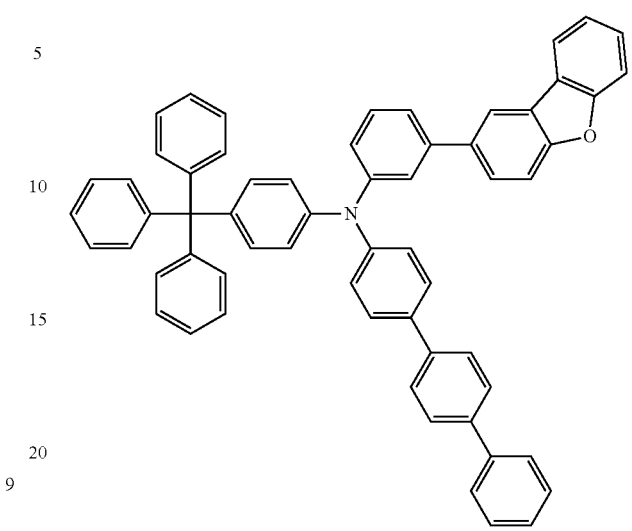
11
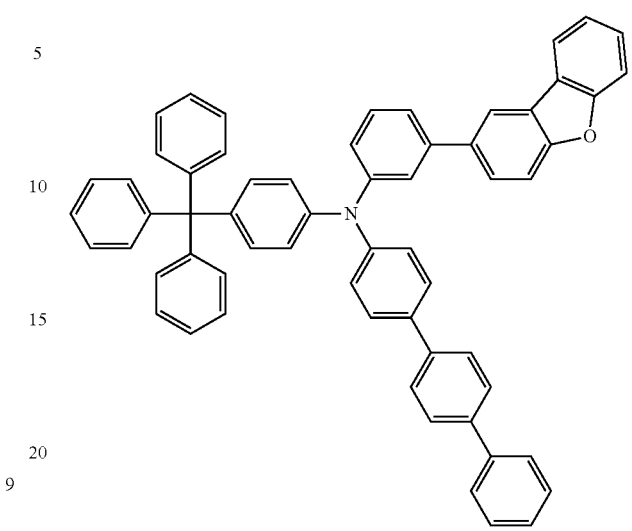
12
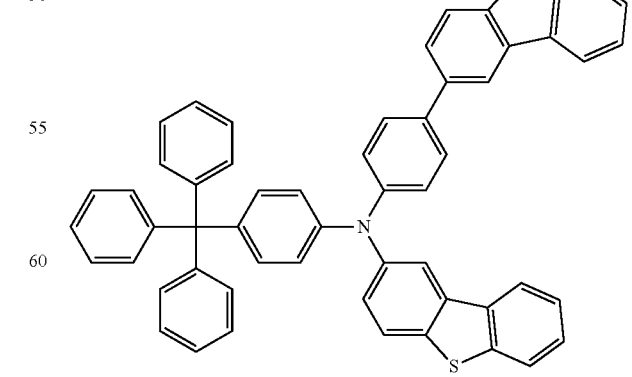
13

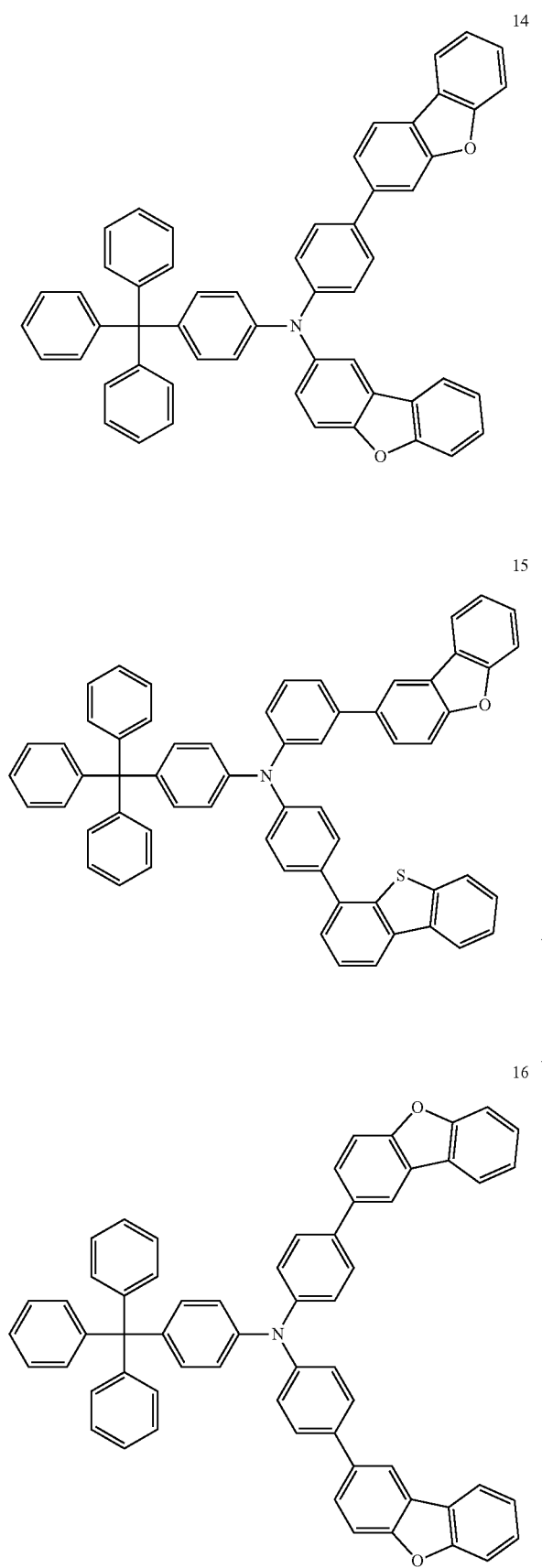
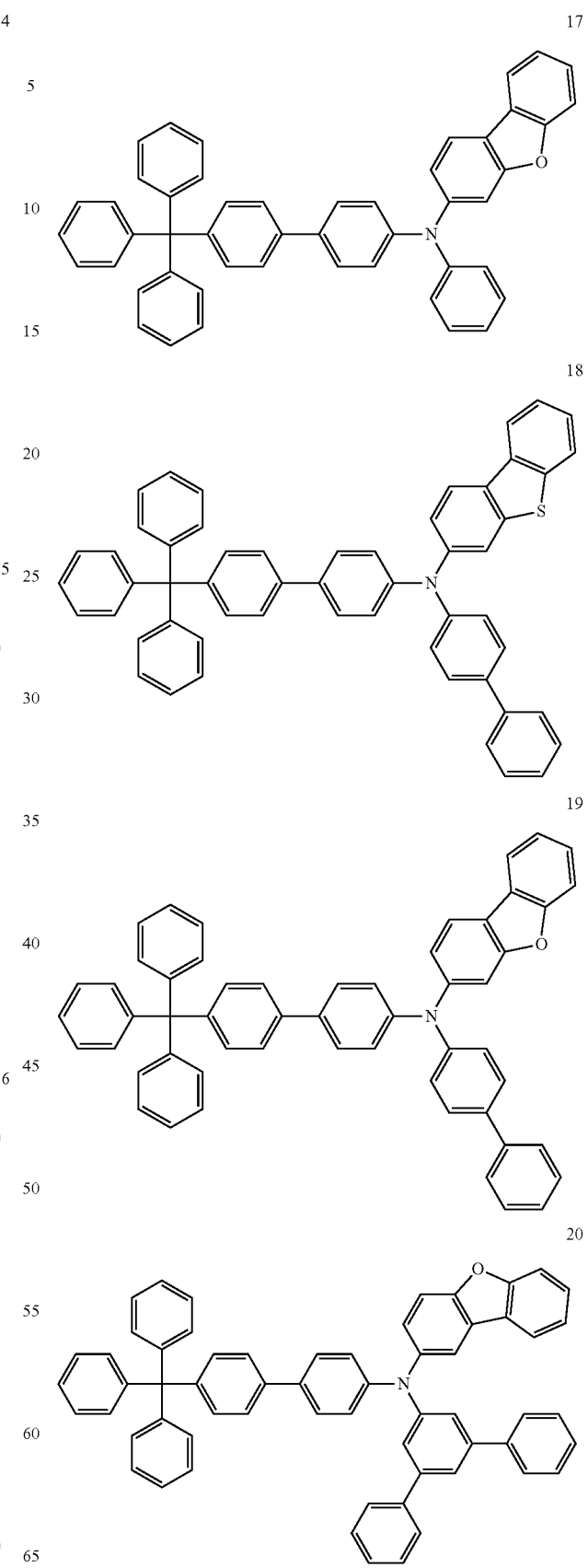

21
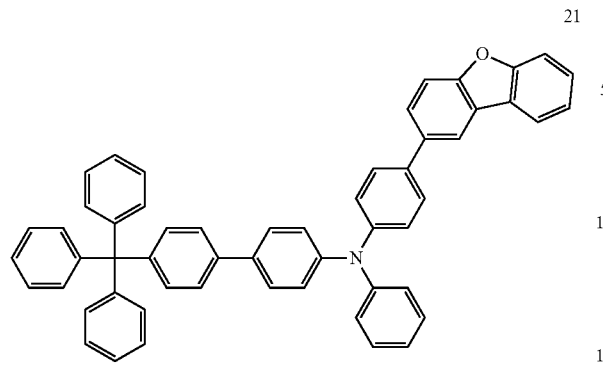
22
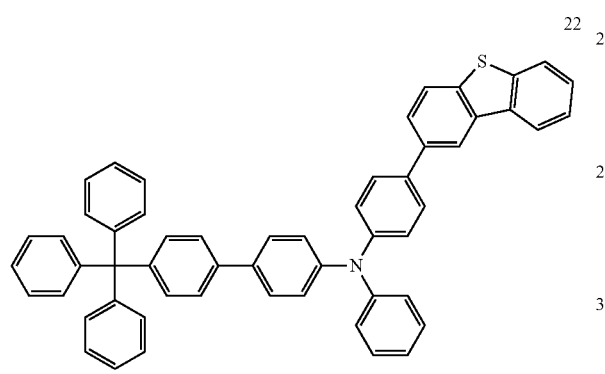
23
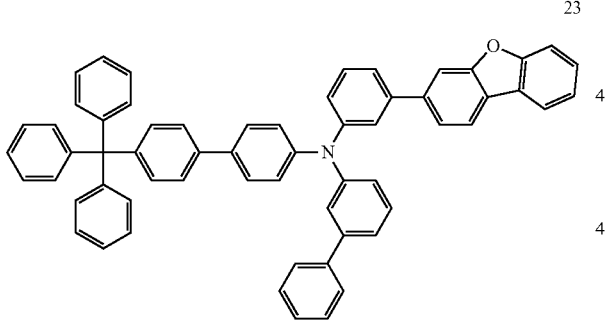
24
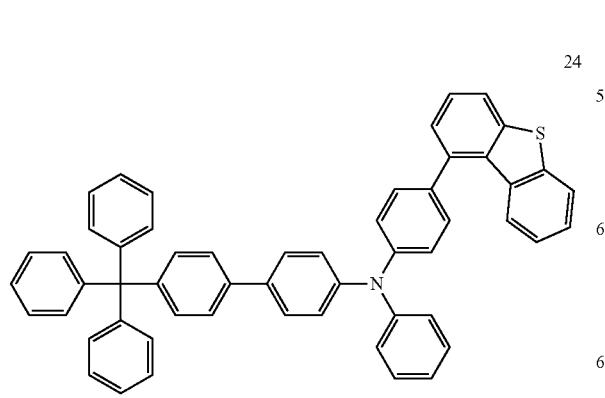
25
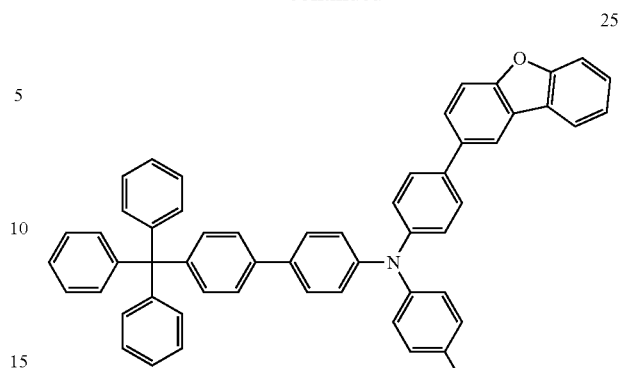
26
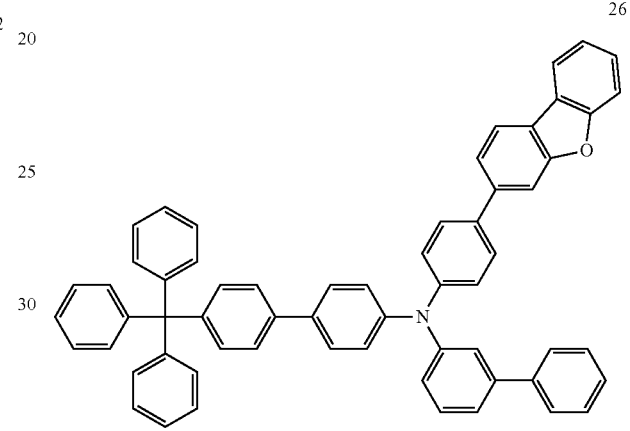
27
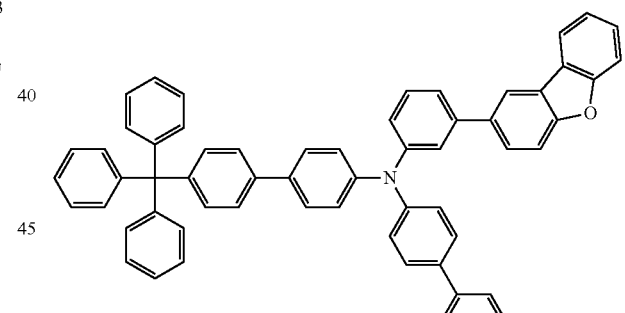
28
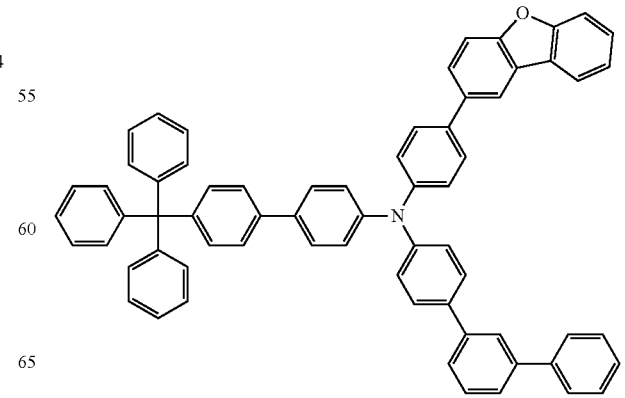

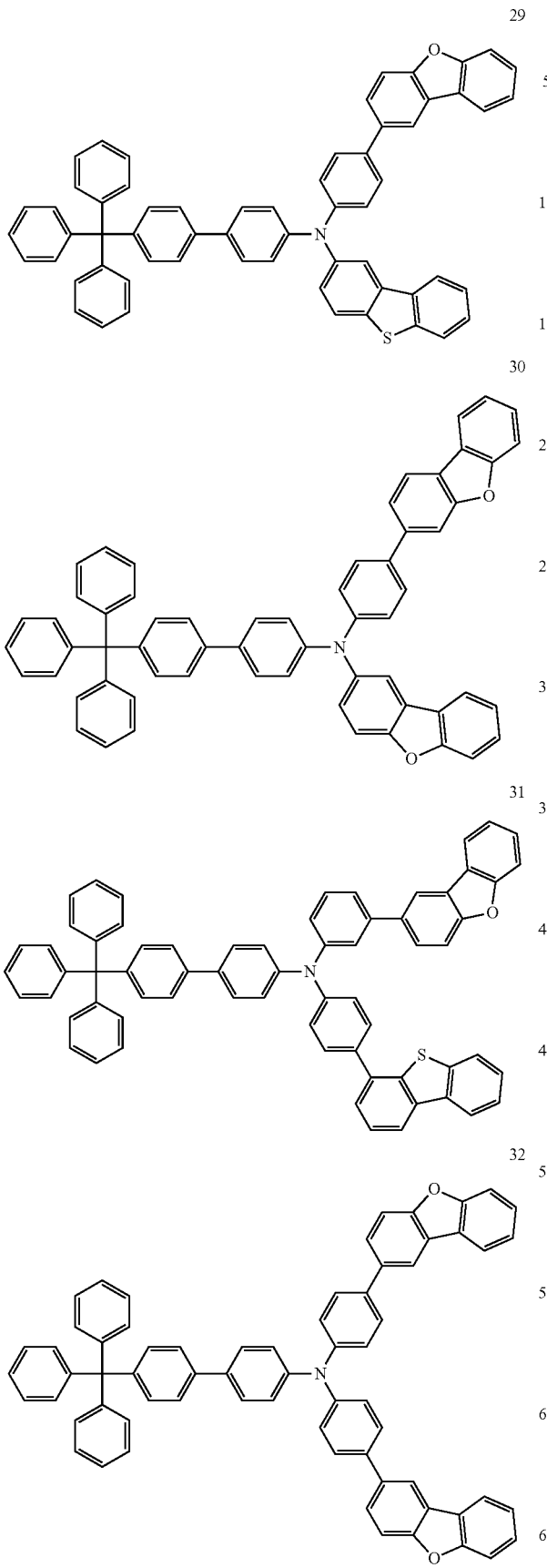
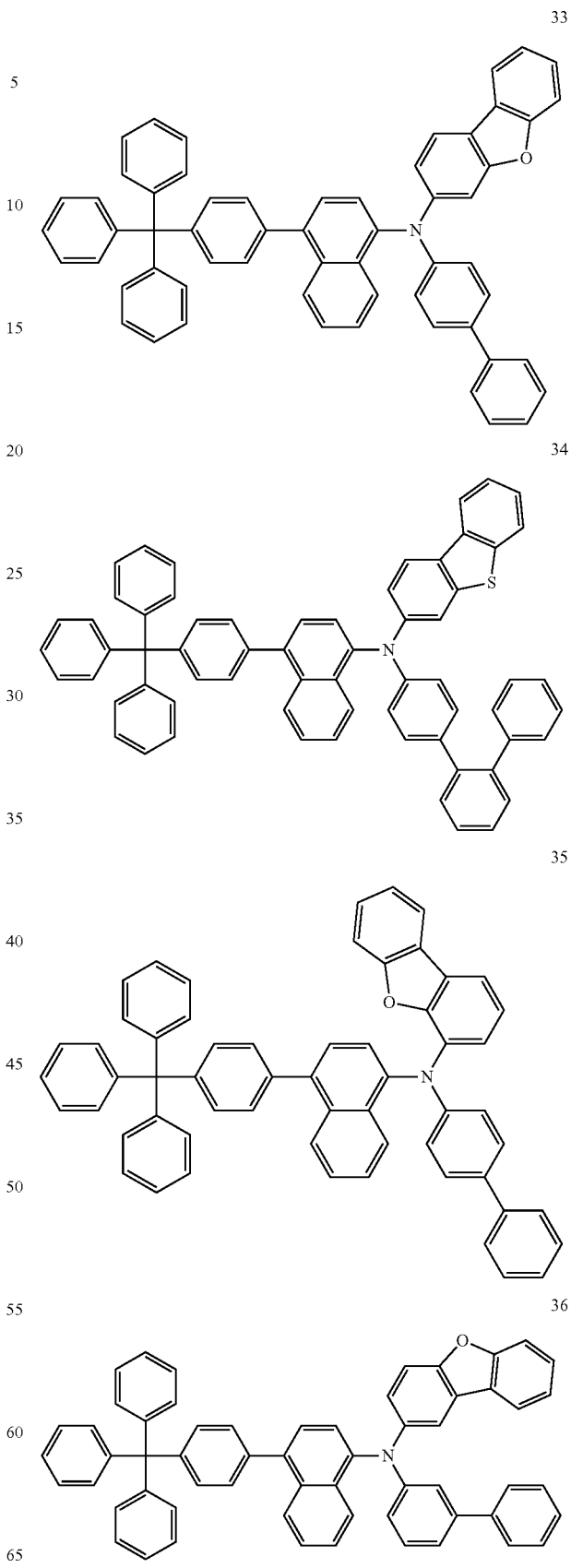

-continued
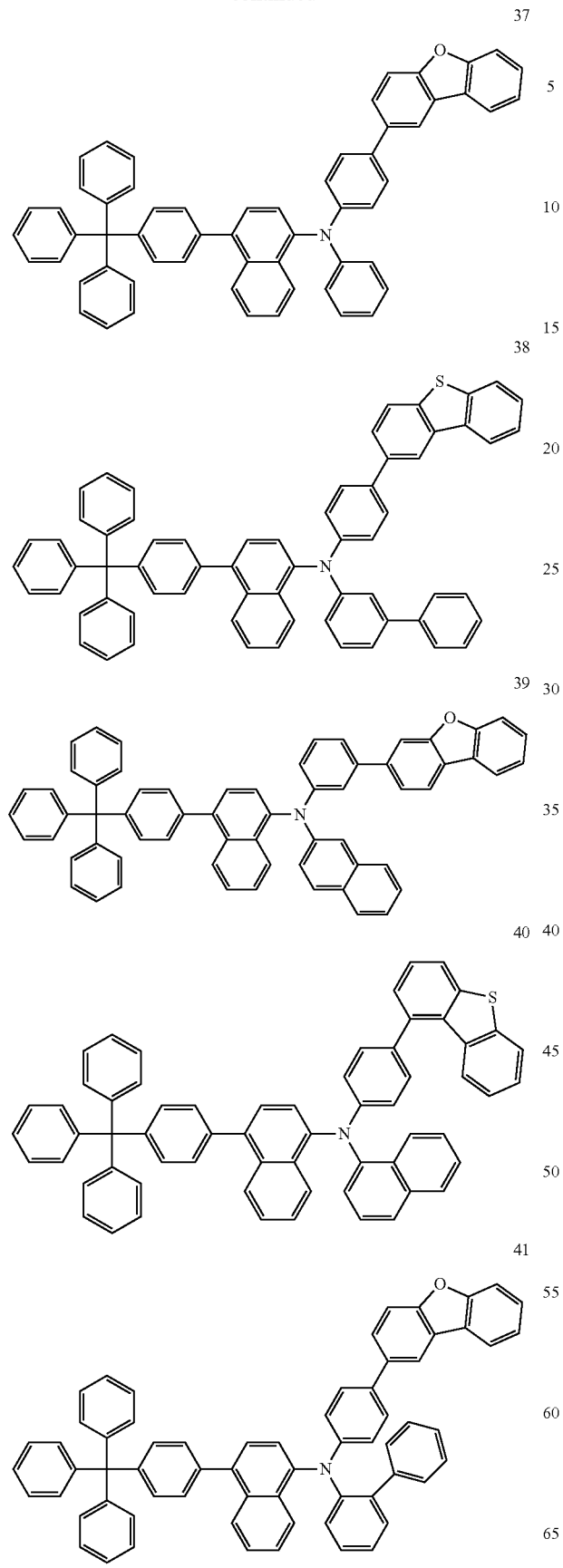
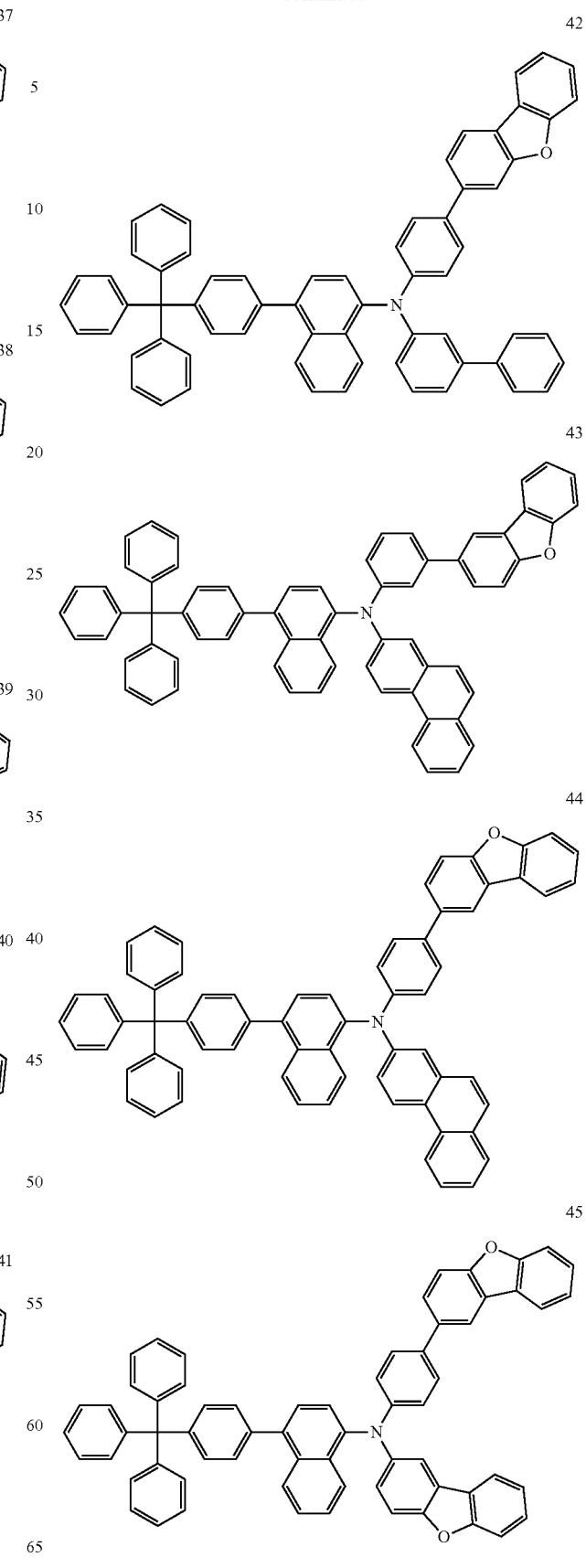

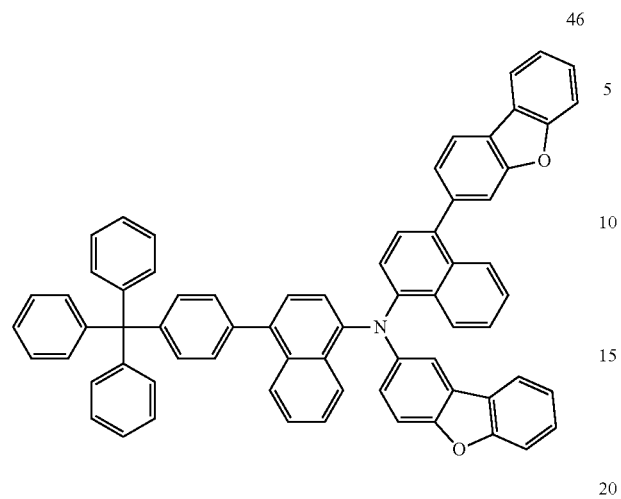
46
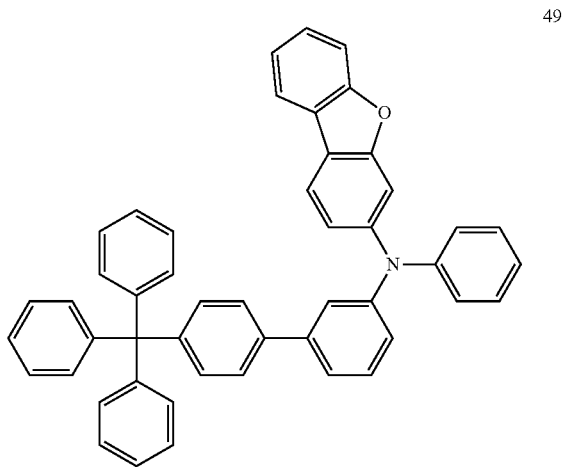
49
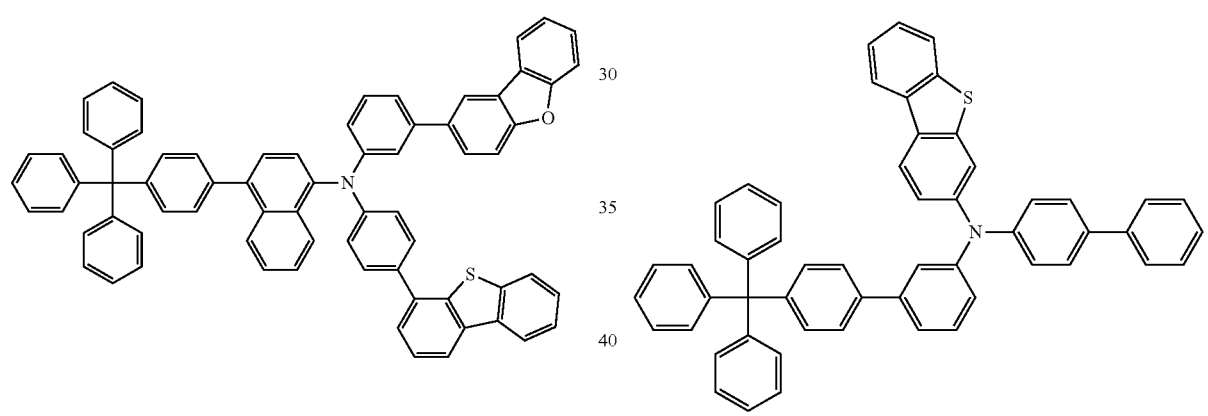
47
50
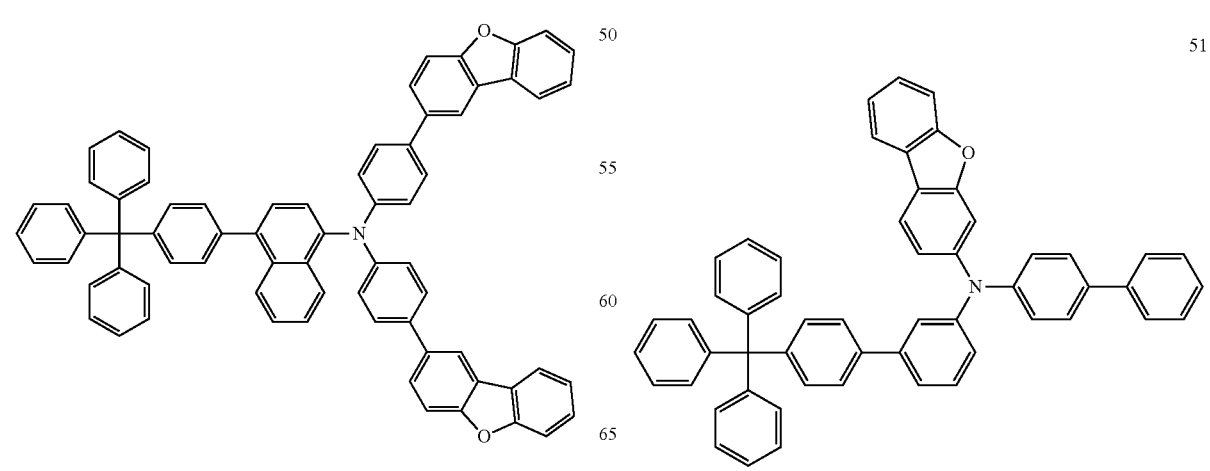
48
51

52
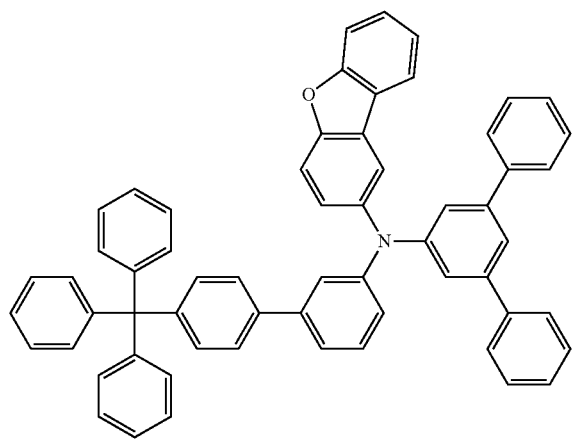
53
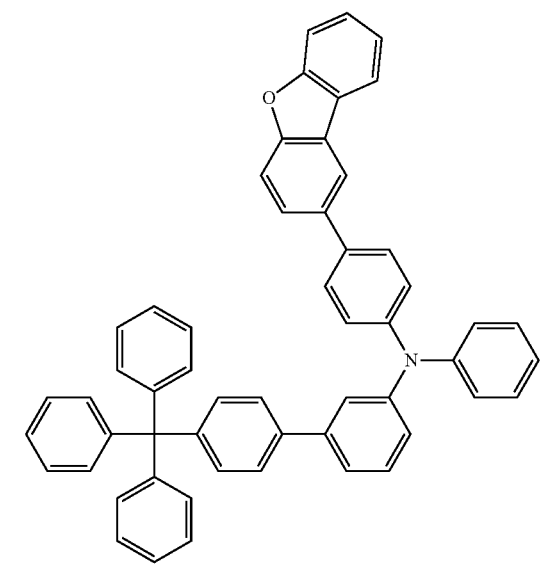
54
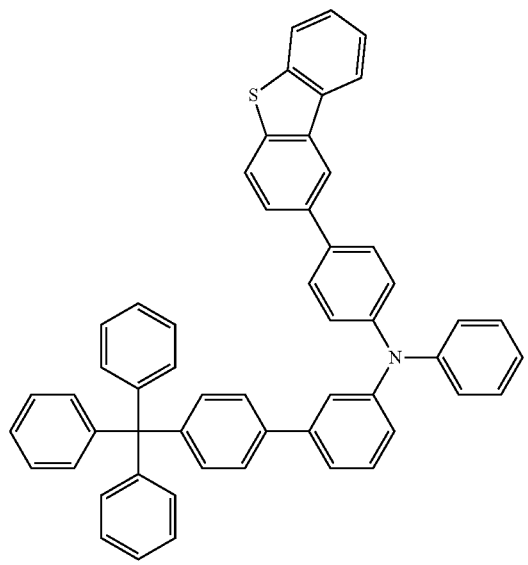
55
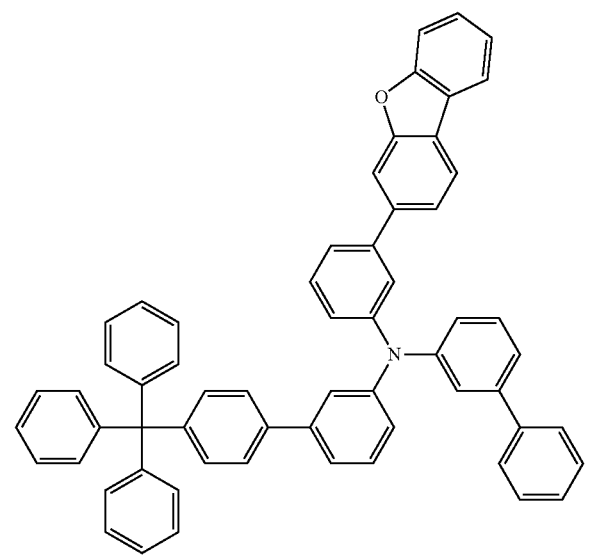
56
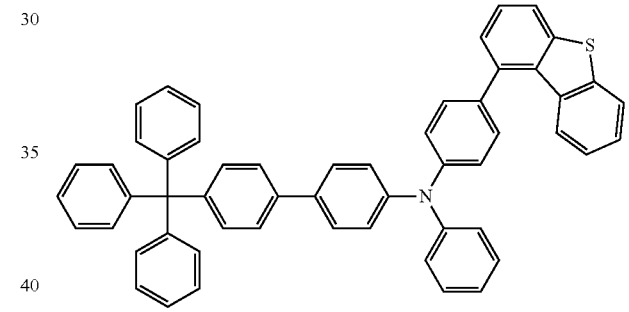
57
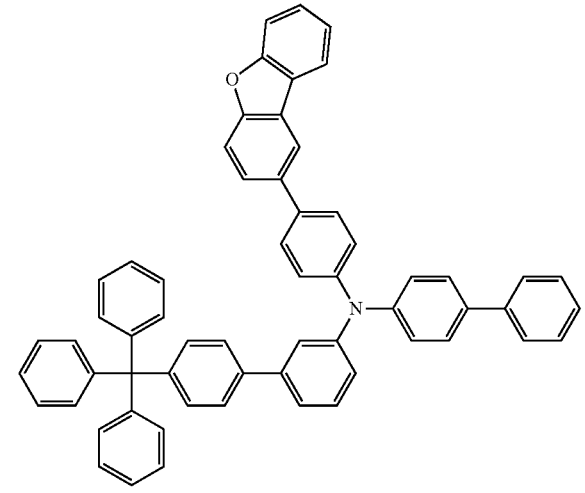

-continued
58
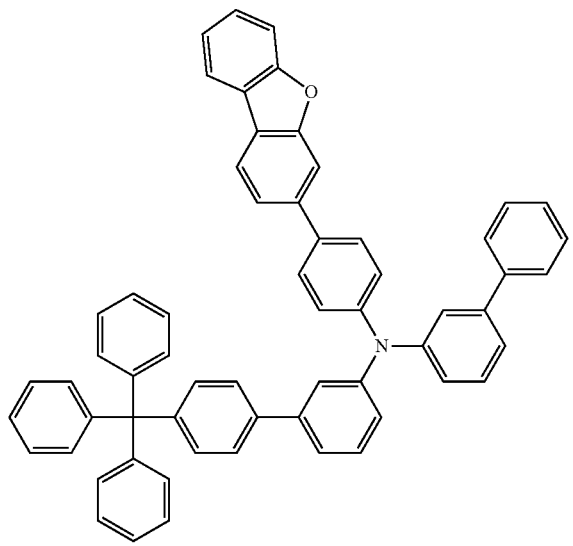
59
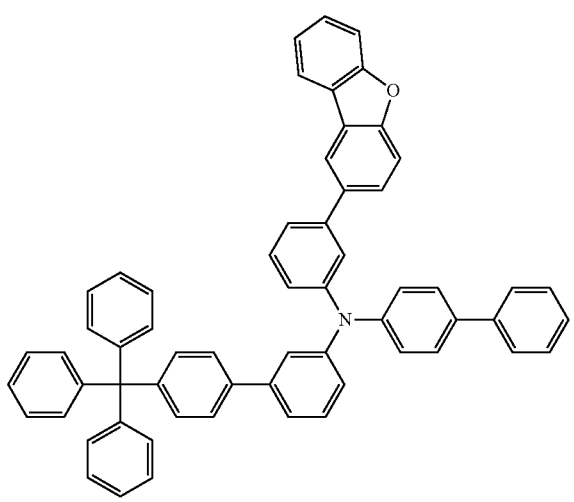
60
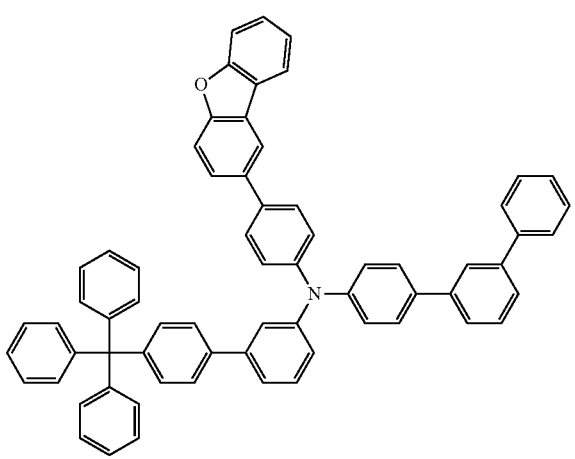
-continued
61
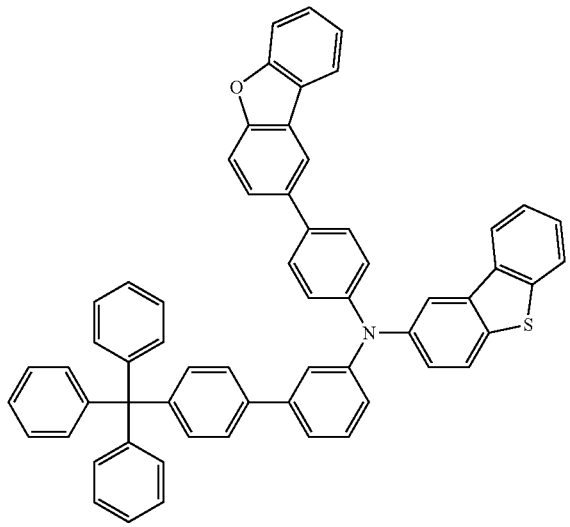
62
63

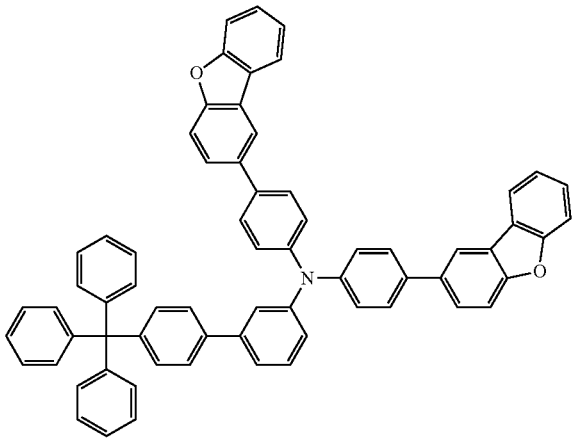

[Light Emitting Device and Light Emitting Diode]

The organic compound having the structure of Chemical Formulae 1 and 2 has excellent thermal resistance property and charge transportation and/or electron blocking properties. Accordingly, it is possible to implement a light emitting diode, for example, an organic light emitting diode (OLED), having a lower driving voltage, excellent luminous efficiency and improved luminous lifetime by applying the organic compound having the structure of Chemical Formulae 1 and 2 into a charge control layer constituting the light emitting diode. The light emitting diode of the present disclosure may be applied to a light emitting device, for example an organic light emitting device, such as a light emitting display device and a light emitting illumination device. A light emitting display device having the light emitting diode of the present disclosure will be explained. FIG. 1 is a schematic cross-sectional view illustrating a light emitting display device of the present disclosure.

As illustrated in FIG. 1, the light emitting display device 100 comprises a substrate 102, a thin-film transistor Tr on the substrate 102, and a light emitting diode 200 connected to the thin film transistor Tr. The thin film transistor Tr comprises a semiconductor layer 110, a gate electrode 130, a source electrode 152 and a drain electrode 154.

The substrate 102 may include, but are not limited to, glass, thin flexible material and/or polymer plastics. For example, the flexible material may be selected from the group, but are not limited to, polyimide (PI), polyethersulfone (PES), polyethylenenaphthalate (PEN), polyethylene terephthalate (PET), polycarbonate (PC) and combination thereof. The substrate 100, over which the thin film transistor Tr and the light emitting diode 200 is arranged, form an array substrate.

A buffer layer 104 may be disposed over the substrate 102, and the thin film transistor Tr is disposed over the buffer layer 104. The buffer layer 104 may be omitted.

A semiconductor layer 110 is disposed over the buffer layer 104. In one exemplary embodiment, the semiconductor layer 110 may include, but is not limited to, oxide semiconductor materials. In this case, a light-shied pattern may be disposed under the semiconductor layer 110, and the light-shield pattern can prevent light from being incident toward the semiconductor layer 110, and thereby, preventing the semiconductor layer 110 from being deteriorated by the light. Alternatively, the semiconductor layer 110 may include polycrystalline silicon. In this case, opposite edges of the semiconductor layer 110 may be doped with impurities.

A gate insulating layer 120 formed of an insulating material is disposed on the semiconductor layer 110. The gate insulating layer 120 may include, but are not limited to, an inorganic insulating material such as silicon oxide ($SiO_x$) or silicon nitride ($SiN_x$).

A gate electrode 130 made of a conductive material such as a metal is disposed over the gate insulating layer 120 so as to correspond to a center of the semiconductor layer 110. While the gate insulating layer 120 is disposed over a whole area of the substrate 102 in FIG. 1, the gate insulating layer 120 may be patterned identically as the gate electrode 130.

An interlayer insulating layer 140 formed of an insulating material is disposed on the gate electrode 130 with covering over an entire surface of the substrate 102. The interlayer insulating layer 140 may include an inorganic insulating material such as silicon oxide ($SiO_x$) or silicon nitride ($SiN_x$), or an organic insulating material such as benzocyclobutene or photo-acryl.

The interlayer insulating layer 140 has first and second semiconductor layer contact holes 142 and 144 that expose both sides of the semiconductor layer 110. The first and second semiconductor layer contact holes 142 and 144 are disposed over opposite sides of the gate electrode 130 with spacing apart from the gate electrode 130. The first and second semiconductor layer contact holes 142 and 144 are formed within the gate insulating layer 120 in FIG. 1. Alternatively, the first and second semiconductor layer contact holes 142 and 144 are formed only within the interlayer insulating layer 140 when the gate insulating layer 120 is patterned identically as the gate electrode 130.

A source electrode 152 and a drain electrode 154, which is made of a conductive material such as a metal, are disposed on the interlayer insulating layer 140. The source electrode 152 and the drain electrode 154 are spaced apart from each other with respect to the gate electrode 130, and contact both sides of the semiconductor layer 110 through the first and second semiconductor layer contact holes 142 and 144, respectively.

The semiconductor layer 110, the gate electrode 130, the source electrode 152 and the drain electrode 154 constitute the thin film transistor Tr, which acts as a driving element. The thin film transistor Tr in FIG. 1 has a coplanar structure in which the gate electrode 130, the source electrode 152 and the drain electrode 154 are disposed over the semiconductor layer 110. Alternatively, the thin film transistor Tr may have an inverted staggered structure in which a gate electrode is disposed under a semiconductor layer and a source and drain electrodes are disposed over the semiconductor layer. In this case, the semiconductor layer may include amorphous silicon.

In FIG. 1, a gate line and a data line, which cross each other to define a pixel region, and a switching element, which is connected to the gate line and the data line, is may be further formed in the pixel region. The switching element is connected to the thin film transistor Tr, which is a driving element. Besides, a power line is spaced apart in parallel from the gate line or the data line, and the thin film transistor Tr may further include a storage capacitor configured to constantly keep a voltage of the gate electrode for one frame.

In addition, the light emitting display device 100 may include a color filter for absorbing a part of light emitted from the light emitting diode 200. For example, the color filter may absorb a light of specific wavelength such as red (R), green (G) or blue (B). In this case, the light emitting display device 100 can implement full-color through the color filter.

For example, when the light emitting display device 100 is a bottom-emission type, the color filter may be disposed on the interlayer insulating layer 140 with corresponding to the light emitting diode 200. Alternatively, when the light emitting display device 100 is a top-emission type, the color filter may be disposed over the light emitting diode 200, that is, a second electrode 220.

A passivation layer 160 is disposed on the source and drain electrodes 152 and 154 over the whole substrate 102. The passivation layer 160 has a flat top surface and a drain contact hole 162 that exposes the drain electrode 154 of the thin film transistor Tr. While the drain contact hole 162 is disposed on the second semiconductor layer contact hole 154, it may be spaced apart from the second semiconductor layer contact hole 154.

The light emitting diode 200 may be an organic light emitting diode (OLED). The light emitting diode 200 includes a first electrode 210 that is disposed on the passivation layer 160 and connected to the drain electrode 154 of the thin film transistor Tr. The light emitting diode 200 further includes an emitting unit 230 and a second electrode 220 each of which is disposed sequentially on the first electrode 210.

The first electrode 210 is disposed in each pixel region. The first electrode 210 may be an anode and include a conductive material having relatively high work function value. For example, the first electrode 210 may include, but are not limited to, a transparent conductive material such as indium tin oxide (ITO), indium zinc oxide (IZO), indium tin zinc oxide (ITZO), tin oxide (SnO), zinc oxide (ZnO), indium cerium oxide (ICO), aluminum doped zinc oxide (Al:ZnO; AZO), and the like.

In one exemplary embodiment, when the light emitting display device 100 is a top-emission type, a reflective electrode or a reflective layer may be disposed under the first electrode 210. For example, the reflective electrode or the reflective layer may include, but are not limited to, aluminum-palladium-copper (APC) alloy.

In addition, a bank layer 170 is disposed on the passivation layer 160 in order to cover edges of the first electrode 210. The bank layer 170 exposes a center of the first electrode 210.

An emitting unit 230 is disposed on the first electrode 210. In one exemplary embodiment, the emitting unit 230 as an emission layer may have a mono-layered structure of an emitting material layer. Alternatively, the emitting unit 230 may have a multiple-layered structure of a hole injection layer, a hole transport layer, an electron blocking layer, an emitting material layer, a hole blocking layer, an electron transport layer and/or an electron injection layer (See, FIGS. 2 to 5). The emitting unit 230 may have a single unit or may have multiple units to form a tandem structure. The emitting unit 230 includes the organic compound having the structure of Chemical Formulae 1 and 2. As an example, a hole transfer layer, an electron blocking layer and/or a charge generation layer may include the organic compound having the structure of Chemical Formulae 1 and 2, and optionally other materials.

The second electrode 220 is disposed over the substrate 102 above which the emitting unit 230 is disposed. The second electrode 220 may be disposed over a whole display area, and may include a conductive material with a relatively low work function value compared to the first electrode 210, and may be a cathode. For example, the second electrode 220 may include, but is not limited to, aluminum (Al), magnesium (Mg), calcium (Ca), silver (Ag), alloy thereof or combination thereof such as aluminum-magnesium alloy (Al—Mg).

In addition, an encapsulation film 180 may be disposed over the second electrode 220 in order to prevent outer moisture from penetrating into the light emitting diode 200. The encapsulation film may have, but are not limited to, a laminated structure of a first inorganic insulating film 182, an organic insulating film 184 and a second inorganic insulating film 186.

As described above, the emitting unit 230 in the light emitting diode 200 includes the organic compound having the structure of Chemical Formulae 1 and 2. The organic compound has excellent thermal resistance property as well as hole transportation and/or electron blocking properties. Therefore, it is possible to implement a light emitting diode having improving luminous efficiency and decreased power consumption owing to its lower driving voltage by applying the organic compound into the emitting unit 230.

Figure 2:
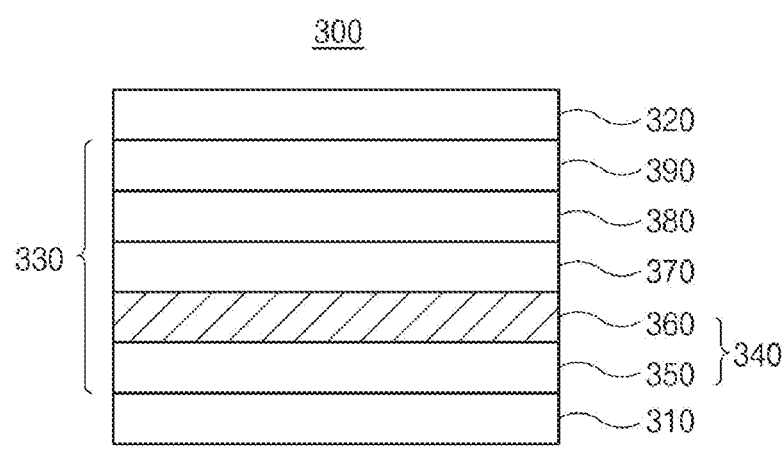
FIG. 2 is a schematic cross-sectional view illustrating a light emitting diode in accordance with an exemplary embodiment of the present disclosure.

FIG. 2 is a schematic cross-sectional view illustrating a light emitting diode in accordance with an exemplary embodiment of the present disclosure. As illustrated in FIG. 2, the light emitting diode (LED) 300 in accordance with an exemplary embodiment of the present disclosure includes first and second electrodes 310 and 320 facing each other and an emitting unit 330 as an emission layer disposed between the first and second electrodes 310 and 320. In one exemplary embodiment, the emitting unit 330 includes a hole transfer layer 340, an emitting material layer (EML) 370, an electron transport layer (ETL) 380 and an electron injection layer (EIL) 390 each of which is laminated sequentially from the first electrode 310. The hole transfer layer 340 may include a hole injection layer (HIL) 350 and a hole transport layer (HTL) 360.

The first electrode 310 may be an anode that provides a hole into the EML 370. The first electrode 310 may include a conductive material having a relatively high work function value, for example, a transparent conductive oxide (TCO). In an exemplary embodiment, the first electrode 310 may include, but are not limited to, indium tin oxide (ITO), indium zinc oxide (IZO), indium tin zinc oxide (ITZO), tin oxide (SnO), zinc oxide (ZnO), indium cerium oxide (ICO), aluminum doped zinc oxide (AZO), and the like.

The second electrode 320 may be a cathode that provides an electron into the EML 360. As described above, the second electrode 320 may include a conductive material having a relatively low work function values, i.e., a highly reflective material such as aluminum (Al), magnesium (Mg), calcium (Ca), silver (Ag), alloy thereof or combination thereof such as aluminum-magnesium alloy (Al—Mg). As an example, each of the first and second electrodes 310 and 320 may be independently laminated with a thickness of, but are not limited to, about 30 nm to about 300 nm.

The hole transfer layer 340 includes the HIL 350 disposed between the first electrode 310 and the EML 370 and the HTL 360 disposed between the HTL 350 and the EML 370.

The HIL 350 is disposed between the first electrode 310 and the HTL 360 and improves an interface property between the inorganic first electrode 310 and the organic HTL 360. In one exemplary embodiment, the HIL 350 may consists of a hole injection material. As an example, the hole injection material may include, but are not limited to, 4,4'4"-Tris(3-methylphenylamino)triphenylamine (MT-DATA), 4,4',4"-Tris(N,N-diphenyl-amino)triphenylamine (NATA), 4,4',4"-Tris(N-(naphthalene-1-yl)-N-phenyl-amino)triphenylamine (1T-NATA), 4,4',4"-Tris(N-(naphthalene-2-yl)-N-phenyl-amino)triphenylamine (2T-NATA), Copper phthalocyanine (CuPc), Tris(4-carbazoyl-9-yl-phenyl)amine (TCTA), N,N'-Diphenyl-N,N'-bis(1-naphthyl)-1,1'-biphenyl-4,4''-diamine (NPB; NPD), 1,4,5,8,9,11-Hexaazatriphenylenehexacarbonitrile (Dipyrazino[2,3-f:2'3'-h]quinoxaline-2,3,6,7,10,11-hexacarbonitrile; HAT-CN), 1,3,5-tris[4-(diphenylamino)phenyl]benzene (TDAPB), poly(3,4-ethylenedio xythiophene)polystyrene sulfonate (PEDOT/PSS), 2,3,5,6-tetrafluoro-7,7,8,8-tetracyanoquinodimethane (F4TCNQ) and/or N-(biphenyl-4-yl)-9,9-dimethyl-N-(4-(9-phenyl-9H-carbazol-3-yl)phenyl)-9H-fluoren-2-amine.

In another exemplary embodiment, the HIL 350 may include the organic compound having the structure of Chemical Formula 1 and 2. As an example, the HIL 350 may include the organic compound having the structure of Chemical Formulae 1 and 2 doped with the hole injection material. In this case, the hole injection material may be doped, but is not limited to, of about 0.1 to about 50% by weight.

Alternatively, the HIL 350 may be divided into two layers. In this case, a first HIL disposed adjacently to the first electrode 310 may consist of the hole injection material, while a second HIL disposed between the first HIL and the HTL 360 may include the organic compound having the structure of Chemical Formulae 1 and 2 doped with the hole injection material. The HIL 350 may be omitted in compliance with a structure of the LED 300.

The HTL 360 is disposed adjacently to the EML 370 between the first electrode 310 and the EML 370. The HTL 360 may include the organic compound having the structure of Chemical Formulae 1 and 2. In one exemplary embodiment, the HTL 360 may consist of the organic compound having the structure of Chemical Formulae 1 and 2.

In another exemplary embodiment, the HTL 360 may include the organic compound having the structure of Chemical Formulae 1 and 2 doped with other hole transport material or include the other hole transport material doped with the organic compound having the structure of Chemical Formulae 1 and 2. As an example, the other hole transport material that may be used in the HTL 360 may include, but are not limited to, NPB, TCTA, tris(trifluoro vinyl ether)-tris(4-carbazoyl-9-yl-phenyl)amine (TFV-TCTA), tris [4-(diethylamino)phenyl] amine, tri-p-tolylamine, N-[1,1'-biphenyl]-4-yl-9,9-diMethyl-N-[4-(9-phenyl-9H-carbazol-3-yl)phenyl]-amine, 1,1-bis(4-(N,N'-di(ptolyl)amino)phenyl) cyclohexane (TAPC), 4,4',4''-tris(3-methylphenylphenylamino)triphenylamine (m-MTDATA), 1,3-bis(N-carbazolyl)benzene (mCP), 4,4'-bis(N-carbazolyl)-1,1'-biphenyl (CBP/DCBP), 1,4-bis(diphenylamino) benzene, 4,4'-bis(3-ethyl-N-carbazolyl)-1,1'-biphenyl, N,N'-bis(3-methylphenyl)-N,N'-diphenylbenzidine (TPD), N,N'-bis[4-[bis(3-methylphenyl)amino]phenyl]-N,N'-diphenyl-[1,1'-biphenyl]-4,4'-diamine (DNTPD), Poly[N,N'-bis(4-butylpnehyl)-N,N'-bis(phenyl)-benzidine] (Poly-TPD), Poly [(9,9-dioctylfluorenyl-2,7-diyl)-co-(4,4'-(N-(4-sec-butylphenyl)diphenylamine))] (TFB), 3,5-Di(9H-carbazol-9-yl)-N,N-diphenylaniline (DCDPA), N-(biphenyl-4-yl)-9,9-dimethyl-N-(4-(9-phenyl-9H-carbazol-3-yl)phenyl)-9H-fluoren-2-amine, N-(biphenyl-4-yl)-N-(4-(9-phenyl-9H-carbazol-3-yl)phenyl)biphenyl-4-amine, N,N'-bis (phenanthren-9-yl)-N,N'-bis(phenyl)-benzidine, CuPc, 4-(dibenzylamino)benzaldehyde-N,N-diphenylhydrazone, 4-(dimethylamino)benzaldehyde diphenylhydrazone, 4-(dimethylamino)benzaldehyde diphenylhydrazone, 2,2'-dimethyl-N,N'-di-[(1-naphthyl)-N,N'-diphenyl]-1,1'-biphenyl-4,4'-diamine, 9,9-dimethyl-N,N'-di(1-naphthyl)-N,N'-diphenyl-9H-fluorene-2,7-diamine), N,N'-di-[(1-naphthyl)-N,N'-diphenyl]-1,1'-biphenyl)-4,4'-diamine, 4-(diphenylamino)benzaldehyde diphenylhydrazone, N,N'-diphenyl-N,N'-di-p-tolylbenzene-1,4-diamine, dipyrazino [2,3-f:2',3'-h]quinoxaline-2,3,6,7,10,11-hexac arbonitrile (HAT-CN6), N,N,N',N'-tetrakis(4-methoxyphenyl)benzidine, N,N,N',N'-tetrakis(3-methylphenyl)-3,3'-dimethylbenzidine, N,N,N',N'-tetrakis(2-naphthyl)benzidine, tetra-N-phenylbenzidine, N,N,N',N'-tetraphenylnaphthalene-2,6-diamine), tin(IV) 2,3-naphthalocyanine dichloride, titanyl phthalocyanine, 1,3,5-tris(diphenylamino)benzene (TDAB), 1,3,5-tris(2-(9-ethylcabazyl-3)ethylene)benzene, 1,3,5-tris [(3-methylphenyl)phenylamino]benzene, 4,4',4''-tris[2-naphthyl(phenyl)amino] triphenylamine) and/or 4,4',4''-tris [phenyl(m-tolyl)amino]triphenylamine.

As an example, the hole transport material may be used as a dopant in the HTL 360. For example, the hole transport material as the dopant may be doped of, but is not limited to, about 0.1 to about 50% by weight in the HTL 360.

In an alternative embodiment, the HTL 360 may be divided into two layers. In this case, a first HTL disposed adjacently to the HIL 350 may consist of the hole transport material. The second HTL disposed adjacently to the EML 370 may consist of the organic compound having the structure of Chemical Formulae 1 and 2 or may include the organic compound having the structure of Chemical Formulae 1 and 2 and the other hole transport material.

In FIG. 2, the hole transfer layer 340 is divided into the HIL 350 and the HTL 360. Alternatively, the hole transfer layer 340 may have a single-layered structure that includes the organic compound having the structure of Chemical Formulae 1 and 2 doped with the hole injection material, for example, MTDATA, NATA, 1T-NATA, 2T-NATA, CuPc, TCTA, NPB/NPD, HAT-CN, TDAPB, PEDOT/PSS, F4TCNQ and/or N-(biphenyl-4-yl)-9,9-dimethyl-N-(4-(9-phenyl-9H-carbazol-3-yl)phenyl)-9H-fluoren-2-amine.

Since the organic compound of the present disclosure shows excellent hole injection and/or transport capabilities, the transfer layer 340 including the organic compound doped with the hole injection material may act as a hole injection layer as well as a hole transport layer. In other words, even when a single-layered hole transfer layer 340 including the organic compound having the structure of Chemical Formulae 1 and 2 doped with the hole injection material is disposed between the first electrode 310 and the EML 370, the LED 300 can show enough hole injection and hole transport properties. In this case, the hole injection material may be doped, but are not limited to, of about 0.1 to about 50% by weight in the single-layered hole transfer layer 360.

In one exemplary embodiment, each of the HIL 350 and the HTL 360 may be laminated with a thickness of, but are not limited to, about 5 nm to about 200 nm, and preferably about 5 nm to about 100 nm.

The EML 370 may include a host and a dopant in which substantial luminescence is performed. As an example, the EML 370 may include a blue (B) host selected from at least one of anthracene-based compounds, pyrene-based compound and perylene-based compounds. Alternatively, the EML 370 may include a green (G) and/or a red (R) host each of which may be a carbazole-based phosphorescent host.

As an example, the host in the EML 370 may include, but are not limited to, tris(8-hydroxyquinoline)aluminum ($Alq_3$), TCTA, poly(9-vinylcarbazole) (PVK), mCP, CBP, 3,3-di(9H-carbazol-9-yl)biphenyl (mCBP), 4,4-Bis(9-carbazolyl)-2,2'-dimethylbiphenyl (CDBP), 4,4'-bis(2,2'-diphenylyinyl)-1,1'-biphenyl (DPVBi), anthracene-based hosts such as 9,10-di-(2-naphtyl)anthracene (ADN), 2-tert-butyl-9,10-di(2-naphthyl)anthracene (TBADN), 2-methyl-9,10-di(2-naphtyl)anthracene (MADN), 9-(2-naphthyl)-10-[3-(2-naphthyl)phenyl]anthracene; 2,5,8,11-tetra-t-butylperylene, distyrylarylene (DSA), 1,3,5-tris(carbazol-9-yl)benzene (TCP) and 1,3,5-tris(N-phenylbenzimidazol-2-yl)benzene (TPBi).

When the EML 370 emits red (R) color light, a red dopant in the EML 370 may include, but are not limited to, an organic compound or an organic metal complex such as 5,6,11,12-tetraphenylnaphthalene (Rubrene), Bis(2-benzo[b]-thiophene-2-yl-pyridine)(acetylacetonate)iridium(III) ($Ir(btp)_2(acac)$), Bis[1-(9,9-diemthyl-9H-fluorn-2-yl)-isoquinoline](acetylacetonate)iridium(III) ($Ir(fliq)_2(acac)$), Bis[2-(9,9-diemthyl-9H-fluorn-2-yl)-quinoline](acetylacetonate)iridium(III) ($Ir(flq)_2(acac)$), Bis-(2-phenylquinoline)(2-(3-methylphenyl)pyridinate)iridium(III) ($Ir(phq)_2typ$) and Iridium(III)bis(2-(2,4-difluorophenyl)quinoline)picolinate (FPQIrpic).

When the EML 370 emits green (G) color light, a green dopant in the EML 370 may include, but are not limited to, an organic compound or an organic metal complex such as N,N'-dimethyl-quinacridone (DMQA), coumarin 6,9,10-bis[N,N-di-(p-tolyl)amino]anthracene (TTPA), 9,10-bis[phenyl(m-tolyl)-amino]anthracene (TPA), Bis(2-phenylpyridine)(acetylacetonate)iridium(III) ($Ir(ppy)_2(acac)$), fac-tris(phenylpyridine)iridium(III) (fac-$Ir(ppy)_3$) and tris[2-(p-tolyl)pyridine]iridium(III) ($Ir(mppy)_3$).

When the EML 370 emits blue (B) color light, a blue dopant in the EML 370 may include, but are not limited to, an organic compound or an organic metal complex such as 4,4'-bis(9-ethyl-3-carbazovinylene)-1,1'-biphenyl (BCzVBi), diphenyl-[4-(2-[1,1;4,1]terphenyl-4-yl-vinyl)-phenyl]-amine, 3,8-bis(diphenylamino)pyrene, 2,5,8,11-tetra-tert-butylpherylene (TBPe), Bis(3,5-difluoro-2-(2-pyridyl)phenyl-(2-carbozylpyridyl)iridium(III) (FirPic), mer-tris(1-phenyl-3-methylimidazolin-2ylidene-C,C2') iridium(III) (mer-$Ir(pmi)_3$) and tris(2-(4,6-difluorophenyl)pyridine)iridium(III) ($Ir(Fppy)_3$).

In still another exemplary embodiment, the EML 370 may include a delayed fluorescent material. The delayed fluorescent material in the EML 370 may include, but are not limited to, 10-(4-(4,6-diphenyl-1,3,5-triazin-2-yl)phenyl)-9,9-dimethyl-9,10-dihydroacridine (DMAC-TRZ), 10,10'-(4,4'-sulfonylbis(4,1-phenylene))bis(9,9-dimethyl-9,10-dihydroacridine) (DMAC-DPS), 10-phenyl-10H,10'H-spiro[acridine-9,9'-anthracen]-10'-one (ACRSA), 3,6-dibenzoyl-4,5-di(1-methyl-9-phenyl-9H-carbazoyl)-2-ethynylbenzonitrile (Cz-VPN), 9,9',9"-(5-(4,6-diphenyl-1,3,5-triazin-2-yl)benzene-1,2,3-triyl) tris(9H-carbazole) (TcZTrz), 9,9'-(5-(4,6-diphenyl-1,3,5-triazin-2-yl)-1,3-phenylene)bis(9H-carbazole) (DczTrz), 9,9',9",9"'-((6-phenyl-1,3,5-triazin-2,4-diyl)bis(benzene-5,3,1-triyl))tetrakis(9H-carbazole (DDczTrz), bis(4-(9H-3,9'-bicarbazol-9-yl)phenyl)methanone (CC2BP), 9'-[4-(4,6-diphenyl-1,3,5-triazin-2-yl)phenyl]-3,3",6,6"-tetraphenyl-9,3':6',9"-ter-9H-carbazole (BDPCC-TPTA), 9'-[4-(4,6-diphenyl-1,3,5-triazin-2-yl)phenyl]-9,3':6',9"-ter-9H-carbazole (BCC-TPTA), 9,9'-(4,4'-sulfonylbis(4,1-phenylene))bis(3,6-dimethoxy-9H-carbazole) (DMOC-DPS), 9-(4-(4,6-diphenyl-1,3,5-triazin-2-yl)phenyl)-3',6'-diphenyl-9H-3,9'-bicarbazole (DPCC-TPTA), 10-(4,6-diphenyl-1,3,5-triazin-2-yl)-10H-phenoxazine (Phen-TRZ), 9-(4-(4,6-diphenyl-1,3,5-triazin-2-yl)phenyl)-9H-carbazole (Cab-Ph-TRZ), 1,2,3,5-Tetrakis(3,6-carbazol-9-yl)-4,6-dicyanobenzene (4CzIPN), 2,3,4,6-tetra(9H-carbazol-9-yl)-5-fluorobenzonitrile (4CZFCN) and/or 10-(4-(4,6-diphenyl-1,3,5-triazin-2-yl)phenyl)-10H-spiro[acridine-9,9'-fluorene] (SpiroAC-TRZ).

When the EML 370 includes the host and the dopant, the EML 370 includes the dopant of, but is not limited to, about 1 to about 50% by weight, and preferably about 5 to about 50% by weight. The EML 370 may be laminated with a thickness of, but are not limited to, about 10 nm to about 200 nm, preferably about 20 nm to about 100 nm, and more preferably about 30 nm to about 50 nm.

The ETL 380 and the EIL 390 are laminated sequentially between the EML 370 and the second electrode 320. The ETL 380 includes a material having high electron mobility so as to provide electrons stably with the EML 370 by fast electron transportation.

In one exemplary embodiment, the ETL 380 may include, but is not limited to, oxadiazole-based compounds, triazole-based compounds, phenanthroline-based compounds, benzoxazole-based compounds, benzothiazole-based compounds, benzimidazole-based compounds, triazine-based compounds, and the like.

Particularly, the ETL 380 may include, but are not limited to, $Alq_3$, 2-biphenyl-4-yl-5-(4-t-butylphenyl)-1,3,4-oxadiazole (PBD), spiro-PBD, lithium quinolate (Liq), TPBi, Bis(2-methyl-8-quinolinolato-N1,O8)-(1,1'-biphenyl-4-olato) aluminum (BAlq), 4,7-diphenyl-1,10-phenanthroline (Bphen), 2,9-Bis(naphthalene-2-yl)4,7-diphenyl-1,10-phenanthroline (NBphen), 2,9-Dimethyl-4,7-diphenyl-1,10-phenathroline (BCP), 3-(4-Biphenyl)-4-phenyl-5-tert-butylphenyl-1,2,4-triazole (TAZ), 4-(Naphthalen-1-yl)-3,5-diphenyl-4H-1,2,4-triazole (NTAZ), 1,3,5-Tri(p-pyrid-3-yl-phenyl)benzene (TpPyPB), 2,4,6-Tris(3'-(pyridin-3-yl)biphenyl-3-yl)1,3,5-triazine (TmPPPyTz), Poly[9,9-bis(3'-(N,N-dimethyl)-N-ethylammonium)-propyl)-2,7-fluorene]-alt-2,7-(9,9-dioctylfluorene)] (PFNBr), tris(phenylquinoxaline) (TPQ), Diphenyl-4-triphenylsilyl-phenylphosphine oxide (TSPO1) and/or 2-[4-(9,10-Di-2-naphthalenyl-2-anthracenyl)phenyl]-1-phenyl-1H-benzimdazole (ZADN).

Alternatively, the ETL 380 may include the above-described organic material doped with metal such as an alkali metal and/or an alkaline earth metal. In this case, the ETL 380 may include the alkali metal or the alkaline earth metal of, but are is limited to, about 1 to about 20% by weight. As an example, the alkali metal or the alkaline earth metal as a dopant in the ETL 380 may include, but is not limited to, lithium (Li), sodium (Na), potassium (K), cesium (Cs), magnesium (Mg), strontium (Sr), barium (Ba) and radium (Ra). In one alternative embodiment, the EML 380 may have a multiple-layered structure.

The EIL 390 is disposed between the second electrode 320 and the ETL 380, and can improve physical properties of the second electrode 320 and therefore, can enhance the life span of the LED 300. In one exemplary embodiment, the EIL 390 may include, but are not limited to, an alkali halide such as LiF, CsF, NaF, $BaF_2$ and the like, and/or an organic metal compound such as lithium benzoate, sodium stearate, and the like. The EIL 380 may be omitted in compliance with a structure of the LED 300.

As an example, each of the ETL 380 and the EIL 390 may be laminated with a thickness of, but is not limited to, about 10 nm to about 200 nm, preferably about 10 nm to 100 nm.

The organic compound of the present disclosure has excellent hole injection properties, hole transportation properties and thermal stability. When the hole transfer layer 340 includes the organic compound having the structure of Chemical Formulae 1 and 2 with or without other proper hole injection and/or transportation materials, the LED 300 can decrease its power consumption by lowering its driving voltage, improve its luminous lifetime and enhance its luminous efficiency.

Figure 3:
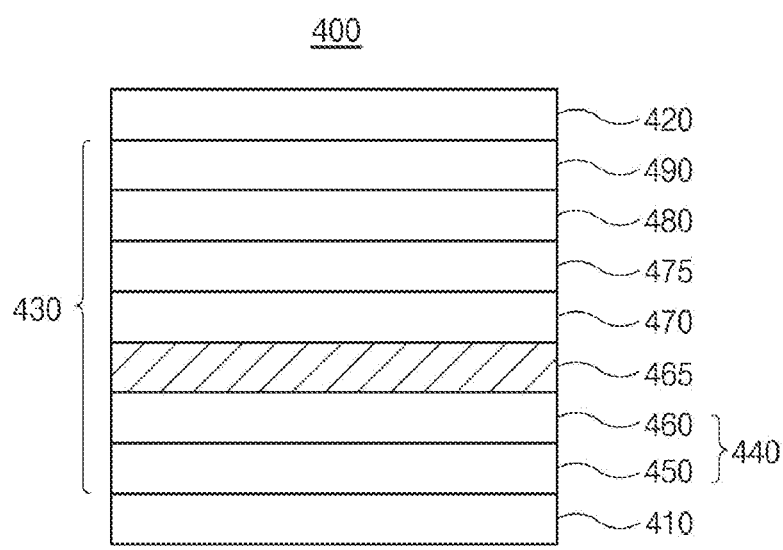
FIG. 3 is a schematic cross-sectional view illustrating a light emitting diode in accordance with another exemplary embodiment of the present disclosure.

In the above first embodiment, the organic compound having the structure of Chemical Formulae 1 and 2 is introduced into the hole transfer layer. The organic compound of the present disclosure may be applied into other charge control layer. FIG. 3 is a schematic cross-sectional view illustrating a light emitting diode in accordance with another exemplary embodiment of the present disclosure.

As illustrated in FIG. 3, the LED 400 in accordance with the second embodiment of the present disclosure include first and second electrodes 410 and 420 facing each other and an emitting unit 430 disposed between the first and second electrodes 410 and 420. The emitting unit 430 as an emission layer includes an emitting material layer (EML) 470. The emitting unit 430 further includes a hole transfer layer 440 disposed between the first electrode 410 and the EML 470, an electron blocking layer (EBL) 455 as a first exciton blocking layer disposed between the hole transfer layer 440 and the EML 470, an electron transport layer (ETL) 480 disposed between the EML 470 and the second electrode 420 and an electron injection layer (EIL) 490 disposed between the ETL 480 and the second electrode 420. Alternatively, the emitting unit 430 may include a hole blocking layer (HBL) 475 as a second exciton blocking layer disposed between the EML 470 and the ETL 480.

As described above, the first electrode 410 may be an anode and include a conductive material having a relatively large work function values such as ITO, IZO, SnO, ZnO, ICO, AZO, and the like. The second electrode 420 may be a cathode and include a conductive material having a relatively small work function values such as Al, Mg, Ca, Ag, alloy thereof or combination thereof. As an example, each of the first and second electrodes 410 and 420 may be laminated with a thickness of, but are not limited to, about 30 nm to about 300 nm.

The hole transfer layer includes a hole injection layer (HIL) 450 disposed between the first electrode 410 and the EML 470 and a hole transport layer (HTL) 460 disposed between the HIL 450 and the EML 470.

In one exemplary embodiment, the HIL 450 consists of a hole injection material. As an example, the hole injection material may include, but are not limited to, MTDATA, NATA, 1T-NATA, 2T-NATA, CuPc, TCTA, NPB(NPD), HAT-CN, TDAPB, PEDOT/PSS, F4TCNQ and/or N-(biphenyl-4-yl)-9,9-dimethyl-N-(4-(9-phenyl-9H-carbazol-3-yl)phenyl)-9H-fluoren-2-amine.

In another exemplary embodiment, the HIL 450 may include the organic compound having the structure of Chemical Formulae 1 and 2 doped with the hole injection material. In still another exemplary embodiment, the HIL 450 may be divided into a first HIL disposed adjacently to the first electrode 410 and a second HIL disposed between the first HIL and the HTL 460. The first HIL may consist of the hole injection material and the second HIL may include the organic compound having the structure of Chemical Formulae 1 and 2 doped with the hole injection material. The HIL 450 may be omitted in compliance with a structure of the LED 400.

The HTL 460 includes the organic compound having the structure of Chemical Formulae 1 and 2. In one exemplary embodiment, the HTL 460 may consist of the organic compound having the structure of Chemical Formulae 1 and 2. In another exemplary embodiment, the HTL 460 may include the organic compound having the structure of Chemical Formulae 1 and 2 doped with other hole transport materials or include the other transport materials doped with the organic compound having the structure of Chemical Formulae 1 and 2.

The other hole transport material which may be used with the organic compound having the structure of Chemical Formulae 1 and 2 as a dopant or a host in the HTL 460 may include, but are not limited to, NPB, TCTA, TFV-TCTA, tris[4-(diethylamino)phenyl]amine, tri-p-tolylamine, N-[1,1'-biphenyl]-4-yl-9,9-diMethyl-N-[4-(9-phenyl-9H-carbazol-3-yl)phenyl]-amine, TAPC, m-MTDATA, mCP, CBP, 1,4-bis(diphenylamino)benzene, 4,4'-bis(3-ethyl-N-carbazolyl)-1,1'-biphenyl, TPD, DNTPD, Poly-TPD, TFB, DCDPA, N-(biphenyl-4-yl)-9,9-dimethyl-N-(4-(9-phenyl-9H-carbazol-3-yl)phenyl)-9H-fluoren-2-amine, N-(biphenyl-4-yl)-N-(4-(9-phenyl-9H-carbazol-3-yl)phenyl)biphenyl-4-amine, N,N'-bis(phenanthren-9-yl)-N,N'-bis(phenyl)-benzidine, CuPc, 4-(dibenzylamino)benzaldehyde-N,N-diphenylhydrazone, 4-(dimethylamino)benzaldehyde diphenylhydrazone, 2,2'-dimethyl-N,N'-di-[(1-naphthyl)-N,N'-diphenyl]-1,1'-biphenyl-4,4'-diamine, 9,9-dimethyl-N,N'-di(1-naphthyl)-N,N'-diphenyl-9H-fluorene-2,7-diamine), N,N'-di-[(1-naphthyl)-N,N'-diphenyl]-1,1'-biphenyl)-4,4'-diamine, 4-(diphenylamino)benzaldehyde diphenylhydrazone, N,N'-diphenyl-N,N'-di-p-tolylbenzene-1,4-diamine, HAT-CN6, N,N,N',N'-tetrakis(4-methoxyphenyl)benzidine, N,N,N',N'-tetrakis(3-methylphenyl)-3,3'-dimethylbenzidine, N,N,N',N'-tetrakis(2-naphthyl)benzidine, tetra-N-phenylbenzidine, N,N,N',N'-tetraphenylnaphthalene-2,6-diamine), tin(IV) 2,3-naphthalocyanine dichloride, titanyl phthalocyanine, TDAB, 1,3,5-tris(2-(9-ethylcabazyl-3)ethylene)benzene, 1,3,5-tris[(3-methylphenyl)phenylamino]benzene, 4,4',4"-tris[2-naphthyl(phenyl)amino]triphenylamine) and/or 4,4',4"-tris[phenyl(m-tolyl)amino]triphenylamine.

In an alternative embodiment, the HTL 460 may include a first HTL disposed adjacently to the HIL 450 and consisting of the hole transport material and a second HTL disposed adjacently to the EML 470, and consisting of the organic compound having the structure of Chemical Formulae 1 and 2 or including the organic compound having the structure of Chemical Formulae 1 and 2 and the other hole transport material.

In addition, the hole transfer layer 440 may have a single-layered structure that includes the organic compound having the structure of Chemical Formulae 1 and 2 doped with the hole injection material. In one exemplary embodiment, each of the HIL 450 and the HTL 460 may be laminated with a thickness of, but are not limited to, about 5 nm to about 200 nm, and preferably about 5 nm to about 100 nm.

When holes are transferred to the second electrode 420 via the EML 470 and/or electrons are transferred to the first electrode 410 via the EML 470, the luminous lifetime and the luminous efficiency of the LED 400 may be reduced. In order to prevent those phenomena, the LED 400 in accordance with the second embodiment of the present disclosure has at least one exciton blocking layer disposed adjacently to the EML 470.

For example, the LED 400 of the exemplary embodiment includes the EBL 465 between the HTL 460 and the EML 470 so as to control and prevent electron transfers. As described above, the organic compound having the structure of Chemical Formulae 1 and 2 shows excellent electron blocking property as well as hole injection and transport properties. In one exemplary embodiment, the EBL 465 may include the organic compound having the structure of Chemical Formulae 1 and 2.

In another exemplary embodiment, the EBL 465 may include other electron blocking material. The other electron blocking material may include, but are not limited to, TCTA, Tris[4-(diethylamino)phenyl]amine, N-(bipnehyl-4-yl)-9,9-dimethyl-N-(4-(9-phenyl-9H-carbazol-3-yl)phenyl)-9H-fluorene-2-amine, TAPC, MTDATA, mCP, mCBP, CuPc, DNTPD, TDAPB, DCDPA, 2,8-bis(9-phneyl-9H-carbazol-3-yl)dibenzo[b,d]thiophene, and/or 3,6-bis(N-carbazolyl)-N-phenyl-carbazole.

The EML 470 may include a host doped with a dopant. The EML 470 may emit red (R), green (G) or blue (B) color light. As an example, the EML 470 may include a blue (B) host selected from at least one of anthracene-based compounds, pyrene-based compounds and perylene-based compounds. Alternatively, the EML 470 may include a green (G) and/or a red (R) host each of which may be a carbazole-based phosphorescent host.

For example, the host in the EML 470 may include, but are not limited to, $Alq_3$, TCTA, PVK, mCP, CBP, mCBP, CDBP, DPVBi, anthracene-based hosts such as AND, TBADN, MADN, (MADN), 9-(2-naphthyl)-10-[3-(2-naphthyl)phenyl]anthracene, DSP, TCP and TPBi. A red (R) dopant in the EML 470 may include, but are not limited to, an organic compound or an organic metal complex such as Rubrene, $Ir(btp)_2(acac)$, $Ir(fliq)_2(acac)$, $Ir(flq)_2(acac)$, $Ir(phq)_2typ$ and FPQlrpic. A green (G) dopant in the EML 470 may include, but are not limited to, an organic compound or an organic metal complex such as DMQA, coumarin 6, TTPA, TPA, $Ir(ppy)_2(acac)$, ac-$Ir(ppy)_3$ and $Ir(m-ppy)_3$. A blue (B) dopant in the EML 470 may include, but is not limited to, an organic compound or an organic metal complex such as BCzVBi, diphenyl[4-(2-[1,1;4,1]terphenyl-4-yl-vinyl)-phenyl]-amine, 3,8-bis(diphenylamino)pyrene, TBPe, FirPic, mer-$Ir(pmi)_3$ and $Ir(Fppy)_3$. Alternatively, the EML 470 may include a delayed fluorescent material. However, the dopant in the EML 470 is not limited thereto.

The EML 470 may be laminated with a thickness of, but is not limited to, about 10 nm to about 200 nm, preferably about 20 nm to about 100 nm, and more preferably about 30 nm to about 50 nm.

The ETL 480 may include, but are not limited to, oxadiazole-based compounds, triazole-based compounds, phenanthroline-based compounds, benzoxazole-based compounds, benzothiazole-based compounds, benzimidazole-based compounds, triazine-based compounds, and the like. Particularly, the ETL 480 may include, but are not limited to, $Alq_3$, PBD, spiro-PBD, Liq, TPBi, BAlq, Bphen, NBphen, BCP, TAZ, NTAZ, TpPyPB, TmPPPyTz, PFNBr, TPQ, TSPO1 and/or ZADN. Alternatively, the ETL 480 may include the above-described organic material doped with metal such as an alkali metal and/or an alkaline earth metal.

The EIL 490 is disposed between the second electrode 420 and the ETL 480. In one exemplary embodiment, the EIL 490 may include, but are not limited to, an alkali halide such as LiF, CsF, NaF, $BaF_2$ and the like, and/or an organic metal compound such as lithium benzoate, sodium stearate, and the like. The EIL 380 may be omitted in compliance with a structure of the LED 300.

As an example, each of the ETL 480 and the EIL 490 may be laminated with a thickness of, but are not limited to, about 10 nm to about 200 nm, preferably about 10 nm to about 100 nm.

In an alternative embodiment, the HBL 475 as a second exciton blocking layer 475 may be disposed between the EML 470 and the ETL 480 so that holes cannot be transferred from the EML 470 to the ETL 480. In one exemplary embodiment, the HBL 475 may include, but are not limited to, oxadiazole-based compounds, triazole-based compounds, phenanthroline-based compounds, benzoxazole-based compounds, benzothiazole-based compounds, benzimidazole-based compounds, and triazine-based compounds.

For example, the HBL 475 may include a compound having a relatively low HOMO energy level compared to the emitting material in EML 470. The HBL 475 may include, but are not limited to, BCP, BAlq, $Alq_3$, PBD, spiro-PBD, Liq, B3PYMPM, Bis[2-(diphenylphosphine)phenyl] ether oxide (DPEPO), 9-(6-(9H-carbazol-9-yl)pyridine-3-yl)-9H-3,9'-bicarbazole, TSPO1 and combination thereof.

Figure 4:
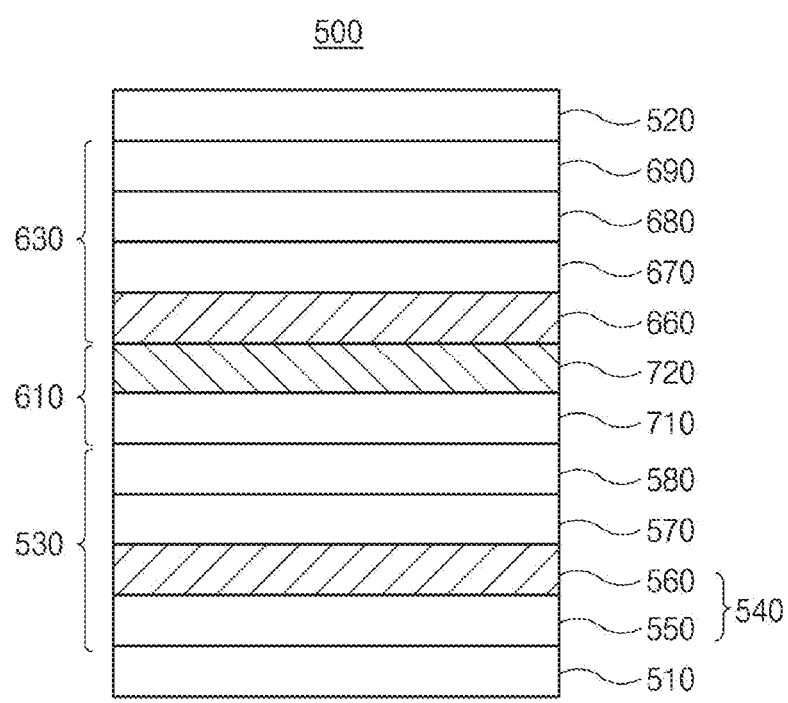
FIG. 4 is a schematic cross-sectional view illustrating a light emitting diode in accordance with still another exemplary embodiment of the present disclosure.

The organic compound of the present disclosure may be applied into a light emitting diode having a tandem structure as well as the light emitting diode having a single emitting unit so that the tandem-structured LED can enhance its luminous efficiency and implement white (W) luminescence. FIG. 4 is a schematic cross-sectional view illustrating a light emitting diode in accordance with still another exemplary embodiment of the present disclosure.

As illustrated in FIG. 4, the LED 500 in accordance with the third embodiment of the present disclosure includes first and second electrodes 510 and 520 facing each other, a first emitting unit (lower emitting unit) 530 as a first emission layer disposed between the first and second electrodes 510 and 520, a second emitting unit (upper emitting unit) 630 as a second emission layer disposed between the first emitting unit 530 and the second electrode 520, and a charge generation layer (CGL) 610 disposed between the first and second emitting units 530 and 630.

As mentioned above, the first electrode 510 may be an anode and include, but are not limited to, a conductive material having a relatively large work function values. As an example, the first electrode 510 may include, but are not limited to, ITO, IZO, SnO, ZnO, ICO, AZO, and the like. The second electrode 520 may be a cathode and may include, but are not limited to, a conductive material having a relatively small work function values such as Al, Mg, Ca, Ag, alloy thereof or combination thereof. Each of the first and second electrodes 510 and 520 may be laminated with a thickness of, but are not limited to, about 30 nm to about 300 nm.

The first emitting unit 530 includes a hole transfer layer 540, a first emitting material layer (first EML; lower EML) 570, a first electron transport layer (first ETL; lower ETL) 580. For example, the hole transfer layer 540 may include a first hole injection layer (first HIL; lower HIL) 550 and a first hole transport layer (first HTL; lower HTL) 560.

The first HIL 550 is disposed between the first electrode 510 and the first EML 560. In one exemplary embodiment, the first HIL 550 may consist of a hole injection material. As an example, the hole injection material may include, but are not limited to, MTDATA, NATA, 1T-NATA, 2T-NATA, CuPc, TCTA, NPB(NPD), HAT-CN, TDAPB, PEDOT/PSS, F4TCNQ and/or N-(biphenyl-4-yl)-9,9-dimethyl-N-(4-(9-phenyl-9H-carbazol-3-yl)phenyl)-9H-fluoren-2-amine.

In another exemplary embodiment, the first HIL 550 may include the organic compound having the structure of Chemical Formulae 1 and 2 doped with the hole injection material. In this case, the first HIL 550 may include the hole injection material of about 0.1 to about 50% by weight. In still another exemplary embodiment, the first HIL 550 may be divided into a lower first HIL disposed adjacently to the first electrode 510 and a lower second HIL disposed between the lower first HIL and the first HTL 560. The lower first HIL may consist of the hole injection material and the lower second HIL may include the organic compound having the structure of Chemical Formulae 1 and 2 doped with the hole injection material. The HIL 450 may be omitted in compliance with a structure of the LED 400.

The first HTL 560 is disposed between the first HIL 550 and the first EML 570, the first EML 570 is disposed between the first HTL 560 and the first ETL 580 and the first ETL 580 is disposed between the first EML 570 and the CGL 610.

In FIG. 4, the hole transfer layer 540 in the first emitting unit 530 is divided into the first HIL 550 and the first HTL 560. Alternatively, the hole transfer layer 540 may have a single-layered structure that includes the organic compound having the structure of Chemical Formulae 1 and 2 doped with the hole injection material.

The second emitting unit 630 includes a second HTL (upper HTL) 660, a second EML (upper EML) 670, a second ETL (upper ETL) 680 and an EIL 690. The second EML 670 is disposed between the second HTL 660 and the second electrode 520, the second ETL 680 is disposed between the second EML 670 and the second electrode 520 and the EIL 690 is disposed between the second ETL 680 and the second electrode 520.

Each of the first and second EMLs 560 and 660 may include a host doped with a dopant and may emit different colors. Each of the first and second EMLs 560 and 660 may emit red (R), green (G), blue (B) yellow (Y) and/or yellow-green (YG) color lights. As an example, the first EML 570 may emit blue (B), red (R), green (G) or yellow-green (YG) color light and the second EML 670 may emit red (R), green (G), blue (B) or yellow-green (YG) color light. In one exemplary embodiment, the first EML 570 may emit blue (B) color light and the second EML 670 emit green (G), yellow-green (YG) or orange color light, each of which has a longer luminescence wavelength than the blue color light. For Example, when the second EML 670 is a yellow-green (YG) emitting material layer, the second EML 670 may include CBP as a host and Tris(2-phenylquinoline) iridium (III) (Ir(2-phq)$_3$) as a dopant.

In accordance with the third embodiment of the present disclosure, at least one of the first and second HTLs 560 and 660 include the organic compound having the structure of Chemical Formulae 1 and 2. In one exemplary embodiment, at least one of the first and second HTLs 560 and 660 may consist of the organic compound having the structure of Chemical Formulae 1 and 2. In another exemplary embodiment, at least one of the first and second HTLs 560 and 660 may include the organic compound having the structure of Chemical Formulae 1 and 2 doped with other hole transport material or included the other hole transport material doped with the organic compound having the structure of Chemical Formulae 1 and 2.

The other hole transport material which may be used with the organic compound having the structure of Chemical Formulae 1 and 2 as dopant or a host in at least one of the first and second HTLs 560 and 660 may include, but are not limited to, NPB, TCTA, TFV-TCTA, tris[4-(diethylamino)phenyl]amine, tri-p-tolylamine, N-[1,1'-biphenyl]-4-yl-9,9-diMethyl-N-[4-(9-phenyl-9H-carbazol-3-yl)pheny]-amine, TAPC, m-MTDATA, mCP, CBP, 1,4-bis(diphenylamino)benzene, 4,4'-bis(3-ethyl-N-carbazolyl)-1,1'-biphenyl, TPD, DNTPD, Poly-TPD, TFB, DCDPA, N-(biphenyl-4-yl)-9,9-dimethyl-N-(4-(9-phenyl-9H-carbazol-3-yl)phenyl)-9H-fluoren-2-amine, N-(biphenyl-4-yl)-N-(4-(9-phenyl-9H-carbazol-3-yl)phenyl)biphenyl-4-amine, N,N'-bis(phenanthren-9-yl)-N,N'-bis(phenyl)-benzidine, CuPc, 4-(dibenzylamino)benzaldehyde-N,N-diphenylhydrazone, 4-(dimethylamino)benzaldehyde diphenylhydrazone, 2,2'-dimethyl-N,N'-di-[(1-naphthyl)-N,N'-diphenyl]-1,1'-biphenyl-4,4'-diamine, 9,9-dimethyl-N,N'-di(1-naphthyl)-N,N'-diphenyl-9H-fluorene-2,7-diamine), N,N'-di-[(1-naphthyl)-N,N'-diphenyl]-1,1'-biphenyl)-4,4'-diamine, 4-(diphenylamino)benzaldehyde diphenylhydrazone, N,N'-diphenyl-N,N'-di-p-tolylbenzene-1,4-diamine, HAT-CN6, N,N,N',N'-tetrakis(4-methoxyphenyl)benzidine, N,N,N',N'-tetrakis(3-methylphenyl)-3,3'-dimethylbenzidine, N,N,N',N'-tetrakis(2-naphthyl)benzidine, tetra-N-phenylbenzidine, N,N,N',N'-tetraphenylnaphthalene-2,6-diamine), tin(IV) 2,3-naphthalocyanine dichloride, titanyl phthalocyanine, TDAB, 1,3,5-tris(2-(9-ethylcabazyl-3)ethylene)benzene, 1,3,5-tris[(3-methylphenyl)phenylamino]benzene, 4,4',4''-tris[2-naphthyl(phenyl)amino]triphenylamine) and/or 4,4',4''-tris[phenyl(m-tolyl)amino]triphenylamine.

In an alternative embodiment, at least one of the first and second HTLs 560 and 660 may include an HTL disposed adjacently to the first HIL 550 or the second HIL and consisting of the hole transport material and another HTL disposed adjacently to the first or second EML 570 or 670 and consisting of the organic compound having the structure of Chemical Formulae 1 and 2 or including the organic compound having the structure of Chemical Formulae 1 and 2 and the other hole transport material. The first and second HTLs 560 and 660 may include the same material or different materials.

In one exemplary embodiment, each of the first HIL 550 and the first and second HTLs 560 and 660 may be laminated with a thickness of, but are not limited to, about 5 nm to about 200 nm, and preferably about 5 nm to about 100 nm.

Each of the first and second ETLs 580 and 680 may include, but are not limited to, oxadiazole-based compounds, triazole-based compounds, phenanthroline-based compounds, benzoxazole-based compounds, benzothiazole-based compounds, benzimidazole-based compounds, triazine-based compounds, and the like, respectively. As an example, each of the first and second ETLs 580 and 680 may include, but are not limited to, Alq$_3$, PBD, spiro-PBD, Liq, TPBi, BAlq, Bphen, NBphen, BCP, TAZ, NTAZ, TpPyPB, TmPPPyTz, PFNBr, TPQ, TSPO1 and/or ZADN, respectively. Alternatively, each of the ETLs 580 and 680 may include the above-described organic material doped with metal such as an alkali metal and/or an alkaline earth metal, respectively. The first and second ETLs 580 and 680 may include the same material or different material.

The EIL 690 is may include, but are not limited to, an alkali halide such as LiF, CsF, NaF, BaF$_2$ and the like, and/or an organic metal compound such as lithium benzoate, sodium stearate, and the like. As an example, each of the first and second ETLs 580 and 680 and the EIL 690 may be laminated with a thickness of, but are not limited to, about 10 nm to about 200 nm, preferably about 10 nm to 100 nm.

The CGL 610 include an N-type CGL 710 disposed adjacently to the first emitting unit 530 and a P-type CGL 720 disposed adjacently to the second emitting unit 630. The N-type CGL 710 injects electrons into the first emitting unit 530 and the P-type CGL 720 injects holes into the second emitting unit 630.

As an example, the N-type CGL 710 may be an organic layer doped with an alkali metal such as Li, Na, K and/or Cs and/or an alkaline earth metal such as Mg, Sr, Ba and/or Ra. For example, a host used in the N-type CGL 710 may include, but are not limited to, an organic compound such as Bphen or MTDATA. The alkali metal or the alkaline earth metal may be doped by about 0.01 wt % to about 30 wt %.

The P-type CGL 720 may include the organic compound having the structure of Chemical Formulae 1 and 2. For example, the P-type CGL 720 may include the organic compound having the structure of Chemical Formulae 1 and 2 doped with the hole injection material. The dopant as the hole injection material in the P-type CGL 720 may include, but are not limited to, MTDATA, NATA, 1T-NATA, 2T-NATA, CuPc, TCTA, NPB(NPD), HAT-CN, TDAPB, PEDOT/PSS, F4TCNQ and/or N-(biphenyl-4-yl)-9,9-dimethyl-N-(4-(9-phenyl-9H-carbazol-3-yl)phenyl)-9H-fluoren-2-amine. When the P-type CGL 720 includes the organic compound having the structure of Chemical Formulae 1 and 2 and the hole injection material, the P-type CGL 720 may include the hole injection material of, but is not limited to, about 0.1 to about 50% by weight.

In FIG. 4, a second HIL (upper HIL) may be disposed between the P-type CGL 720 and the second HTL 660 and/or between the N-type CGL 710 and the P-type CGL 720. When the second HIL is introduced in the LED 500, the holes generated in the P-type CGL 720 may be injected and transported effectively to the second emitting unit 630.

The second HIL may include the organic compound having the structure of Chemical Formulae 1 and 2. In one exemplary embodiment, the second HIL may include the organic compound having the structure of Chemical Formulae 1 and 2 doped with the hole injection material, e.g. MTDATA, NATA, 1T-NATA, 2T-NATA, CuPc, TCTA, NPB(NPD), HAT-CN, TDAPB, PEDOT/PSS, F4TCNQ and/or N-(biphenyl-4-yl)-9,9-dimethyl-N-(4-(9-phenyl-9H-carbazol-3-yl)phenyl)-9H-fluoren-2-amine. In this case, the first HIL 550 and the second HIL may include the same material or different materials.

As described above, the organic compound of the present disclosure shows excellent hole injection and transport properties as well as thermal stability. When the P-type CGL 720 includes the organic compound having the structure of Chemical Formulae 1 and 2 doped with the hole injection material, the holes generated in the P-type CGL 720 may be provided effectively into the second emitting unit 630. The tandem-structured LED 500 which includes the first and second HTLs 560 and 660, the P-type CGL 720, the first HIL 550 and the second HIL, each of which consists of the organic compound having the structure of Chemical Formulae 1 and 2 or includes the organic compound having the structure of Chemical Formulae 1 and 2 mixed or doped with other proper hole injection material and/or hole transport material, is capable of implementing white (W) light emission at a lower driving voltage. In other words, the LED 500 can improve its luminous lifetime and luminous efficiency by using the organic compound of the present disclosure.

Figure 5:
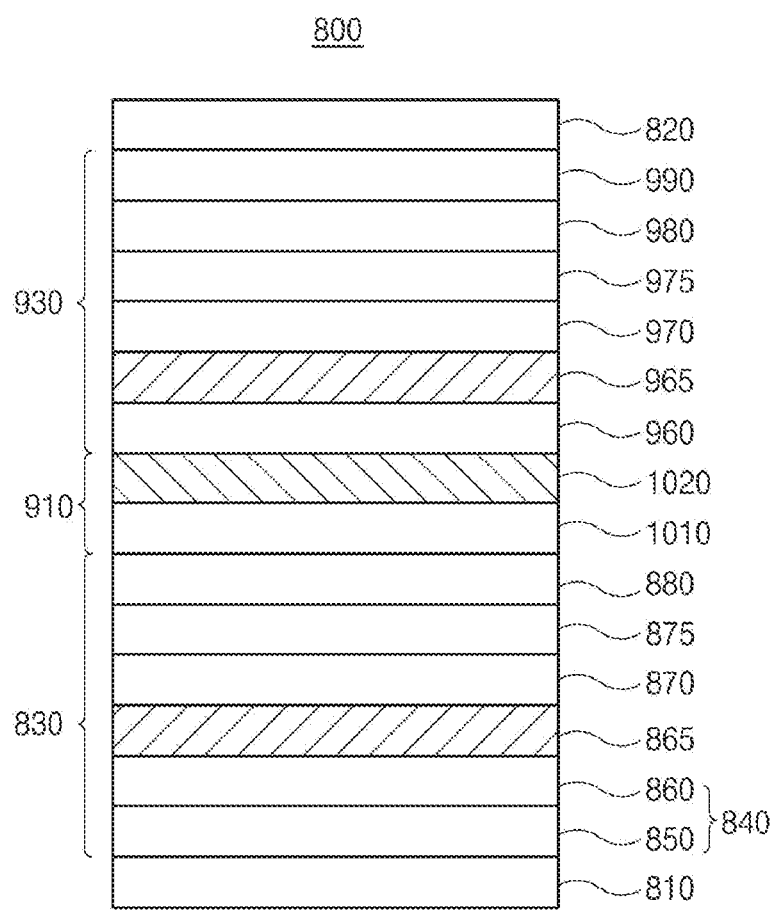
FIG. 5 is a schematic cross-sectional view illustrating a light emitting diode in accordance with still another exemplary embodiment of the present disclosure.

FIG. 5 is a schematic cross-sectional view illustrating a light emitting diode in accordance with still another exemplary embodiment of the present disclosure. As illustrated in FIG. 5, the LED 800 in accordance with the fourth embodiment of the present disclosure includes first and second electrodes 810 and 820 facing each other, a first emitting unit (lower emitting unit) 830 as a first emission layer disposed between the first and second electrodes 810 and 820, a second emitting unit (upper emitting unit) 930 as a second emission layer disposed between the first emitting unit 830 and the second electrode 820, and a charge generation layer (CGL) 910 disposed between the first and second emitting units 830 and 930.

As mentioned above, the first electrode 810 may be an anode and include, but is not limited to, a conductive material having a relatively large work function values. As an example, the first electrode 810 may include, but are not limited to, ITO, IZO, SnO, ZnO, ICO, AZO, and the like. The second electrode 820 may be a cathode and may include, but are not limited to, a conductive material having a relatively small work function values such as Al, Mg, Ca, Ag, alloy thereof or combination thereof. Each of the first and second electrodes 810 and 820 may be laminated with a thickness of, but are not limited to, about 30 nm to about 300 nm.

The first emitting unit 830 includes a hole transfer layer 840, a first electron blocking layer (first EBL; lower EBL) 865, a first emitting material layer (first EML; lower EML) 870, a first electron transport layer (first ETL; lower ETL) 880. Alternatively, the first emitting unit 830 may further include a first hole blocking layer (first HBL; lower HBL) 875.

The hole transfer layer 840 may include a first hole injection layer (first HIL; lower HIL) 850 and a first hole transport layer (first HTL; lower HTL) 860. The first HIL 850 is disposed between the first electrode 810 and the first EML 860, the first HTL 860 is disposed between the first HIL 850 and the first EML 870 and the first EBL 865 is disposed between the first HTL 860 and the first EML 870. In other words, the first EBL 865 for preventing electron transportation may be disposed between the first electrode 810 and the first EML 870 independently of the first HTL 860.

The first EML 870 is disposed between the first EBL 865 and the first ETL 880 and the first ETL 880 is disposed between the first EML 870 and the CGL 910. In addition, the first HBL 875 may be disposed between the first EML 870 and the first ETL 880.

In FIG. 5, the hole transfer layer 840 in the first emitting unit 830 is divided into the first HIL 850 and the first HTL 860. Alternatively, the hole transfer layer 840 may have a single-layered structure that includes the organic compound having the structure of Chemical Formulae 1 and 2 doped with the hole injection material.

The second emitting unit 930 includes a second HTL (upper HTL) 960, a second EBL (upper EBL) 965, a second EML (upper EML) 970, a second ETL (upper ETL) 980 and an EIL 990. Alternatively, the second emitting unit 930 may further include a second HBL (upper HBL) 975.

The second HTL 960 is disposed between the CGL 910 and the second EML 970 and the second EBL 965 is disposed between the second HTL 960 and the second EML 970. In other words, the second EBL 965 for preventing electron transportation may be disposed between the first electrode CGL 910 and the second EML 970 independently of the second HTL 960.

The second ETL 980 is disposed between the second EML 970 and the second electrode 820 and the EIL 990 is disposed between the second ETL 980 and the second electrode 820. In addition, the second HBL 975 is disposed between the second EML 970 and the second ETL 980 in order to prevent hole transportation. In one exemplary embodiment, a second HIL may be disposed between a P-type CGL 1020 and the second HTL 960 and/or between an N-type CGL 1010 and the P-type CGL 1020.

Each of the first and second EMLs 860 and 960 may include a host doped with a dopant and may emit different colors. As an example, the first EML 870 may emit blue (B), red (R), green (G) or yellow-green (YG) color light and the second EML 970 may emit red (R), green (G), blue (B) or yellow-green (YG) color light. In one exemplary embodiment, the first EML 870 may emit blue (B) color light and the second EML 970 emit green (G), yellow-green (YG) or orange color light, each of which has a longer luminescence wavelength than the blue color light. For Example, when the second EML 970 is a yellow-green (YG) emitting material layer, the second EML 970 may include CBP as a host and Ir(2-phq)$_3$ as a dopant.

In one embodiment, at least one of the first HIL 850 and the second HIL may consist of the hole injection material, respectively. As an example, the hole injection material layer may include, but is not limited to, MTDATA, NATA, 1T-NATA, 2T-NATA, CuPc, TCTA, NPB(NPD), HAT-CN, TDAPB, PEDOT/PSS, F4TCNQ and/or N-(biphenyl-4-yl)-9,9-dimethyl-N-(4-(9-phenyl-9H-carbazol-3-yl)phenyl)-9H-fluoren-2-amine.

In another exemplary embodiment, at least one of the first HIL 850 and the second HIL may include the organic compound having the structure of Chemical Formulae 1 and 2 doped with the hole injection material. In this case, each of the first HIL 850 and the second HIL may include the hole injection material of about 0.1 to about 50% by weight. In still another exemplary embodiment, at least one of the first HIL 850 and the second HIL may be divided into a HIL disposed adjacently to the first electrode 810 or the CGL 910 and consisting of the hole injection material and another HIL disposed adjacently to the first or second HTL 860 or 960 and including the organic compound having the structure of Chemical Formulae 1 and 2 doped with the hole injection material. The first HIL 850 and the second HIL may include the same material or different materials.

At least one of the first and second HTLs 860 and 960 include the organic compound having the structure of Chemical Formulae 1 and 2. In one exemplary embodiment, at least one of the first and second HTLs 860 and 960 may consist of the organic compound having the structure of Chemical Formulae 1 and 2. In another exemplary embodiment, at least one of the first and second HTLs 860 and 960 may include the organic compound having the structure of Chemical Formulae 1 and 2 doped with other hole transport material or included the other hole transport material doped with the organic compound having the structure of Chemical Formulae 1 and 2.

The other hole transport material that may be used with the organic compound having the structure of Chemical Formulae 1 and 2 as a dopant or a host in at least one of the first and second HTLs 860 and 960 may include, but are not limited to, NPB, TCTA, TFV-TCTA, tris[4-(diethylamino)phenyl]amine, tri-p-tolylamine, N-[1,1'-biphenyl]-4-yl-9,9-diMethyl-N-[4-(9-phenyl-9H-carbazol-3-yl)phenyl]-amine, TAPC, m-MTDATA, mCP, CBP, 1,4-bis(diphenylamino)benzene, 4,4'-bis(3-ethyl-N-carbazolyl)-1,1'-biphenyl, TPD, DNTPD, Poly-TPD, TFB, DCDPA, N-(biphenyl-4-yl)-9,9-dimethyl-N-(4-(9-phenyl-9H-carbazol-3-yl)phenyl)-9H-fluoren-2-amine, N-(biphenyl-4-yl)-N-(4-(9-phenyl-9H-carbazol-3-yl)phenyl)biphenyl-4-amine, N,N'-bis(phenanthren-9-yl)-N,N'-bis(phenyl)-benzidine, CuPc, 4-(dibenzylamino)benzaldehyde-N,N-diphenylhydrazone, 4-(dimethylamino)benzaldehyde diphenylhydrazone, 2,2'-dimethyl-N,N'-di-[(1-naphthyl)-N,N'-diphenyl]-1,1'-biphenyl-4,4'-diamine, 9,9-dimethyl-N,N'-di(1-naphthyl)-N,N'-diphenyl-9H-fluorene-2,7-diamine), N,N'-di-[(1-naphthyl)-N,N'-diphenyl]-1,1'-biphenyl)-4,4'-diamine, 4-(diphenylamino)benzaldehyde diphenylhydrazone, N,N'-diphenyl-N,N'-di-p-tolylbenzene-1,4-diamine, HAT-CN6, N,N,N',N'-tetrakis(4-methoxyphenyl)benzidine, N,N,N',N'-tetrakis(3-methylphenyl)-3,3'-dimethylbenzidine, N,N,N',N'-tetrakis(2-naphthyl)benzidine, tetra-N-phenylbenzidine, N,N,N',N'-tetraphenylnaphthalene-2,6-diamine), tin(IV) 2,3-naphthalocyanine dichloride, titanyl phthalocyanine, TDAB, 1,3,5-tris(2-(9-ethylcabazyl-3)ethylene)benzene, 1,3,5-tris[(3-methylphenyl)phenylamino]benzene, 4,4',4"-tris[2-naphthyl(phenyl)amino]triphenylamine) and/or 4,4',4"-tris[phenyl(m-tolyl)amino]triphenylamine.

In an alternative embodiment, at least one of the first and second HTLs 860 and 960 may include an HTL disposed adjacently to the first HIL 850 or the second HIL and consisting of the hole transport material and another HTL disposed adjacently to the first or second EBL 875 or 975 and consisting of the organic compound having the structure of Chemical Formulae 1 and 2 or including the organic compound having the structure of Chemical Formulae 1 and 2 and the other hole transport material. The first and second HTLs 860 and 960 may include the same material or different materials.

In one exemplary embodiment, at least one of the first and second EBLs 865 and 965 may include the organic compound having the structure of Chemical Formulae 1 and 2. In another exemplary embodiment, at least one of the first and second EBLs 865 and 965 may include other electron blocking material. The other electron blocking material may include, but are not limited to, TCTA, Tris[4-(diethylamino)phenyl]amine, N-(bipnehyl-4-yl)-9,9-dimethyl-N-(4-(9-phenyl-9H-carbazol-3-yl)phenyl)-9H-fluorene-2-amine, TAPC, MTDATA, mCP, mCBP, CuPc, DNTPD, TDAPB, DCDPA, 2,8-bis(9-phneyl-9H-carbazol-3-yl)dibenzo[b,d]thiophene, and/or 3,6-bis(N-carbazolyl)-N-phenyl-carbazole. The first EBL 865 and the second EBL 965 may include the same material or different materials.

Each of the first and second ETLs 880 and 980 may include, but are not limited to, oxadiazole-based compounds, triazole-based compounds, phenanthroline-based compounds, benzoxazole-based compounds, benzothiazole-based compounds, benzimidazole-based compounds, triazine-based compounds, and the like, respectively. As an example, each of the first and second ETLs 880 and 980 may include, but are not limited to, Alq$_3$, PBD, spiro-PBD, Liq, TPBi, BAlq, Bphen, NBphen, BCP, TAZ, NTAZ, TpPyPB, TmPPPyTz, PFNBr, TPQ, TSPO1 and/or ZADN, respectively. Alternatively, each of the ETLs 580 and 680 may include the above-described organic material doped with metal such as an alkali metal and/or an alkaline earth metal, respectively. The first and second ETLs 880 and 980 may include the same material or different material.

The EIL 990 is may include, but are not limited to, an alkali halide such as LiF, CsF, NaF, BaF$_2$ and the like, and/or an organic metal compound such as lithium benzoate, sodium stearate, and the like. As an example, each of the first and second ETLs 880 and 980 and the EIL 990 may be laminated with a thickness of, but are not limited to, about 10 nm to about 200 nm, preferably about 10 nm to 100 nm.

The CGL 910 include the N-type CGL 1010 disposed adjacently to the first emitting unit 830 and the P-type CGL 1020 disposed adjacently to the second emitting unit 930. The N-type CGL 1010 injects electrons into the first emitting unit 830 and the P-type CGL 1020 injects holes into the second emitting unit 930.

As an example, the N-type CGL 1010 may be an organic layer doped with an alkali metal such as Li, Na, K and/or Cs and/or an alkaline earth metal such as Mg, Sr, Ba and/or Ra. For example, a host used in the N-type CGL 1010 may include, but are not limited to, an organic compound such as Bphen or MTDATA. The alkali metal or the alkaline earth metal may be doped by about 0.01 wt % to about 30 wt %.

The P-type CGL 1020 may include the organic compound having the structure of Chemical Formulae 1 and 2. For example, the P-type CGL 1020 may include the organic compound having the structure of Chemical Formulae 1 and 2 doped with the hole injection material. The dopant as the hole injection material in the P-type CGL 1020 may include, but are not limited to, MTDATA, NATA, 1T-NATA, 2T-NATA, CuPc, TCTA, NPB(NPD), HAT-CN, TDAPB, PEDOT/PSS, F4TCNQ and/or N-(biphenyl-4-yl)-9,9-dimethyl-N-(4-(9-phenyl-9H-carbazol-3-yl)phenyl)-9H-fluoren-2-amine. When the P-type CGL 1020 includes the organic compound having the structure of Chemical Formulae 1 and 2 and the hole injection material, the P-type CGL 1020 may include the hole injection material of, but is not limited to, about 0.1 to about 50% by weight.

As described above, the organic compound of the present disclosure shows excellent hole injection and transport properties as well as thermal stability. When the P-type CGL 1020 includes the organic compound having the structure of Chemical Formulae 1 and 2 doped with the hole injection material, the holes generated in the P-type CGL 1020 may be provided effectively into the second emitting unit 930. The tandem-structured LED 800 which includes the first and second HTLs 860 and 960, the P-type CGL 1020, the first HIL 850, the second HIL and/or the first and second EBLs 865 and 965, each of which consists of the organic compound having the structure of Chemical Formulae 1 and 2 or includes the organic compound having the structure of Chemical Formulae 1 and 2 mixed or doped with other proper hole injection material and/or hole transport material, is capable of implementing white (W) light emission at a lower driving voltage. In other words, the LED 800 can improve its luminous lifetime and luminous efficiency by using the organic compound of the present disclosure.

In FIGS. 4 and 5, each of the LEDs 500 and 800 includes first and second emitting units 530, 830, 630 and 930 and CGLs 710 and 1010 between the first and second emitting units. In another exemplary embodiment, a LED of the present disclosure may further include a third emitting unit disposed between the second emitting unit 630 or 930 and the second electrode 520 or 820 and a second CGL disposed between the second emitting unit 630 or 930 and the third emitting unit. In this case, at least one of the first emitting unit 530 or 830, the second emitting unit 630 or 930 and the third emitting unit may include the organic compound having the structure of Chemical Formulae 1 and 2.

Synthesis Example 1: Synthesis of Compound 1

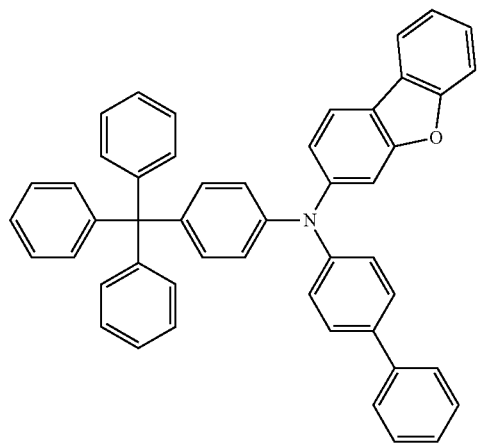

Compound 1

8.0 g (20 mmol) of Compound SM1, 6.7 g (20 mmol) of Compound SM2, 0.45 g (2 mmol) of palladium(II) acetate (Pd(OAc)$_2$), 0.81 g (4 mmol) of tri-tert-butylphosphine (P(t-Bu)$_3$) and 7.7 g (80 mmol) of sodium tert-butoxide (NaOtBu) were dissolved in 200 mL toluene within 500 mL round bottom flaks under nitrogen atmosphere, and then the solution was heating refluxed for 12 hours with stirring. Organic layer was extracted with chloroform, and then washed with water. Anhydrous MgSO$_4$ was added to remove moisture, and then the organic layer was filtered. The organic solvent was distilled under reduced pressure and removed. The crude product was purified by column chromatography to give 12.0 g (yield: 92%) of Compound 1.

Synthesis Example 2: Synthesis of Compound 5

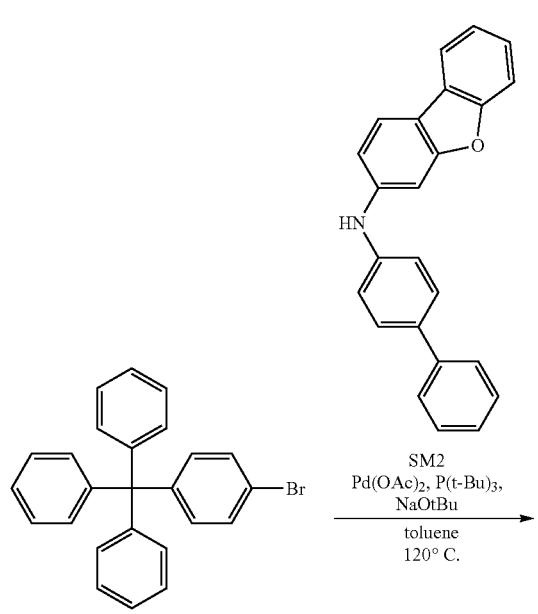

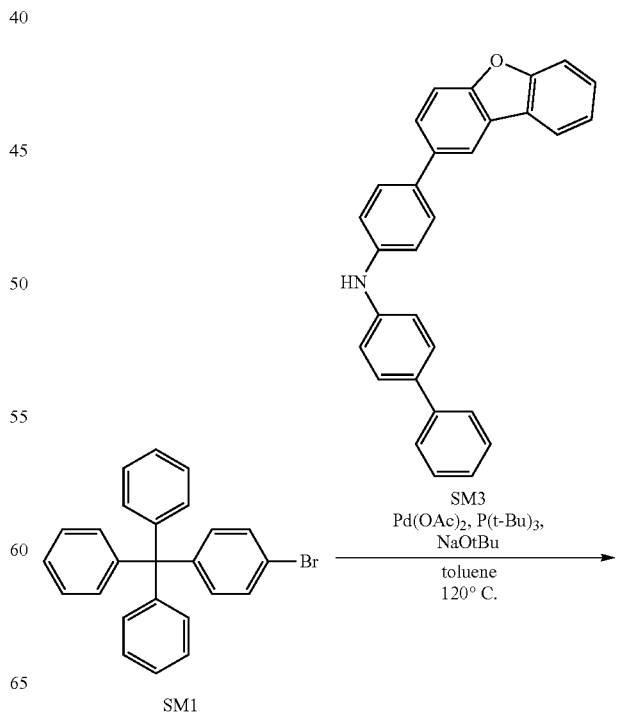

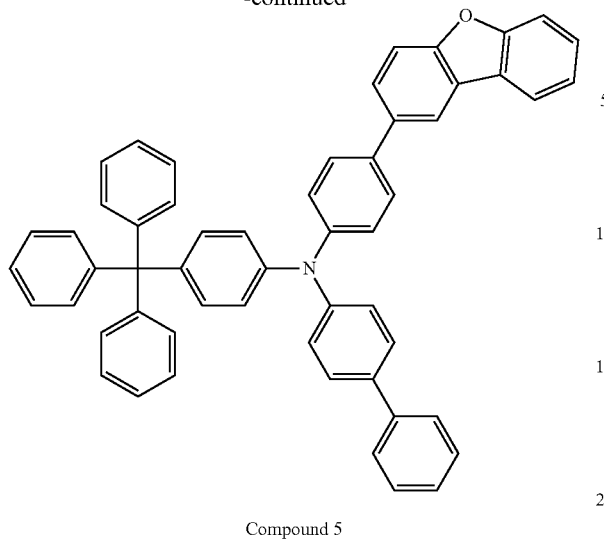

Compound 5

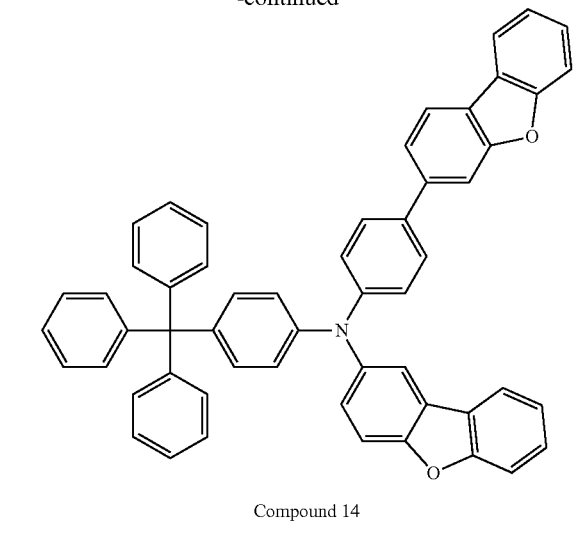

Compound 14

8.0 g (20 mmol) of Compound SM1, 8.2 g (20 mmol) of Compound SM3, 0.45 g (2 mmol) of Pd(OAc)$_2$, 0.81 g (4 mmol) of P(t-Bu)$_3$ and 7.7 g (80 mmol) of NaOtBu were dissolved in 200 mL toluene within 500 mL round bottom flaks under nitrogen atmosphere, and then the solution was heating refluxed for 12 hours with stirring. Organic layer was extracted with chloroform, and then washed with water. Anhydrous MgSO$_4$ was added to remove moisture, and then the organic layer was filtered. The organic solvent was distilled under reduced pressure and removed. The crude product was purified by column chromatography to give 13.1 g (yield: 90%) of Compound 5.

Synthesis Example 3: Synthesis of Compound 14

Here, 8.0 g (20 mmol) of Compound SM1, 8.5 g (20 mmol) of Compound SM4, 0.45 g (2 mmol) of Pd(OAc)$_2$, 0.81 g (4 mmol) of P(t-Bu)$_3$ and 7.7 g (80 mmol) of NaOtBu were dissolved in 200 mL toluene were within 500 mL round bottom flaks under nitrogen atmosphere, and then the solution was heating refluxed for 12 hours with stirring. Organic layer was extracted with chloroform, and then washed with water. Anhydrous MgSO$_4$ was added to remove moisture, and then the organic layer was filtered. The organic solvent was distilled under reduced pressure and removed. The crude product was purified by column chromatography to give 12.9 g (yield: 87%) of Compound 14.

Synthesis Example 4: Synthesis of Compound 18

(1) Synthesis of Intermediate 18-1

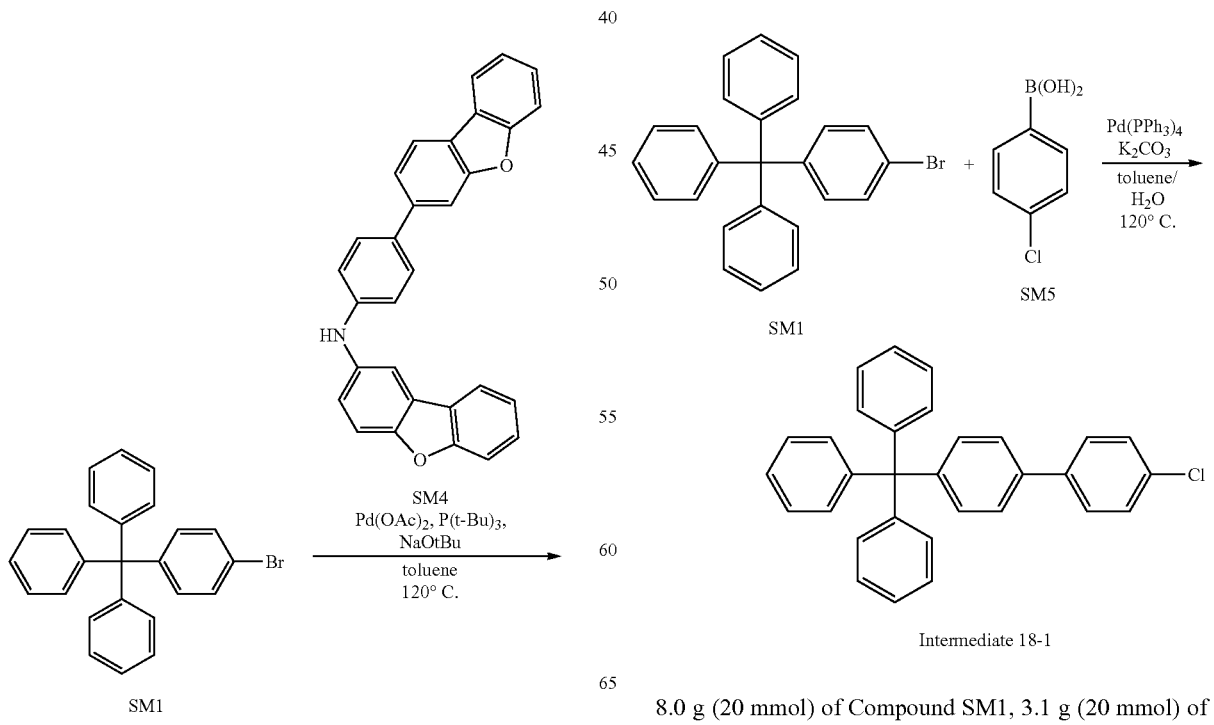

Intermediate 18-1

8.0 g (20 mmol) of Compound SM1, 3.1 g (20 mmol) of Compound SM5, 1.2 g (1 mmol) of tetrakis(triphenylphosphine) palladium(0) (Pd(PPh$_3$)$_4$) and 8.3 g (60 mmol) of K$_2$CO$_3$ were dissolved in a mixed solvent of 200 mL of toluene and 50 mL of water within 500 mL round bottom flask under nitrogen atmosphere, and then the solution was heating refluxed for 12 hours with stirring. Organic layer was extracted with chloroform, and then washed with water. Anhydrous MgSO$_4$ was added to remove moisture, and then the organic layer was filtered. The organic solvent was distilled under reduced pressure and removed. The crude product was purified by column chromatography to give 7.3 g (yield: 85%) of Intermediate 18-1.

(2) Synthesis of Compound 18

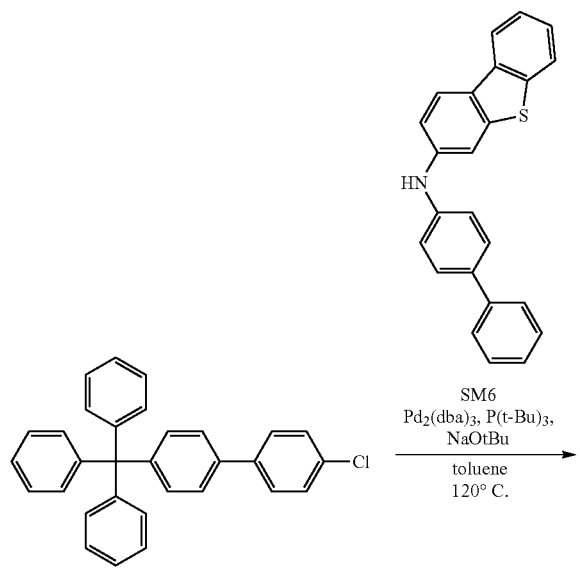

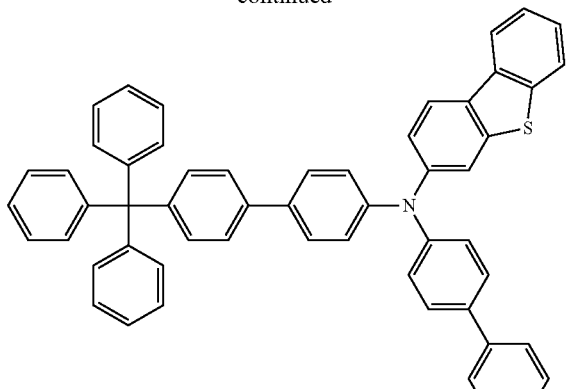

Compound 18

8.62 g (20 mmol) of Intermediate 18-1, 7.0 g (20 mmol) of Compound SM6, 1.83 g (2 mmol) of tris(dibenzylideneacetone) dipalladium(0) (Pd$_2$(dba)$_3$), 0.81 g (4 mmol) of P(t-Bu)$_3$ and 7.7 g (80 mmol) of NaOtBu were dissolved in 200 mL toluene within 500 mL round bottom flaks under nitrogen atmosphere, and then the solution was heating refluxed for 12 hours with stirring. Organic layer was extracted with chloroform, and then washed with water. Anhydrous MgSO$_4$ was added to remove moisture, and then the organic layer was filtered. The organic solvent was distilled under reduced pressure and removed. The crude product was purified by column chromatography to give 11.9 g (yield: 80%) of Compound 18.

Synthesis Example 5: Synthesis of Compound 30

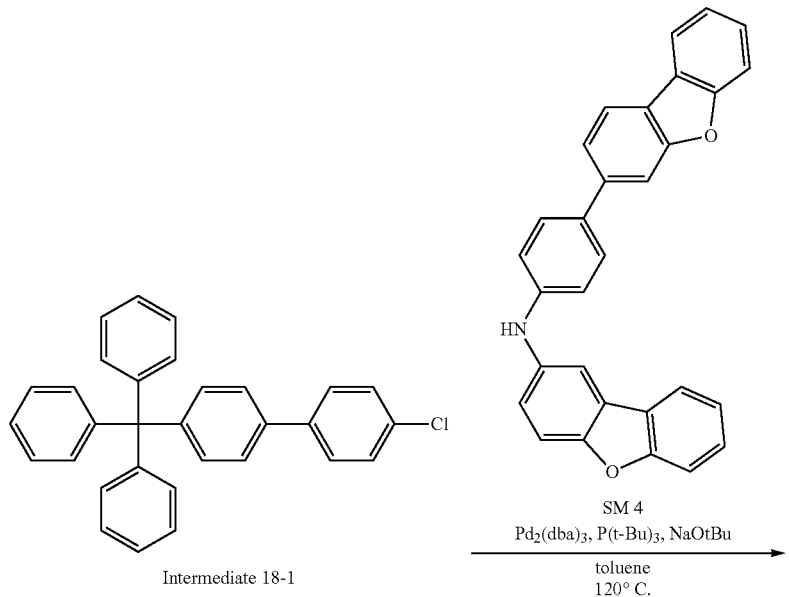

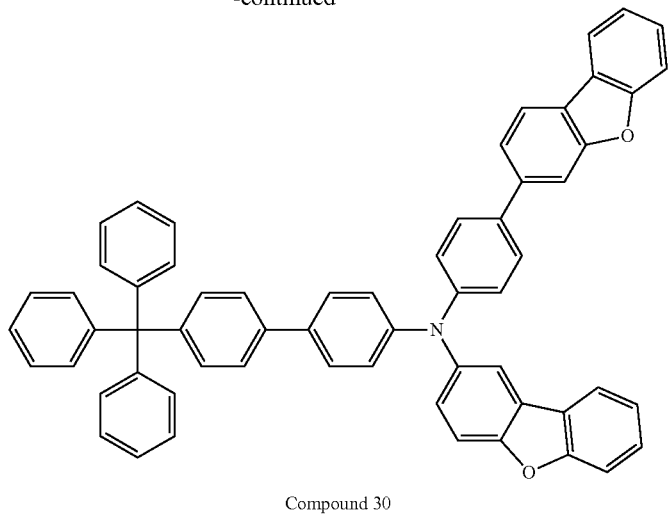

Compound 30

8.62 g (20 mmol) of Intermediate 18-1, 8.51 g (20 mmol) of Compound SM4, 1.83 g (2 mmol) of Pd$_2$(dba)$_3$, 0.81 g (4 mmol) of P(t-Bu)$_3$ and 7.7 g (80 mmol) of NaOtBu were dissolved in 200 mL toluene within 500 mL round bottom flaks under nitrogen atmosphere, and then the solution was heating refluxed for 12 hours with stirring. Organic layer was extracted with chloroform, and then washed with water. Anhydrous MgSO$_4$ was added to remove moisture, and then the organic layer was filtered. The organic solvent was distilled under reduced pressure and removed. The crude product was purified by column chromatography to give 13.6 g (yield: 83%) of Compound 30.

Synthesis Example 6: Synthesis of Compound 33

(1) Synthesis of Intermediate 33-1

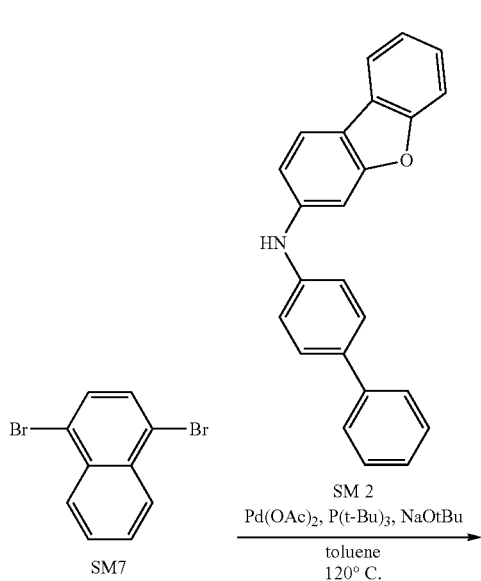

SM7 + SM 2 →(Pd(OAc)$_2$, P(t-Bu)$_3$, NaOtBu, toluene, 120° C.)

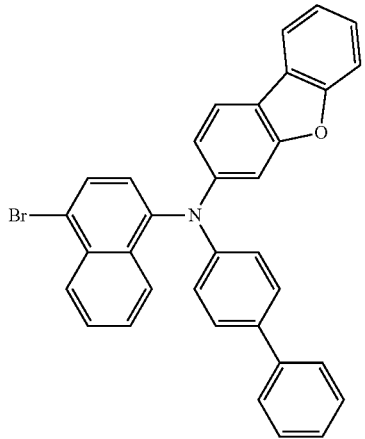

Intermediate 33-1

5.7 g (20 mmol) of Compound SM7, 6.7 g (20 mmol) of Compound SM2, 0.45 g (2 mmol) of Pd(OAc)$_2$, 0.81 g (4 mmol) of P(t-Bu)$_3$ and 7.7 g (80 mmol) of NaOtBu were dissolved in 200 mL of toluene within 500 mL round bottom flask under nitrogen atmosphere, and then the solution was heating refluxed for 12 hours with stirring. Organic layer was extracted with chloroform, and then washed with water. Anhydrous MgSO$_4$ was added to remove moisture, and then the organic layer was filtered. The organic solvent was distilled under reduced pressure and removed. The crude product was purified by column chromatography to give 8.1 g (yield: 75%) of Intermediate 33-1.

(2) Synthesis of Intermediate 33-2

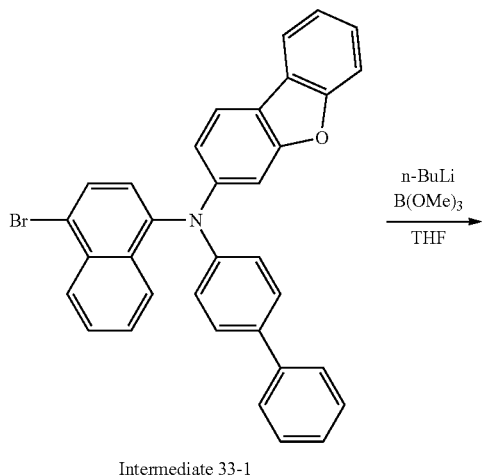

Intermediate 33-1

(3) Synthesis of Compound 33

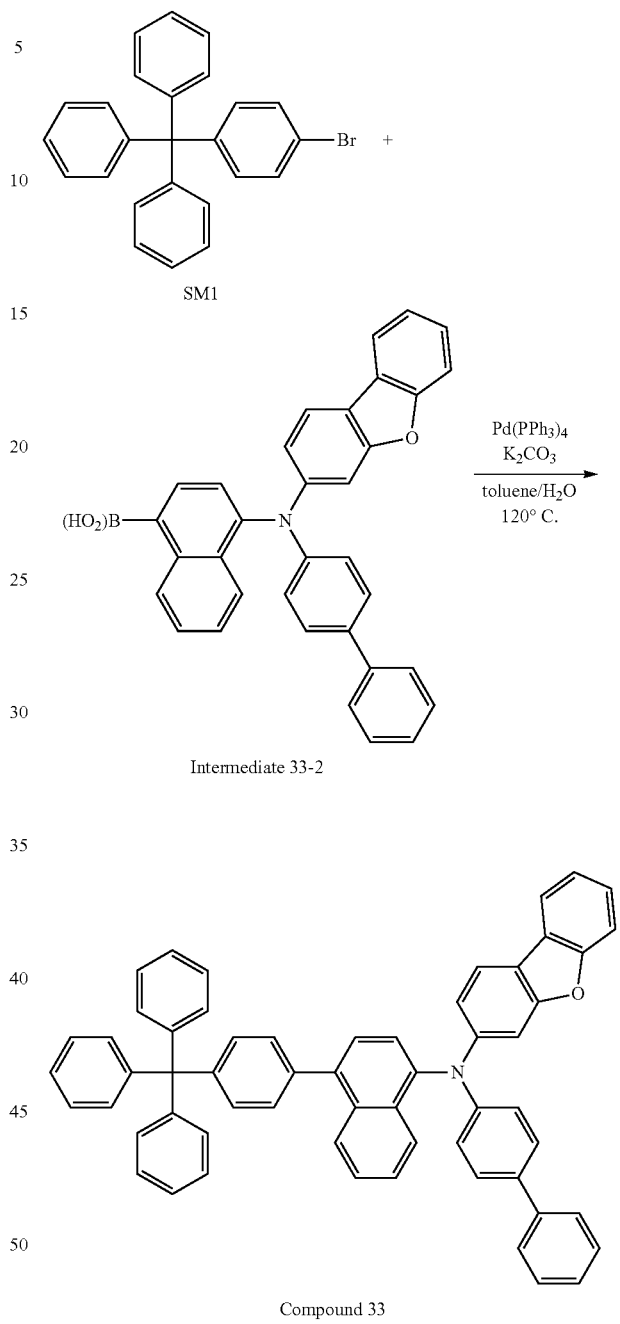

10.8 g (20 mmol) of Intermediate 33-1 were dissolved in 200 mL of THF within 500 mL round bottom flask under nitrogen atmosphere, and then the solution was cooled down to −78° C. 8 mL of 2.5 M n-BuLi was added to the solution drop wisely, the solution was stirred for 30 minutes, 3.1 g (30 mmol) of trimethyl borate (B(OMe)$_3$) was added to the solution, the solution was raised to room temperature followed by stirring for three hours. Organic layer was extracted with chloroform, and then washed with water. Anhydrous MgSO$_4$ was added to remove moisture, and then the organic layer was filtered. The organic solvent was distilled under reduced pressure and removed. The crude product was purified by column chromatography to give 8.6 g (yield: 85%) of Intermediate 33-2.

8.0 g (20 mmol) of Compound SM1, 10.1 g (20 mmol) of Intermediate 33-2, 1.2 g (1 mmol) of Pd(PPh$_3$)$_4$ and 8.3 g (60 mmol) of K$_2$CO$_3$ were dissolved in a mixed solvent of 200 mL of toluene and 50 mL of water within 500 mL round bottom flaks under nitrogen atmosphere, and then the solution was heating refluxed for 12 hours with stirring. Organic layer was extracted with chloroform, and then washed with water. Anhydrous MgSO$_4$ was added to remove moisture, and then the organic layer was filtered. The organic solvent was distilled under reduced pressure and removed. The crude product was purified by column chromatography to give 13.7 g (yield: 88%) of Compound 33.

Synthesis Example 7: Synthesis of Compound 45

(1) Synthesis of Intermediate 45-1

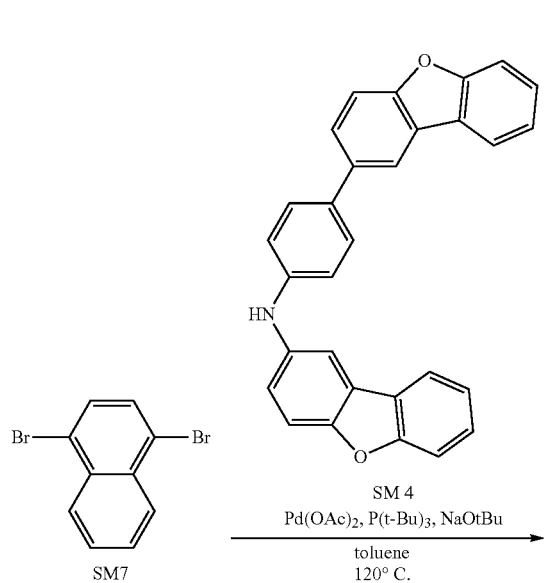

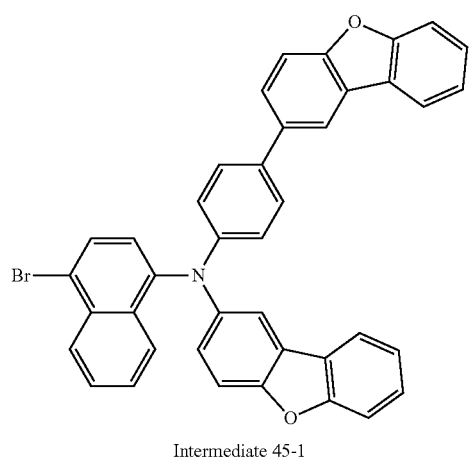

Intermediate 45-1

5.7 g (20 mmol) of Compound SM7, 8.5 g (20 mmol) of Compound SM4, 0.45 g (2 mmol) of Pd(OAc)$_2$ and 0.81 g (4 mmol) of P(t-Bu)$_3$, and 7.7 g (80 mmol) of NaOtBu were dissolved in 200 mL of toluene within 500 mL round bottom flask under nitrogen atmosphere, and then the solution was heating refluxed for 12 hours with stirring. Organic layer was extracted with chloroform, and then washed with water. Anhydrous MgSO4 was added to remove moisture, and then the organic layer was filtered. The organic solvent was distilled under reduced pressure and removed. The crude product was purified by column chromatography to give 9.8 g (yield: 78%) of intermediate 45-1.

(2) Synthesis of Intermediate 45-2

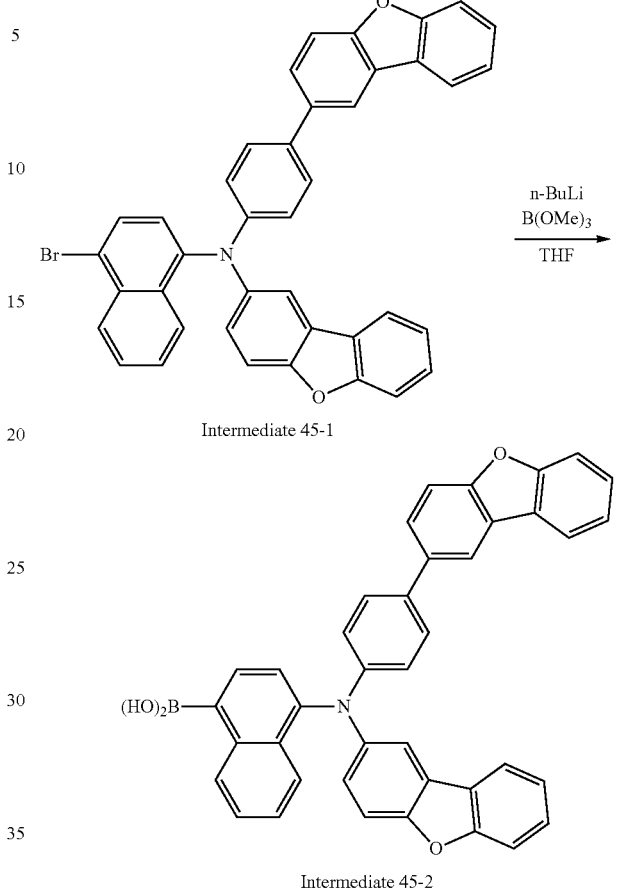

Intermediate 45-2

12.6 g (20 mmol) of Intermediate 45-1 was dissolved in 200 mL of THF within 500 mL round bottom flask under nitrogen atmosphere, and then the solution was cooled down to −78° C. 8 mL of 2.5 M n-BuLi was added to the solution drop wisely, the solution was stirred for 30 minutes, 3.1 g (30 mmol) of B(OMe)$_3$ was added to the solution, the solution was raised to room temperature followed by stirring for three hours. Organic layer was extracted with chloroform, and then washed with water. Anhydrous MgSO$_4$ was added to remove moisture, and then the organic layer was filtered. The organic solvent was distilled under reduced pressure and removed. The crud product was purified by column chromatography to give 10.8 g (yield: 91%) of intermediate 43-2.

(3) Synthesis of Compound 45

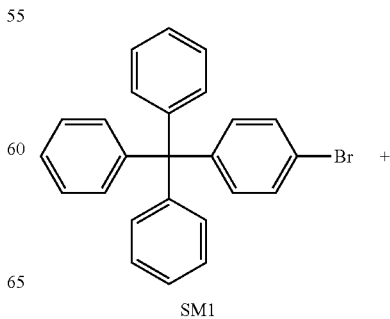

SM1

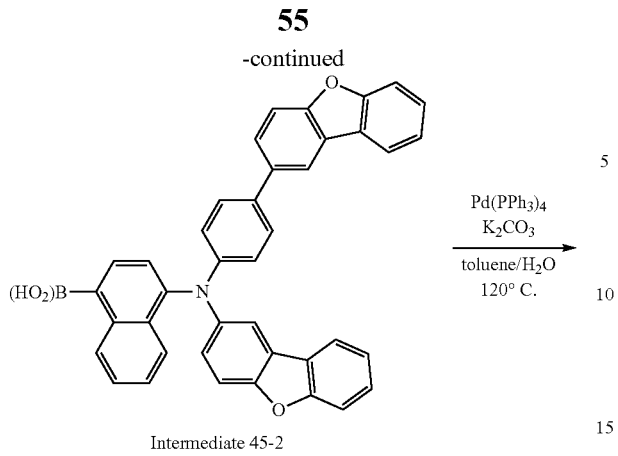

Intermediate 45-2

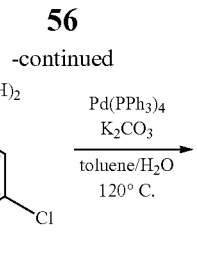

SM8

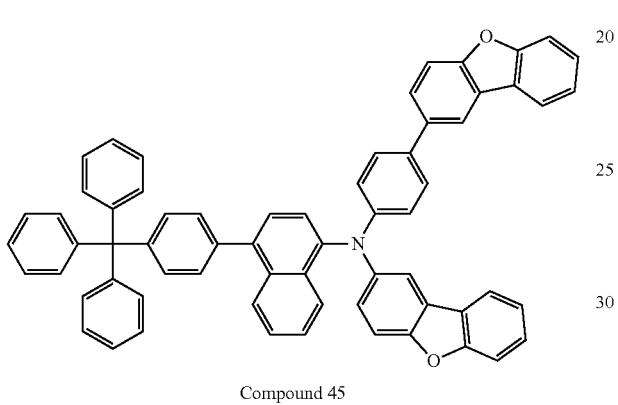

Compound 45

8.0 g (20 mmol) of Compound SM1, 11.9 g (20 mmol) of intermediate 45-2, 1.2 g (1 mmol) of Pd(PPh$_3$)$_4$ and 8.3 g (60 mmol) of K$_2$CO$_3$ were dissolved in a mixed solvent of 200 mL of toluene and 50 mL of water within 500 mL round bottom flaks under nitrogen atmosphere, and then the solution was heating refluxed for 12 hours with stirring. Organic layer was extracted with chloroform, and then washed with water. Anhydrous MgSO$_4$ was added to remove moisture, and then the organic layer was filtered. The organic solvent was distilled under reduced pressure and removed. The crude product was purified by column chromatography to give 15.3 g (yield: 88%) of Compound 45.

Synthesis Example 8: Synthesis of Compound 51

(1) Synthesis of Intermediate 51-1

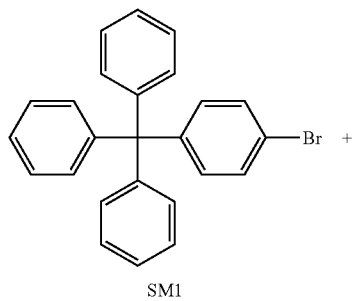

SM1

Compound 51-1

8.0 g (20 mmol) of Compound SM1, 3.1 g (20 mmol) of Compound SMB, 1.2 g (1 mmol) of Pd(PPh$_3$)$_4$ and 8.3 g (60 mmol) of K$_2$CO$_3$ were dissolved in a mixed solvent of 200 mL of toluene and 50 mL of water within 500 mL round bottom flaks under nitrogen atmosphere, and then the solution was heating refluxed for 12 hours with stirring. Organic layer was extracted with chloroform, and then washed with water. Anhydrous MgSO$_4$ was added to remove moisture, and then the organic layer was filtered. The organic solvent was distilled under reduced pressure and removed. The crude product was purified by column chromatography to give 7.0 g (yield: 81%) of Intermediate 51-1.

(2) Synthesis of Compound 51

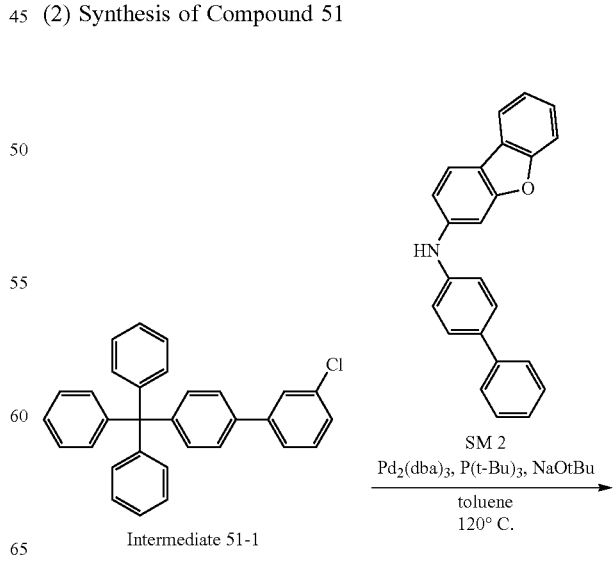

Intermediate 51-1

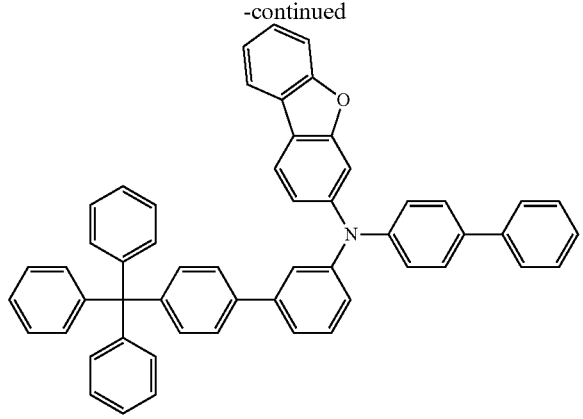

Compound 51

8.62 g (20 mmol) of Intermediate 51-1, 6.7 g (20 mmol) of Compound SM2, 1.83 g (2 mmol) of $Pd_2(dba)_3$, 0.81 g (4 mmol) of $P(t-Bu)_3$ and 7.7 g (80 mmol) of NaOtBu were dissolved in 200 mL of toluene within 500 mL round bottom flask under nitrogen atmosphere, and then the solution was heating refluxed for 12 hours with stirring. Organic layer was extracted with chloroform, and then washed with water. Anhydrous $MgSO_4$ was added to remove moisture, and then the organic layer was filtered. The organic solvent was distilled under reduced pressure and removed. The crude product was purified by column chromatography to give 13.1 g (yield: 90%) of Compound 51.

Synthesis Example 9: Synthesis of Compound 62

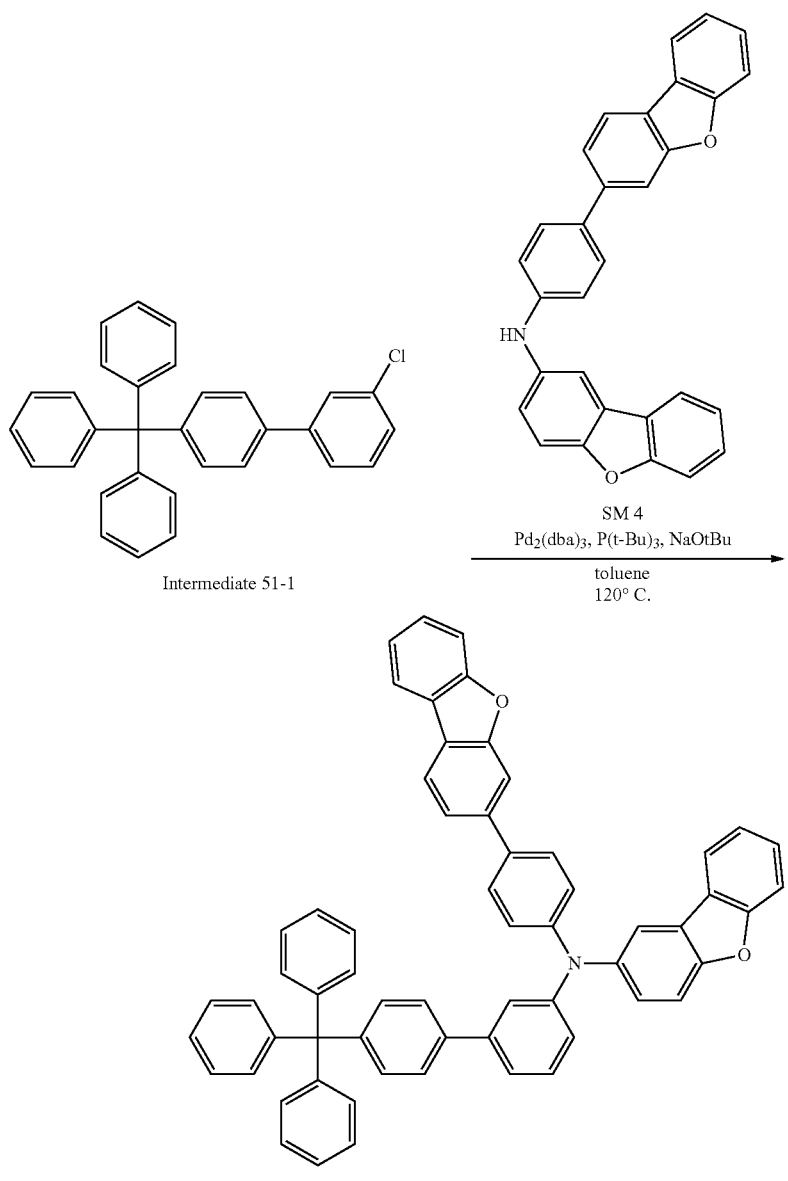

Compound 62

8.62 g (20 mmol) of Intermediate 51-1, 8.51 g (20 mmol) of Compound SM2, 1.83 g (2 mmol) of Pd(dba)$_3$, 0.81 g (4 mmol) of P(t-Bu)$_3$ and 7.7 g (80 mmol) of NaOtBu were dissolved in 200 mL of toluene within 500 mL round bottom flask under nitrogen atmosphere, and then the solution was heating refluxed for 12 hours with stirring. Organic layer was extracted with chloroform, and then washed with water. Anhydrous MgSO$_4$ was added to remove moisture, and then the organic layer was filtered. The organic solvent was distilled under reduced pressure and removed. The crude product was purified by column chromatography to give 15.3 g (yield: 93%) of Compound 62.

Synthesis Example 10: Synthesis of Compound 11

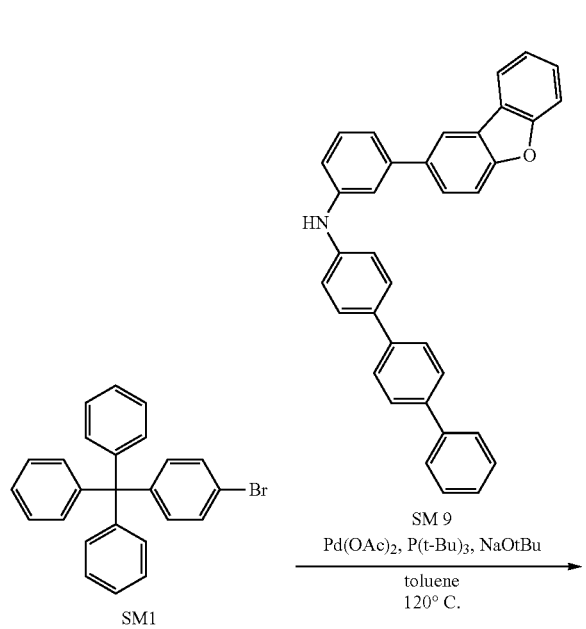

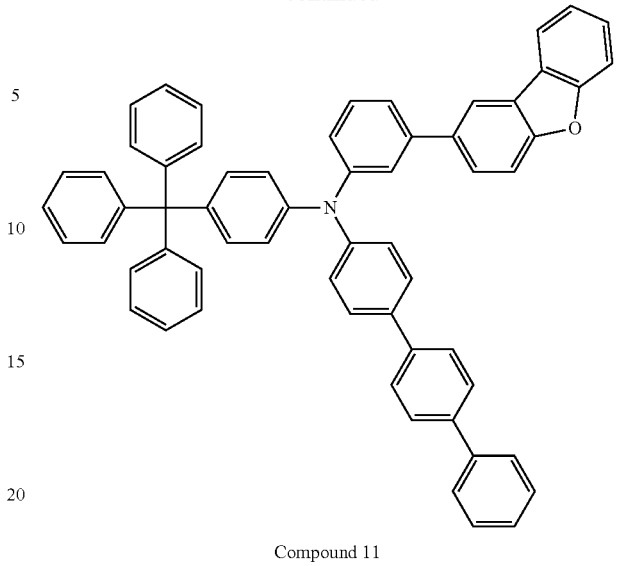

Compound 11

8.0 g (20 mmol) of Compound SM1, 9.8 g (20 mmol) of Compound SM9, 0.45 g (2 mmol) of Pd(OAc)$_2$, 0.81 g (4 mmol) of P(t-Bu)$_3$ and 7.7 g (80 mmol) of NaOtBu were dissolved in 200 mL of toluene within 500 mL round bottom flask under nitrogen atmosphere, and then the solution was heating refluxed for 12 hours with stirring. Organic layer was extracted with chloroform, and then washed with water. Anhydrous MgSO$_4$ was added to remove moisture, and then the organic layer was filtered. The organic solvent was distilled under reduced pressure and removed. The crude product was purified by column chromatography to give 12.9 g (yield: 80%) of Compound 11.

Synthesis Example 11: Synthesis of Compound 32

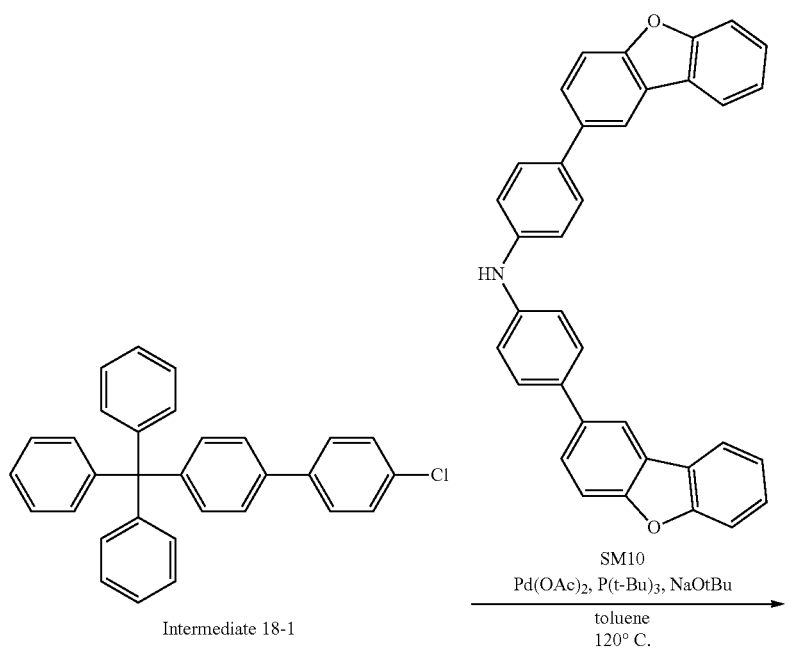

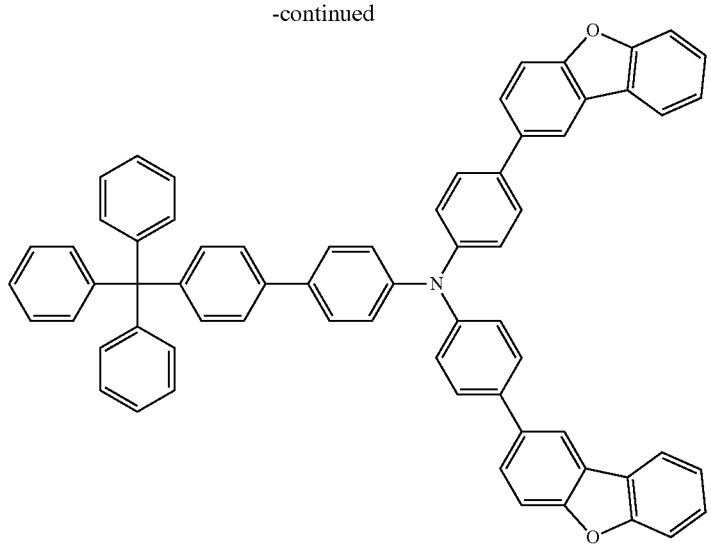

Compound 32

8.62 g (20 mmol) of Intermediate 18-1, 10.0 g (20 mmol) of Compound SM10, 0.45 g (2 mmol) of Pd(OAc)$_2$, 0.81 g (4 mmol) of P(t-Bu)$_3$ and 7.7 g (80 mmol) of NaOtBu were dissolved in 200 mL of toluene within 500 mL round bottom flask under nitrogen atmosphere, and then the solution was heating refluxed for 12 hours with stirring. Organic layer was extracted with chloroform, and then washed with water. Anhydrous MgSO$_4$ was added to remove moisture, and then the organic layer was filtered. The organic solvent was distilled under reduced pressure and removed. The crude product was purified by column chromatography to give 12.5 g (yield: 70%) of Compound 32.

Synthesis Example 12: Synthesis of Compound 48

(1) Synthesis of Intermediate 48-1

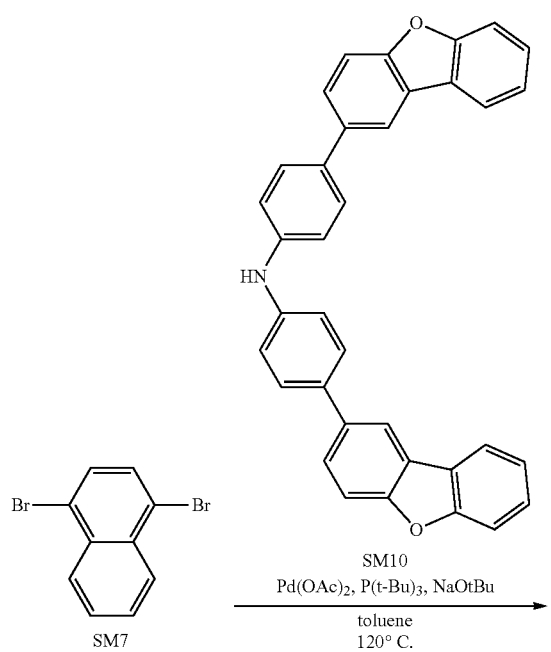

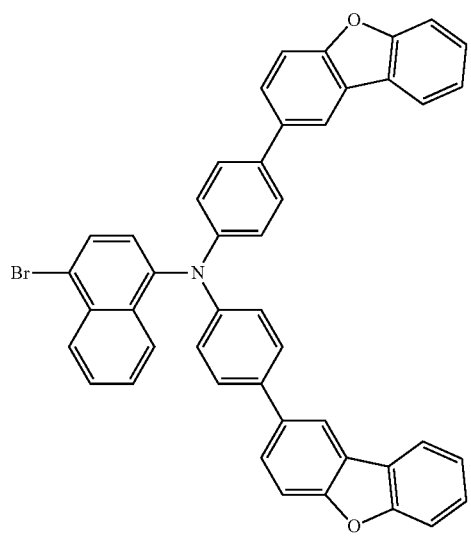

Intermediate 48-1

5.7 g (20 mmol) of Compound SM7, 10.0 g (20 mmol) of Compound SM10, 0.45 g (2 mmol) of Pd(OAc)$_2$, 0.81 g (4 mmol) of P(t-Bu)$_3$ and 7.7 g (80 mmol) of NaOtBu were dissolved in 200 mL of toluene within 500 mL round bottom flask under nitrogen atmosphere, and then the solution was heating refluxed for 12 hours with stirring. Organic layer was extracted with chloroform, and then washed with water. Anhydrous MgSO$_4$ was added to remove moisture, and then the organic layer was filtered. The organic solvent was distilled under reduced pressure and removed. The crude product was purified by column chromatography to give 9.5 g (yield: 68%) of Intermediate 48-1.

(2) Synthesis of Intermediate 48-2

(3) Synthesis of Compound 48

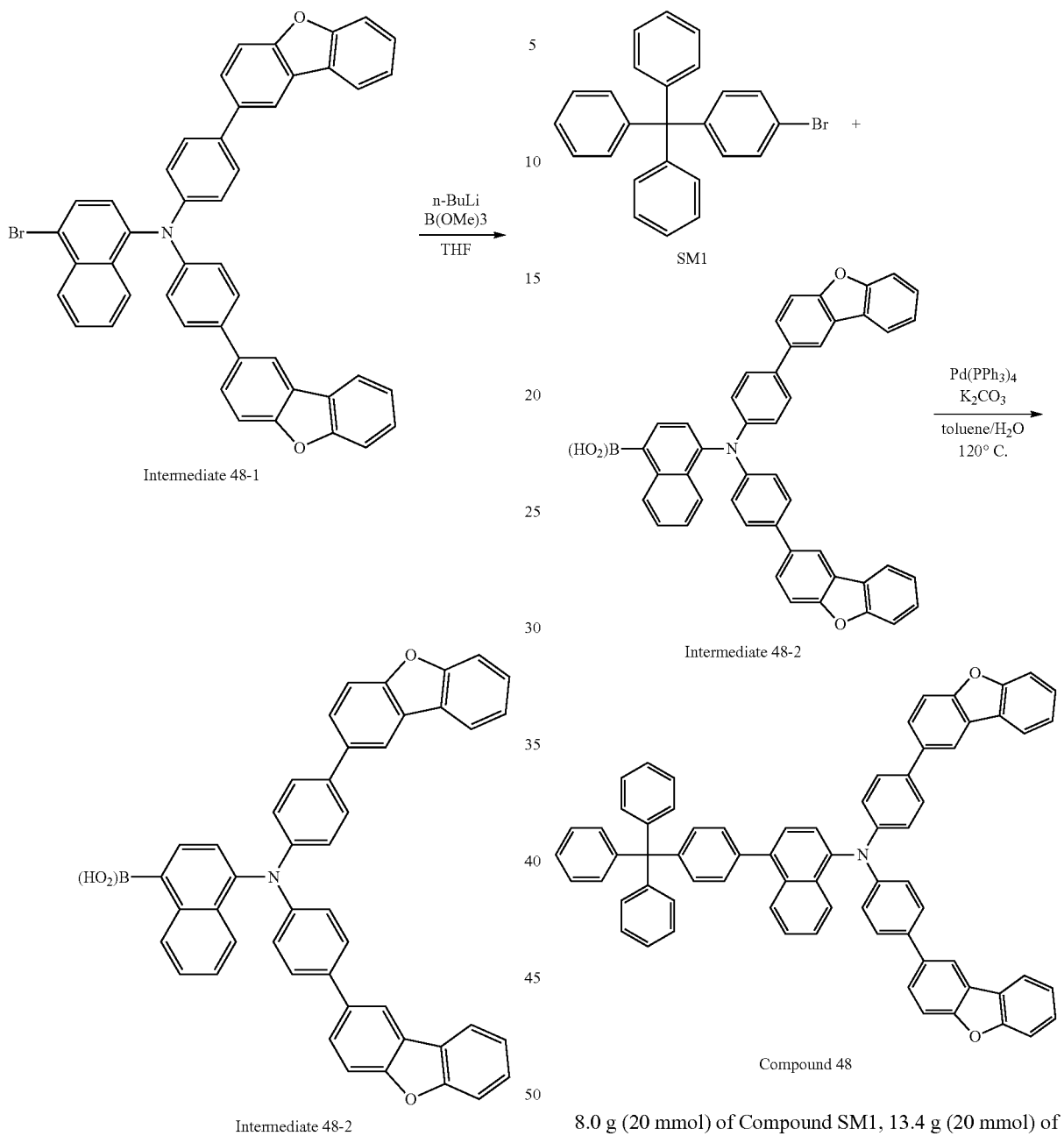

14.1 g (20 mmol) of Intermediate 48-1 was dissolved in 200 mL of THF within 500 mL round bottom flask under nitrogen atmosphere, and then the solution was cooled down to −78° C. 8 mL of 2.5 M n-BuLi was added to the solution drop wisely, the solution was stirred for 30 minutes, 3.1 g (30 mmol) of B(OMe)$_3$ was added to the solution, the solution was raised to room temperature followed by stirring for three hours. Organic layer was extracted with chloroform, and then washed with water. Anhydrous MgSO$_4$ was added to remove moisture, and then the organic layer was filtered. The organic solvent was distilled under reduced pressure and removed. The crude product was purified by column chromatography to give 10.7 g (yield: 80%) of intermediate 48-2.

8.0 g (20 mmol) of Compound SM1, 13.4 g (20 mmol) of Intermediate 48-2, 1.2 g (1 mmol) of Pd(PPh$_3$)$_4$ and 8.3 g (60 mmol) of K$_2$CO$_3$ were dissolved in a mixed solvent of 200 mL of toluene and 50 mL of water within 500 mL round bottom flask under nitrogen atmosphere, and then the solution was heating refluxed for 12 hours with stirring. Organic layer was extracted with chloroform, and then washed with water. Anhydrous MgSO$_4$ was added to remove moisture, and then the organic layer was filtered. The organic solvent was distilled under reduced pressure and removed. The crude product was purified by column chromatography to give 15.1 g (yield: 80%) of Compound 48.

Experimental Example 1: Measurement of Energy Level

HOMO energy level, LUMO energy level, excited state singlet energy level S$_1$ and excited state triplet energy level T₁ for the Compounds synthesized in the Synthesis Examples 6, 11 and 12 were measured by simulation test. The measurement results are indicated in the following Table 1.

TABLE 1

Energy Level of Compounds

| Compound | HOMO*(eV) | LUMO*(eV) | S₁(eV) | T₁*(eV) |
|---|---|---|---|---|
| 33 | −4.91 | −1.28 | 3.05 | 2.42 |
| 32 | −4.90 | −1.29 | 3.04 | 2.42 |
| 48 | −4.87 | −0.98 | 3.19 | 2.76 |

*HOMO: Film (100 nm/ITO) by AC3;
*LUMO: calculated from Film absorption edge;
*T₁: Calculated by Gaussian ED-DFT(time-dependent density functional theory), solution (toluene) by FP-8600.

As indicated by Table 1, it was confirmed that each of the compounds synthesized in the Synthesis Examples 6, 11 and 12 has a proper HOMO energy level, a LUMO energy level, an excited singlet and triplet energy levels $S_1$ and $T_1$ for a charge control layer such as a hole transport layer and/or an electron blocking layer. A light emitting diode capable of driving at a lower voltage and having improved luminous efficiency and luminous lifetime is formed by applying each of these compounds into the charge control layer such as the hole transport layer and/or the electron blocking layer.

Example 1: Fabrication of Organic Light Emitting Diode (OLED)

An organic light emitting diode was fabricated applying the Compound 1 synthesized in the Synthesis Example 1 into a hole transport layer (HTL). A glass substrate onto which ITO was coated as a thin film with a thickness 1000 Å was washed and ultrasonically cleaned by solvent such as isopropyl alcohol, acetone and methanol, and dried. After cleaning the substrate, the substrate was treated with $O_2$ plasma under vacuum for 2 minutes and then transferred to a vacuum chamber for depositing emission layer.

Subsequently, an emission layer and a cathode were deposited with setting the deposition ratio of 1 Å/s under $10^{-7}$ Torr as the following order:

a hole injection layer (HIL) (HI-1; 60 nm); a hole transport layer (HTL) (Compound 1, 80 nm); an emitting material layer (EML) (BH-1 (9-(2-naphtyl)-10-[3-(2-naphthyl)phenyl]anthracene) (blue host): BD-1 (3,8-bis(diphenylamino) pyrene) (blue dopant)=95:5 by weight ratio; 30 nm); an electron transport layer (ETL)-an electron injectin layer (EIL) (ET-1 (2-[4-(9,10-di-2-naphthalenyl-2-anthracenyl) phenyl]-1-phenyl-1H-benzimdiazole: Liq=1:1 by weight ratio; 30 nm); and a cathode (Al; 100 nm).

And then, cappling layer (CPL) was deposited over the cathode and the device was encapsualted by glass. After deposition of emissve layer and the cathode, the LED was transferred from the deposition chamber to a dry box for film formation, followed by encapsulation using UV-curable epoxy and moisture getter. The manufacture organic light emitting diode had an emission area of 9 mm². The chemical structures of the materials used in the LED is indicated in the following Chemical Formula:

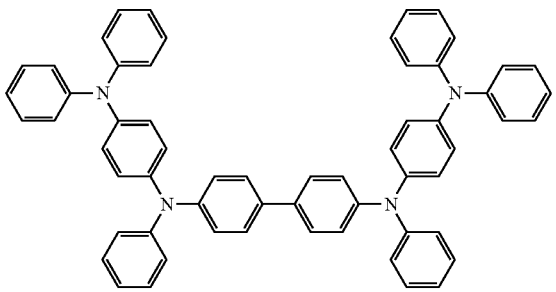

HI-1

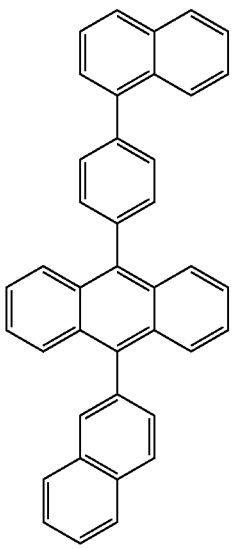

BH-1

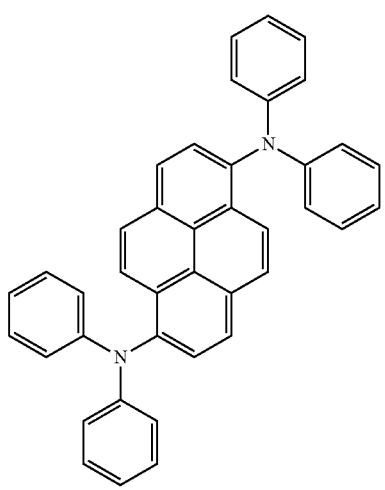

BD-1

ET-1

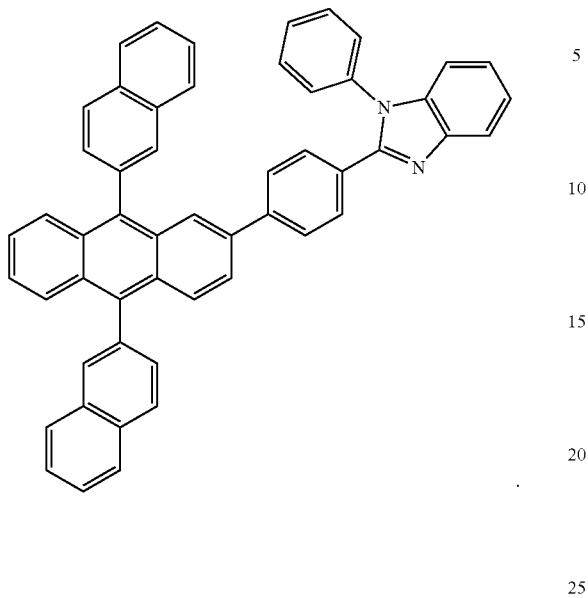

HTL-1

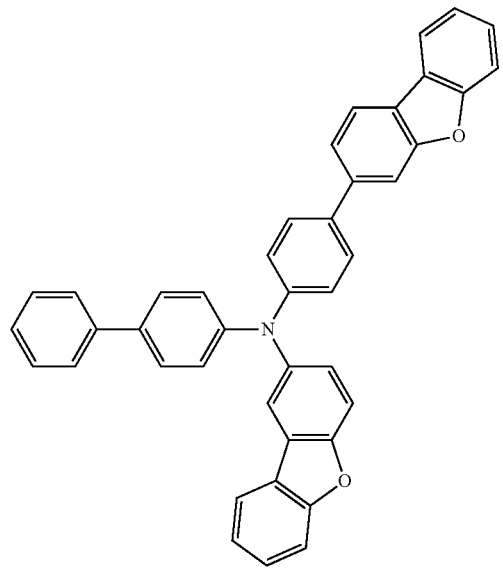

Examples 2~9: Fabrication of OLEDs

An organic light emitting diode was fabricated as the same process and the same materials as in Example 1, except that Compound 5 (Example 2) synthesized in the Synthesis Example 2, Compound 14 (Example 3) synthesized in the Synthesis Example 3, Compound 18 (Example 4) synthesized in the Synthesis Example 4, Compound 30 (Example 5) synthesized in the Synthesis Example 5, Compound 32 (Example 6) synthesized in the Synthesis Example 6, Compound 45 (Example 7) synthesized in the Synthesis Example 7, Compound 51 (Example 8) synthesized in the Synthesis Example 8 or Compound 62 (Example 9) synthesized in the Synthesis Example 9 was used as the material in the HTL in place of the Compound 1.

HTL-2

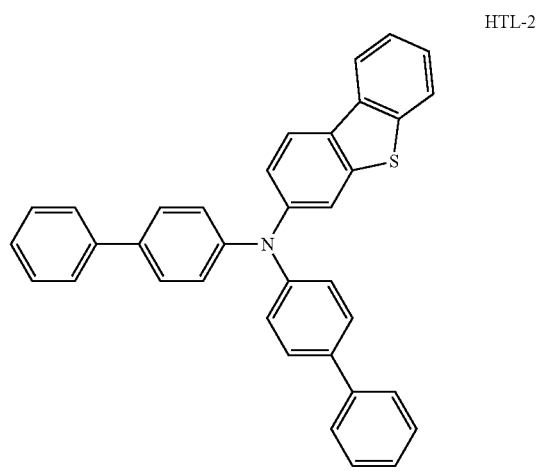

Comparative Examples 1~7: Fabrication of OLED

An organic light emitting diode was fabricated by the same process and the same materials as in Example 1, except that NPB(Comparative Example 1; Ref. 1), HTL-1 (Comparative Example 2; Ref. 2), HTL-2 (Comparative Example 3; Ref. 3), HTL-3 (Comparative Example 4, Ref. 4), HTL-4 (Comparative Example 5; Ref. 5), HTL-5 (Comparative Example 6; Ref. 6) or HTL-6 (Comparative Example 7; Ref. 7) was used as the material in the HTL in place of the Compound 1. The chemical structure of HTL-1 to HTL-6 used in the HTL is indicted in the following Chemical Formula:

HTL-3

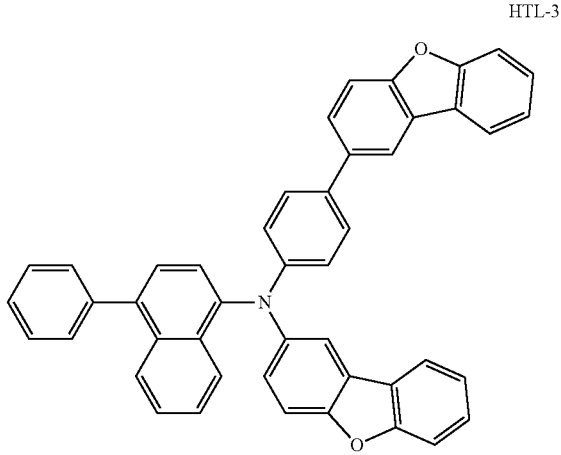

-continued

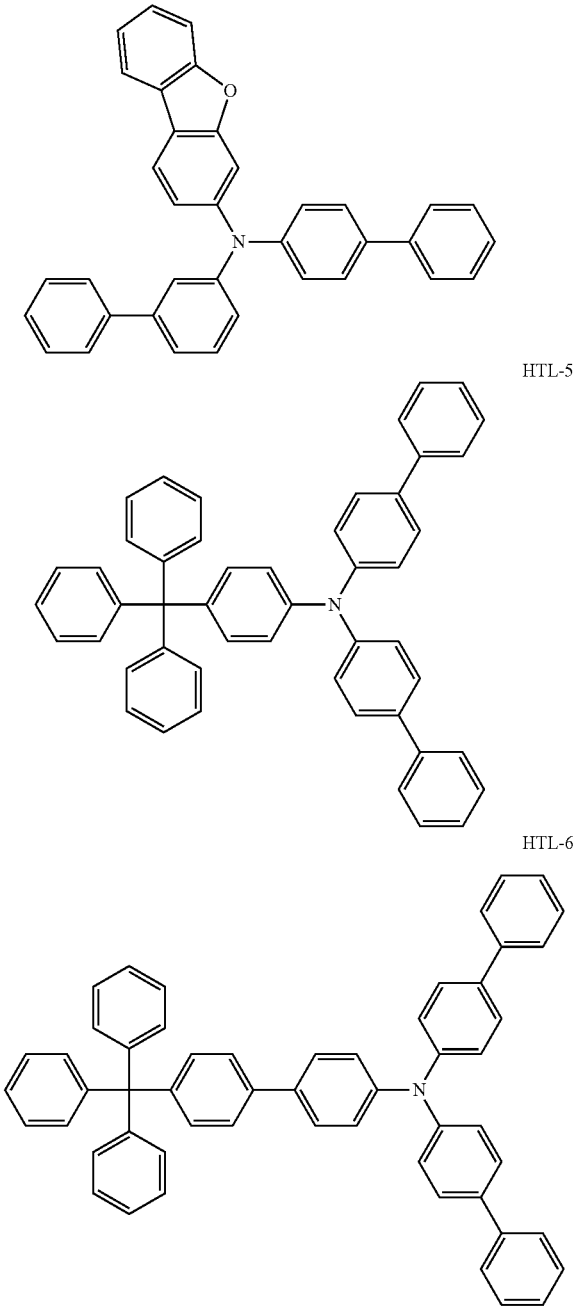

HTL-4

HTL-5

HTL-6

Experimental Example 2: Measurement of Luminous Properties of OLED

Each of the OLEDs fabricated in Examples 1 to 9 and Comparative Examples 1 to 7 was connected to an external power source and then luminous properties for all the diodes were evaluated using a constant current source (KEITHLEY) and a photometer PR650 at room temperature. In particular, driving voltage (V), current efficiency (Cd/A) and color coordinates at a current density of 10 mA/cm$^2$ and time period ($T_{95}$) at which the luminance was reduced to 95% at 3000 nit of the OLEDs in Examples 1 to 9 and Comparative Examples 1 to 7 were measured. The measurement results are indicated in the following Table 2.

TABLE 2

| Sample | Luminous Properties of OLED | | | | |
|---|---|---|---|---|---|
| | V | cd/A | CIE(x) | CIE(y) | $T_{95}$ |
| Ref. 1 | 4.64 | 100% | 0.141 | 0.110 | 100% |
| Ref. 2 | 4.43 | 108% | 0.141 | 0.112 | 104% |
| Ref. 3 | 4.51 | 107% | 0.140 | 0.110 | 108% |
| Ref. 4 | 4.39 | 110% | 0.139 | 0.111 | 109% |
| Ref. 5 | 4.48 | 108% | 0.140 | 0.110 | 105% |
| Ref. 6 | 4.50 | 109% | 0.140 | 0.112 | 103% |
| Ref. 7 | 4.42 | 107% | 0.141 | 0.110 | 105% |
| Example 1 | 4.25 | 119% | 0.141 | 0.112 | 107% |
| Example 2 | 4.21 | 117% | 0.140 | 0.113 | 110% |
| Example 3 | 4.17 | 124% | 0.139 | 0.110 | 128% |
| Example 4 | 4.19 | 122% | 0.140 | 0.109 | 135% |
| Example 5 | 4.11 | 129% | 0.140 | 0.110 | 124% |
| Example 6 | 4.16 | 126% | 0.141 | 0.111 | 121% |
| Example 7 | 4.05 | 119% | 0.141 | 0.111 | 127% |
| Example 8 | 4.14 | 124% | 0.140 | 0.110 | 111% |
| Example 9 | 4.09 | 135% | 0.141 | 0.111 | 114% |

As indicated in Table 2, compared to the OLED using NPB as the HTL material in the Ref. 1, the OLEDs using the Compound as the HTL material in the Examples lowered their driving voltage up to 12.7%, and enhanced their current efficiency up to 29% and their luminous lifetime ($T_{95}$) up to 35%. It was confirmed that the OLED introducing the organic compound in a hole transfer layer can lower its driving voltage as well as enhance its luminous efficiency and its luminous lifetime.

Example 10: Fabrication of OLED

An organic light emitting diode was fabricated applying the Compound 11 synthesized in the Synthesis Example 10 into an electron blocking layer (EBL). The OLED was fabricated as the same process and the same materials as in Example 1, except that NPB was used as the material in the HTL in place of the Compound 1 and an EBL (Compound 11; 10 nm) between the HTL and the EML was additionally deposited by thermal deposition process.

Examples 11~12: Fabrication of OLEDs

An organic light emitting diode was fabricated as the same process and the same materials as in Example 10, except that Compound 32 (Example 11) synthesized in the Synthesis Example 11 or Compound 48 (Example 12) synthesized in the Synthesis Example 12 was used as the material in the EBL in place of the Compound 11.

Comparative Example 8: Fabrication of OLED

An organic light emitting diode was fabricated as the same process and the same material as in Example 10, except that TCTA (Ref. 8) was used as the material in the EBL in place of the Compound 11.

Experimental Example 3: Measurement of Luminous Properties of OLED

Luminous properties for each of the organic light emitting diodes fabricated in Examples 10~12 and Comparative Example 8 were evaluated as the same process as Experimental Example 2. The measurement results are indicated in the following Table 3:

TABLE 3

| Sample | V | cd/A | CIE(x) | CIE(y) | $T_{95}$ |
|---|---|---|---|---|---|
| Ref. 8 | 4.64 | 100% | 0.141 | 0.110 | 100% |
| Example 10 | 4.09 | 107% | 0.140 | 0.111 | 118% |
| Example 11 | 4.17 | 110% | 0.140 | 0.110 | 124% |
| Example 12 | 4.22 | 119% | 0.141 | 0.110 | 127% |

As indicated in Table 3, compared to the OLED using TCTA as the EBL material in the Ref. 8, the OLEDs using the Compounds as the EBL material in the Examples lowered their driving voltage up to 11.9%, and enhanced their current efficiency up to 19% and their luminous lifetime ($T_{95}$) up to 27%. It was confirmed that the OLED introducing the organic compound in an electron blocking layer can lower its driving voltage as well as enhance its luminous efficiency and its luminous lifetime.

From those result in the Experimental Examples 2 and 3, it was confirmed that an organic light emitting diode and an organic light emitting device such as an organic light emitting display device and an organic light emitting illumination device introducing the organic compounds into a hole transfer layer and/or an electron blocking layer can lower its driving voltage and improve its luminous efficiency and luminous lifetime.

While the present disclosure has been described with reference to exemplary embodiments and examples, these embodiments and examples are not intended to limit the scope of the present disclosure. Rather, it will be apparent to those skilled in the art that various modifications and variations can be made in the present disclosure without departing from the spirit or scope of the invention. Thus, it is intended that the present disclosure cover the modifications and variations of the present disclosure provided they come within the scope of the appended claims and their equivalents.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An organic compound having a structure of Chemical Formula 1:

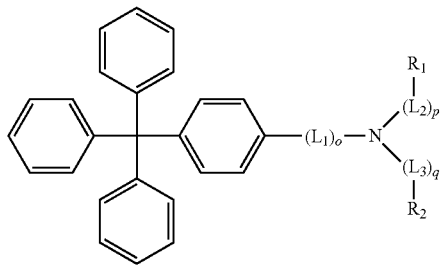

Chemical Formula 1 wherein each of $R_1$ and $R_2$ is independently an unsubstituted or substituted $C_5$~$C_{30}$ aryl group or an unsubstituted or substituted $C_4$~$C_{30}$ hetero aryl group, wherein at least one of $R_1$ and $R_2$ is an unsubstituted or substituted $C_{10}$~$C_{30}$ hetero aryl group, which has at least one of oxygen (O) and sulfur (S) in a ring; each of $L_1$, $L_2$, and $L_3$ is independently an unsubstituted or substituted $C_5$~$C_{30}$ arylene group or an unsubstituted or substituted $C_4$~$C_{30}$ hetero arylene group; o is an integer of 1 or 2; and each of p and q is independently an integer of 0 to 2.

2. The organic compound of claim 1, wherein at least one of $R_1$ and $R_2$ has a hetero aromatic moiety selected from the group consisting of dibenzofuranyl, dibenzothiophenyl, xanthenyl, benzo-chromenyl, thianthrenyl, phenoxazinyl, phenothiazinyl and phenoxathinyl, each of which is unsubstituted or substituted.

3. The organic compound of claim 1, wherein each of $L_1$, $L_2$, and $L_3$ comprises 1 or 2 aromatic rings or 1 or 2 hetero aromatic rings.

4. The organic compound of claim 1, wherein the organic compound has a structure of Chemical Formula 2:

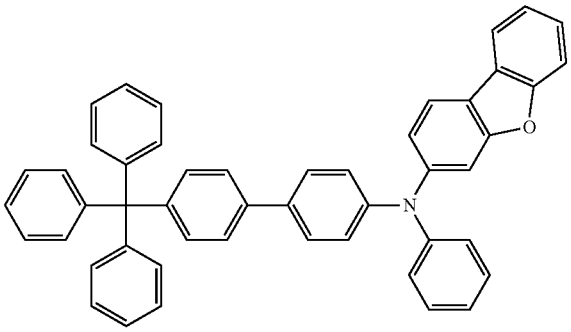

17

-continued
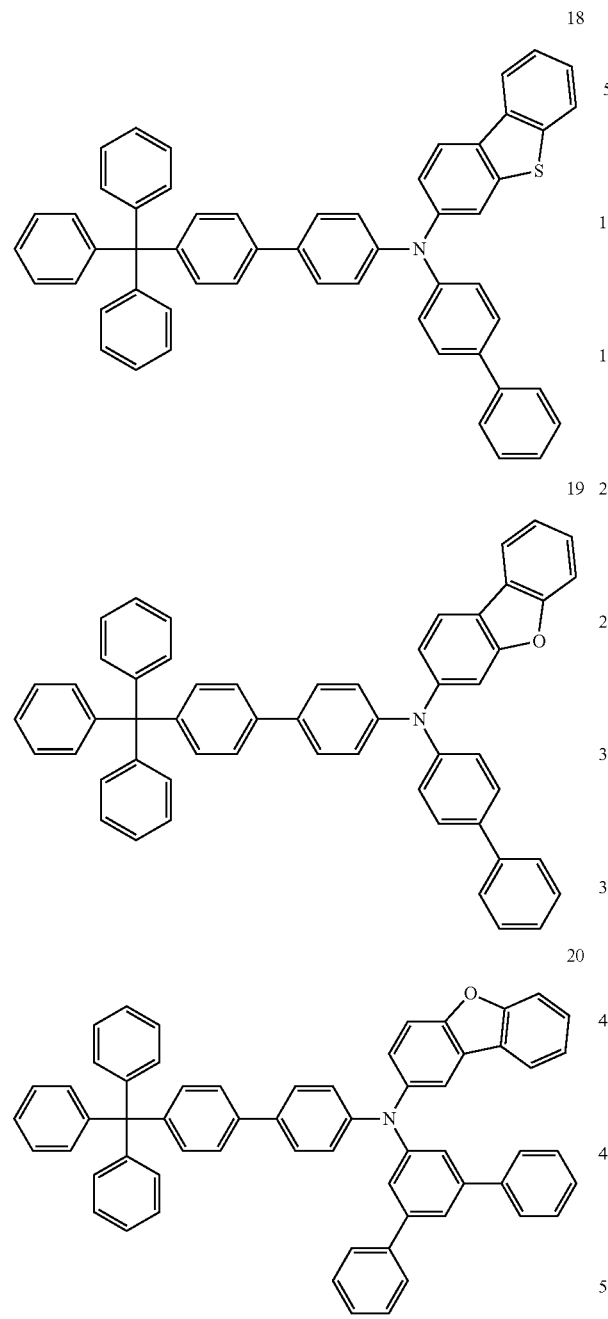
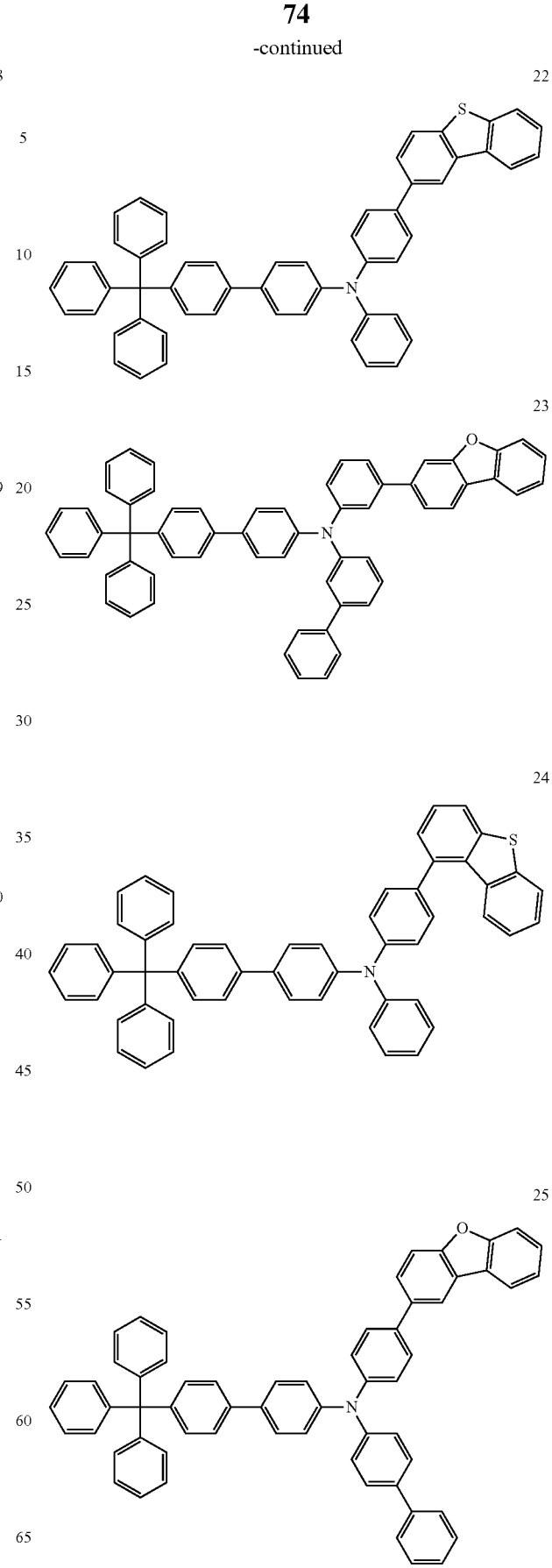

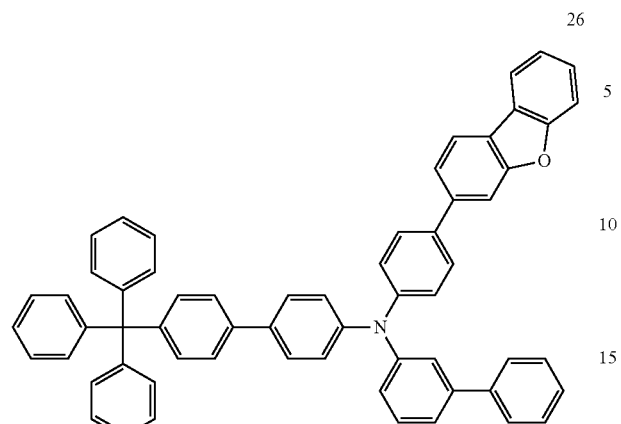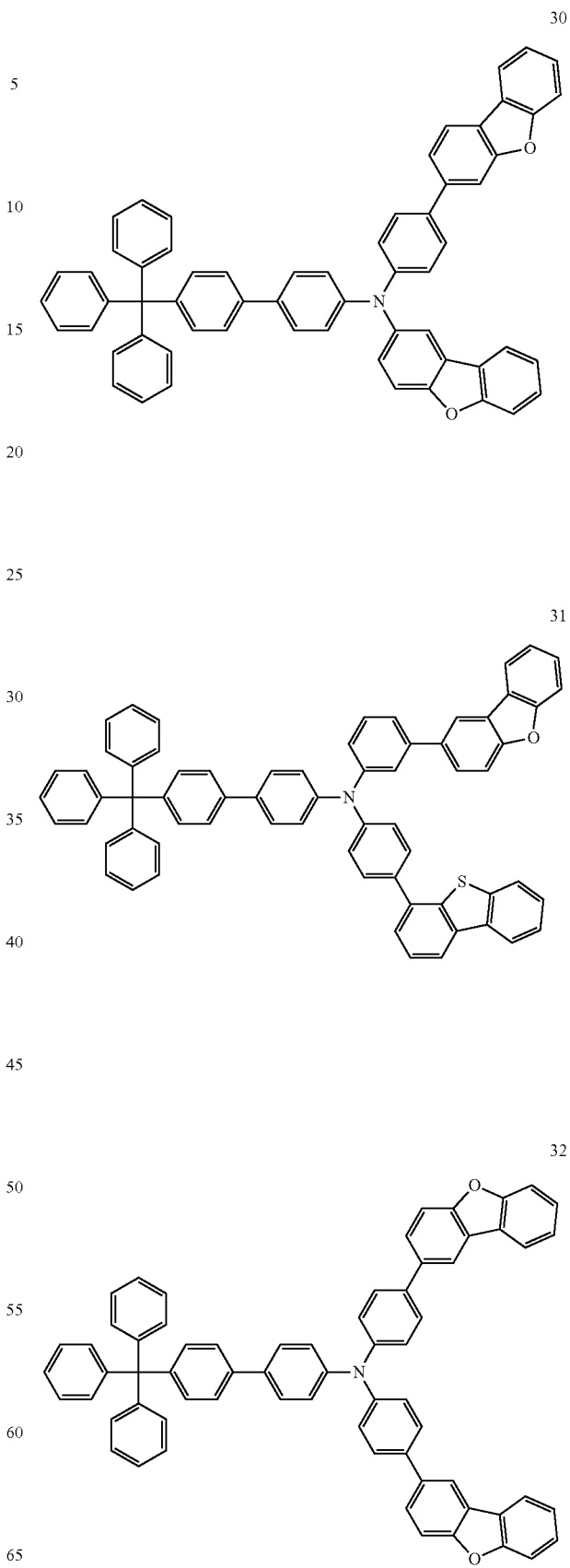

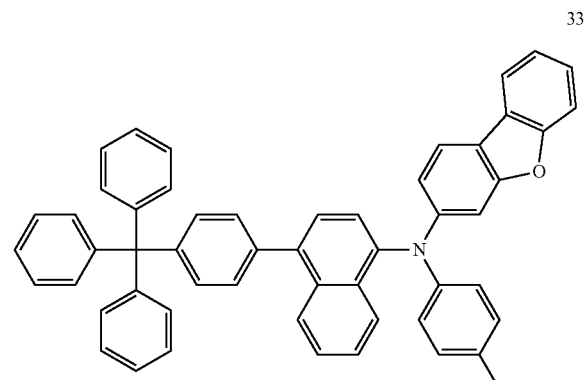
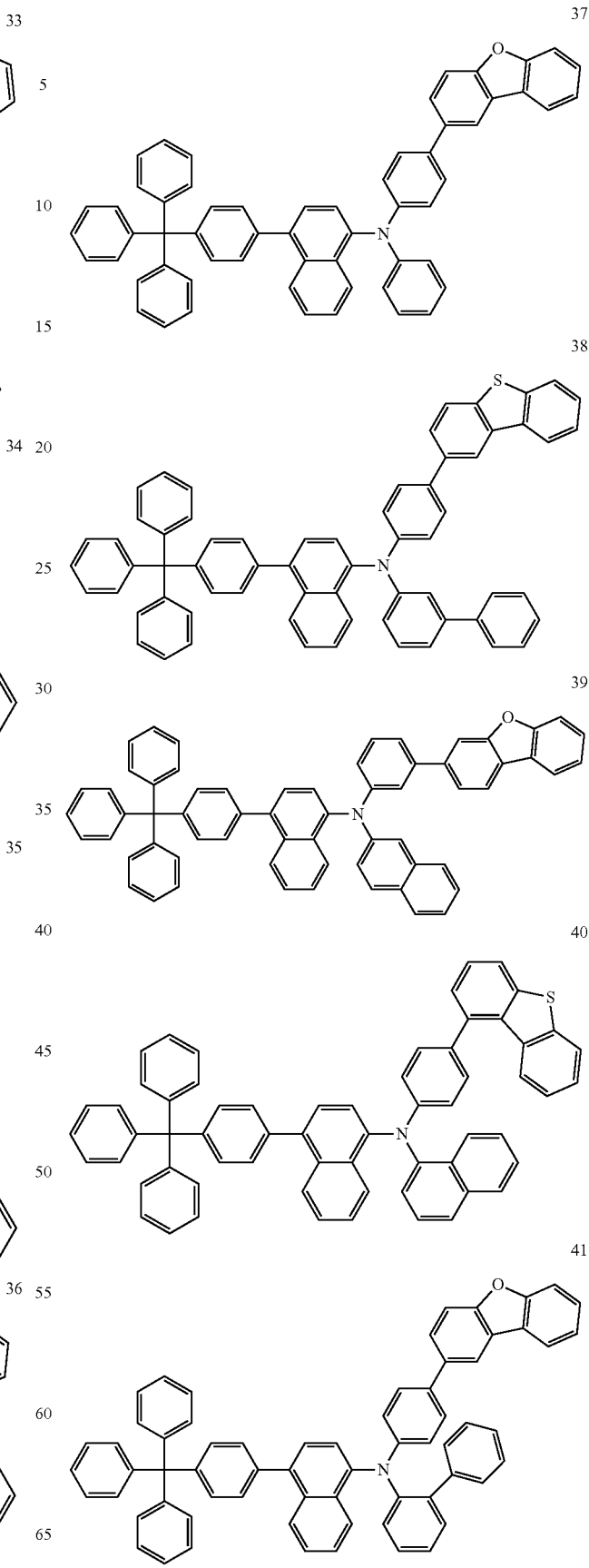

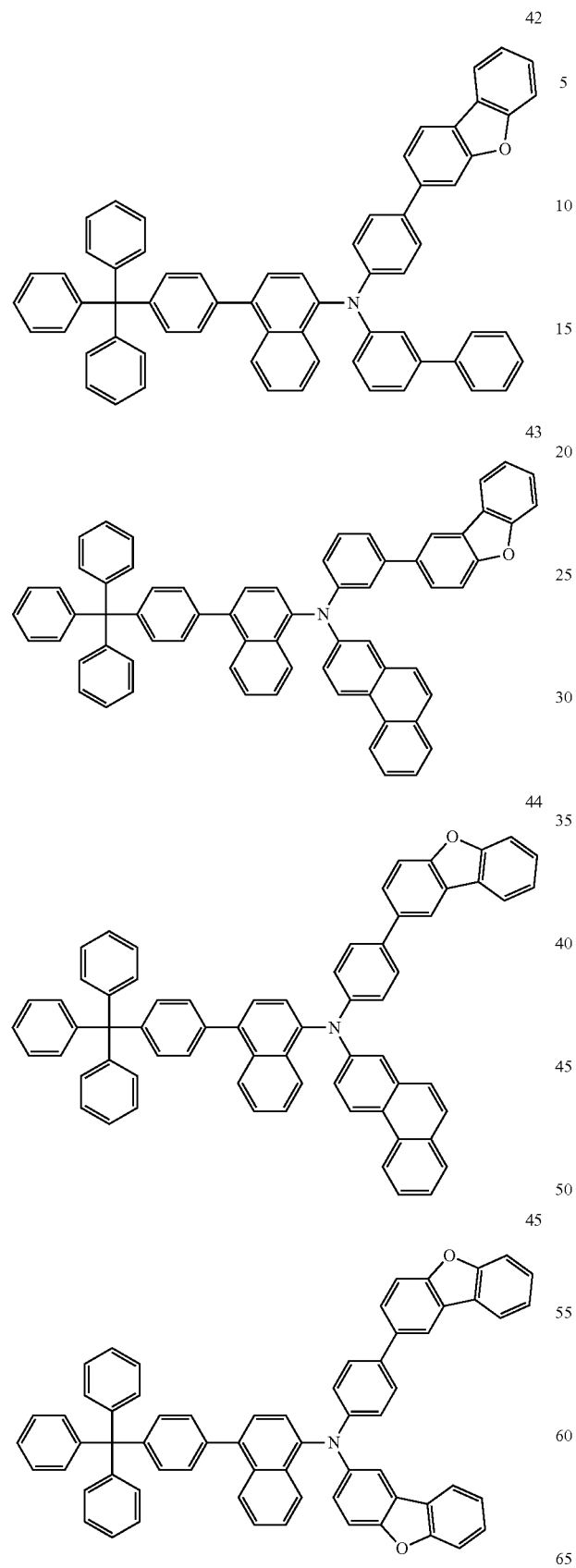
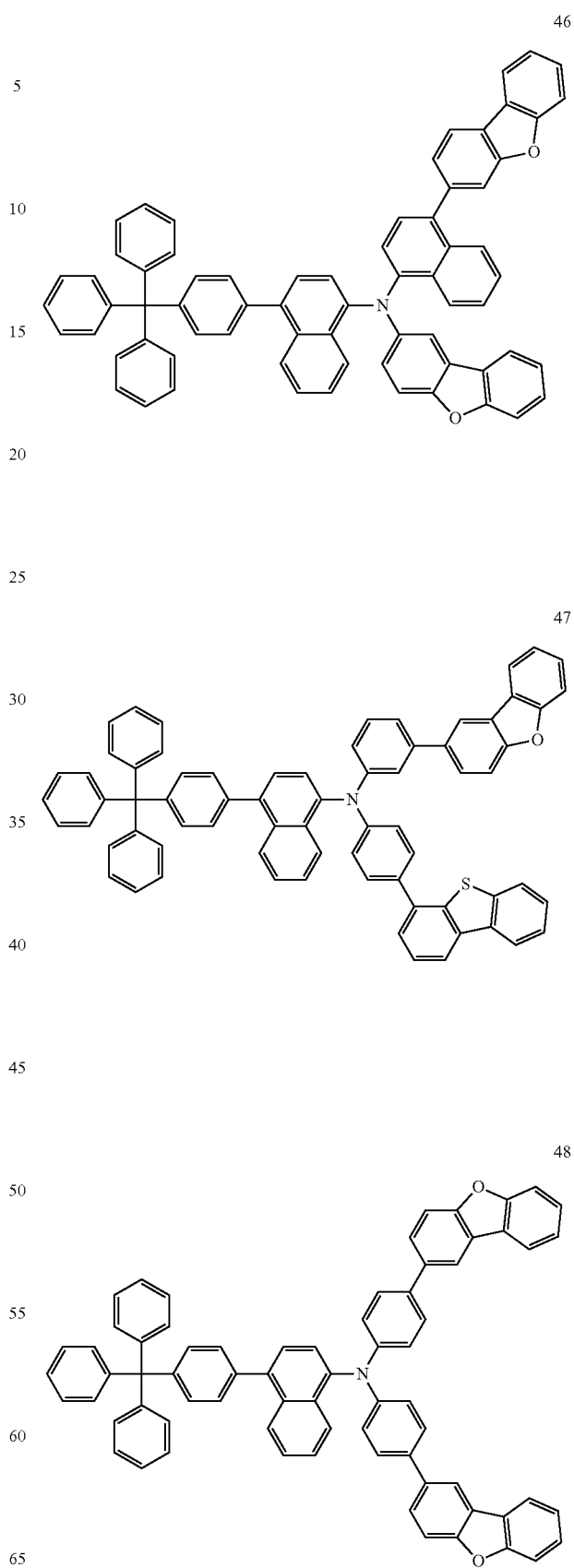

-continued
49
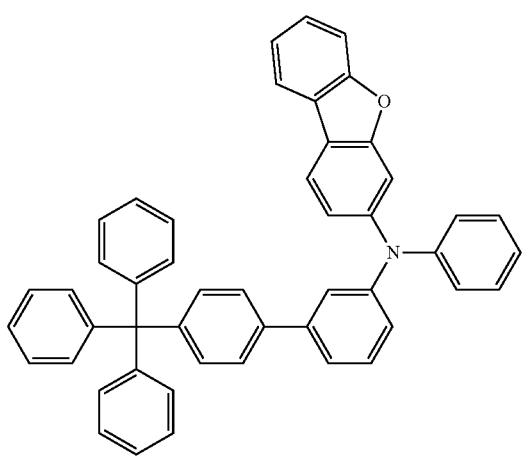
50
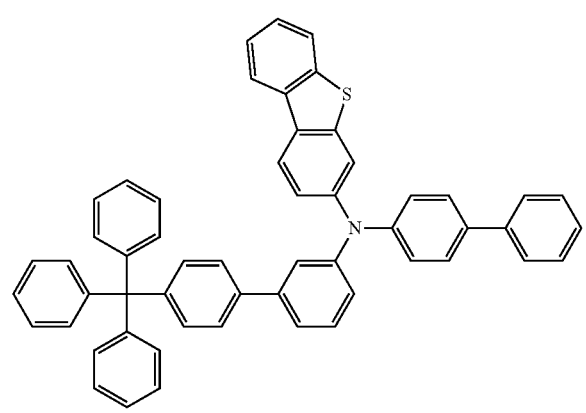
51
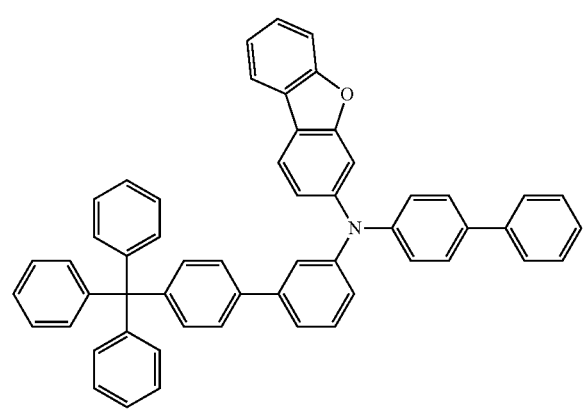
52
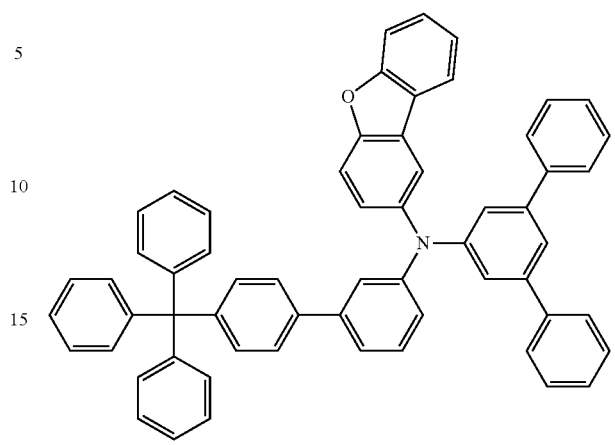
53
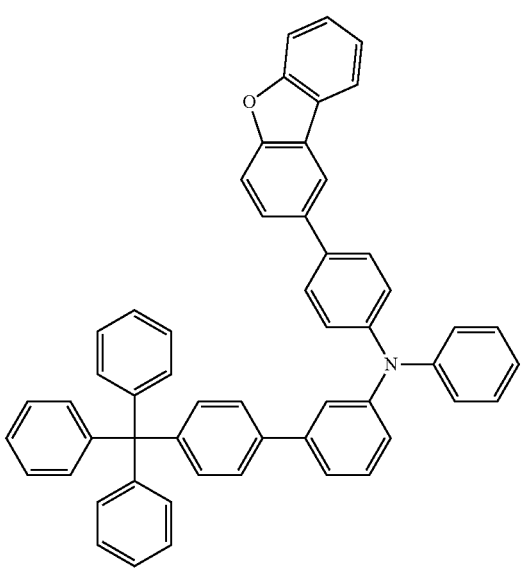
54
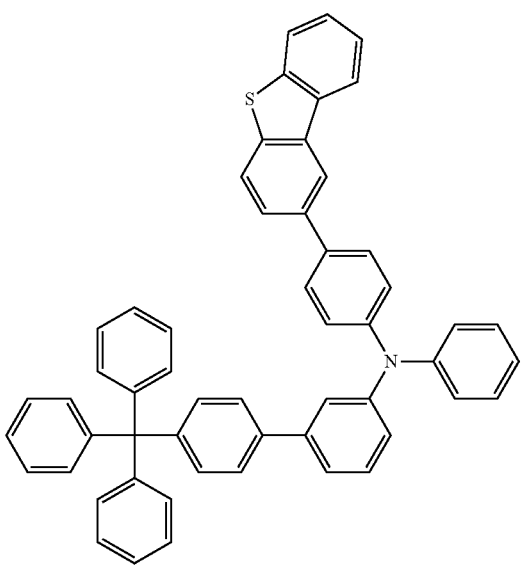

55
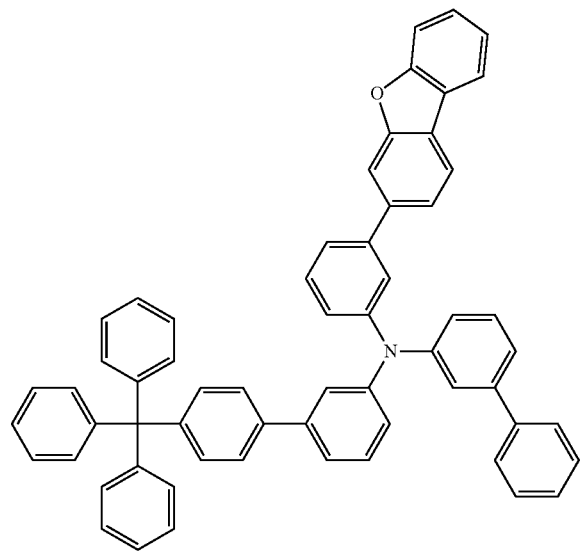
56
58
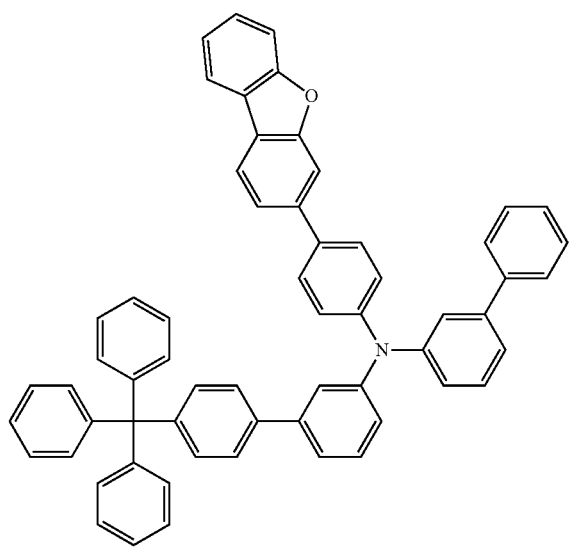
59
57
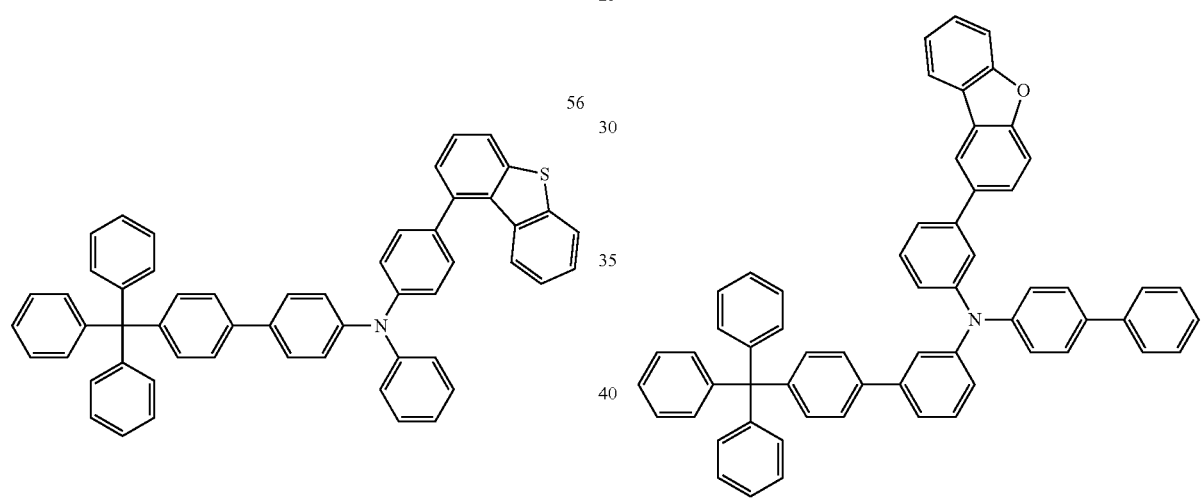
60
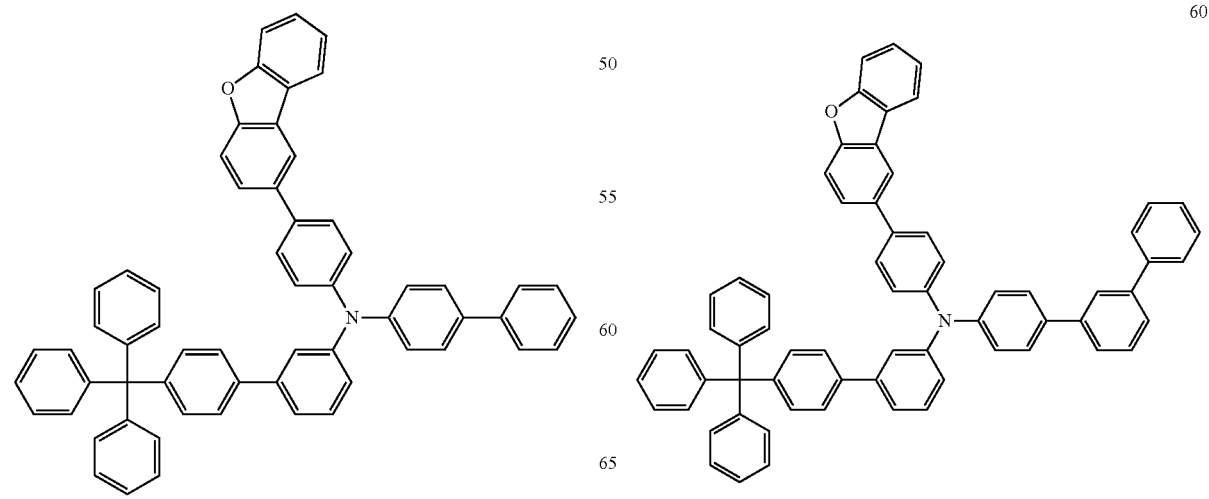

61

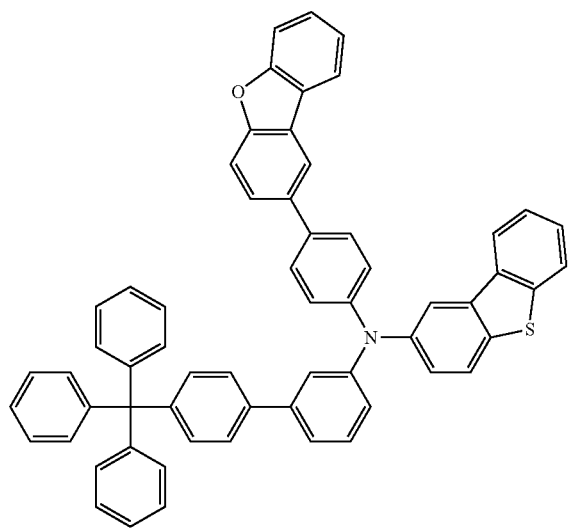

62

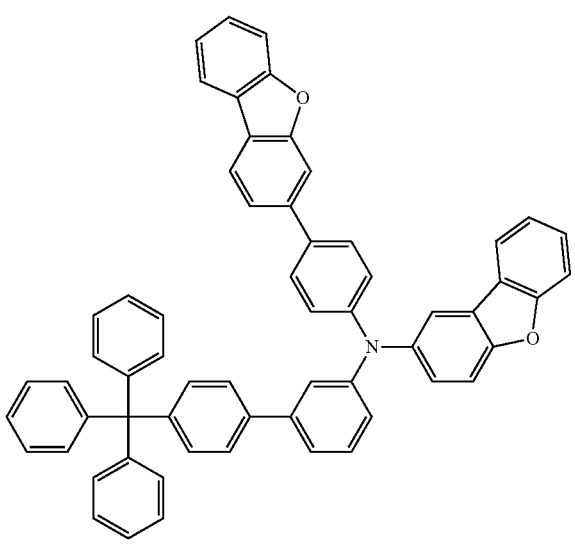

63

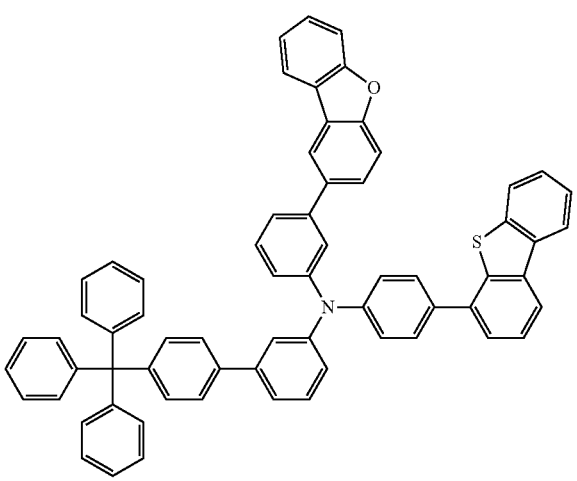

64

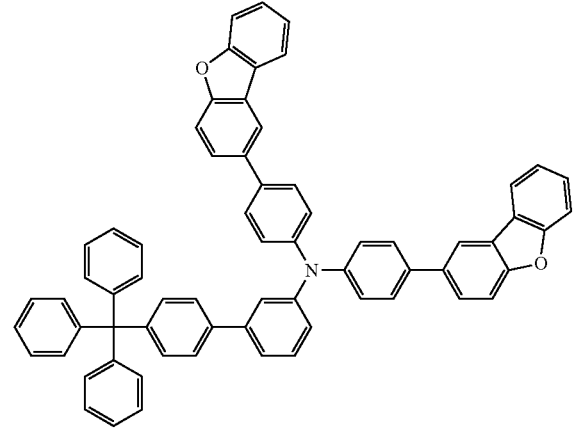

5. A light emitting diode, comprising:
a first electrode;
a second electrode,
    wherein the first electrode and the second electrode face each other;
an emitting material layer,
    wherein the emitting material layer is disposed between the first and second electrodes; and
a hole transfer layer,
    wherein the hole transfer layer is disposed between the first electrode and the emitting material layer and comprises an organic compound having a structure of Chemical Formula 1:

Chemical Formula 1

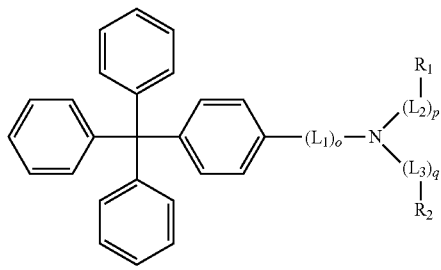

wherein each of $R_1$ and $R_2$ is independently an unsubstituted or substituted $C_5$~$C_{30}$ aryl group or an unsubstituted or substituted $C_4$~$C_{30}$ hetero aryl group, wherein at least one of $R_1$ and $R_2$ is an unsubstituted or substituted $C_{10}$~$C_{30}$ hetero aryl group, which has at least one of oxygen (O) and sulfur (S) in a ring; each of $L_1$, $L_2$, and $L_3$ is independently an unsubstituted or substituted $C_5$~$C_{30}$ arylene group or an unsubstituted or substituted $C_4$~$C_{30}$ hetero arylene group; o is an integer of 1 or 2; and each of p and q is independently an integer of 0 to 2.

6. The light emitting diode of claim 5, wherein at least one of $R_1$ and $R_2$ has a hetero aromatic moiety selected from the group consisting of dibenzofuranyl, dibenzothiophenyl, xanthenyl, benzo-chromenyl, thianthrenyl, phenoxazinyl, phenothiazinyl and phenoxathinyl, each of which is unsubstituted or substituted.

7. The light emitting diode of claim 5, wherein each of $L_1$, $L_2$, and $L_3$ comprises 1 or 2 aromatic rings or 1 or 2 hetero aromatic rings.

8. The light emitting diode of claim 5, wherein the hole transfer layer comprises a hole injection layer, and a hole transport layer disposed between the hole injection layer and the emitting material layer and, and wherein the hole transport layer comprises the organic compound.

9. The light emitting diode of claim 8, wherein the hole transport layer comprises a host and a dopant, and wherein the host comprises the organic compound.

10. The light emitting diode of claim 8, wherein the hole transport layer comprises a first hole transport layer disposed between the hole injection layer and the emitting material layer and a second hole transport layer disposed between the first hole transport layer and the emitting material layer, and wherein the second hole transport layer comprises the organic compound.

11. A light emitting device, comprising:
a substrate;
a thin-film transistor disposed over the substrate; and
the light emitting diode according to claim 5,
wherein the light emitting diode is disposed on the substrate and is electrically connected to the thin-film transistor.

12. A light emitting diode, comprising:
a first electrode;
a second electrode,
wherein the first electrode and the second electrode face each other;
an emitting material layer,
wherein the emitting material layer is disposed between the first and second electrodes; and
an electron blocking layer,
wherein the electron blocking layer is disposed between the first electrode and the emitting material layer and comprises an organic compound having a structure of Chemical Formula 1:

Chemical Formula 1

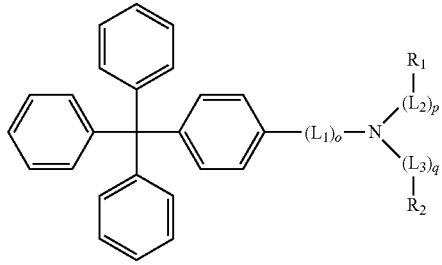

wherein each of $R_1$ and $R_2$ is independently an unsubstituted or substituted $C_5$~$C_{30}$ aryl group or an unsubstituted or substituted $C_4$~$C_{30}$ hetero aryl group, wherein at least one of $R_1$ and $R_2$ is an unsubstituted or substituted $C_{10}$~$C_{30}$ hetero aryl group, which has at least one of oxygen (O) and sulfur (S) in a ring; each of $L_1$, $L_2$, and $L_3$ is independently an unsubstituted or substituted $C_5$~$C_{30}$ arylene group or an unsubstituted or substituted $C_4$~$C_{30}$ hetero arylene group; and each of o, p and q is independently an integer of 0 to 2.

13. The light emitting diode of claim 12, wherein at least one of $R_1$ and $R_2$ has a hetero aromatic moiety selected from the group consisting of dibenzofuranyl, dibenzothiophenyl, xanthenyl, benzo-chromenyl, thianthrenyl, phenoxazinyl, phenothiazinyl and phenoxathinyl, each of which is unsubstituted or substituted.

14. The light emitting diode of claim 12, wherein each of $L_1$, $L_2$, and $L_3$ includes 1 or 2 aromatic rings, or 1 or 2 hetero aromatic rings.

15. A light emitting device, comprising:
a substrate;
a thin-film transistor disposed over the substrate; and
the light emitting diode according to claim 11,
wherein the light emitting diode is disposed on the substrate and is electrically connected to the thin-film transistor.

16. A light emitting diode, comprising:
a first electrode;
a second electrode,
wherein the first electrode and second electrode face each other;
a first emitting unit,
wherein the first emitting unit is disposed between the first and second electrodes, and wherein the first emitting unit comprises a first emitting material layer;
a second emitting unit,
wherein the second emitting unit is disposed between the first emitting unit, and wherein the second emitting unit comprises a second emitting material layer; and a P-type charge generation layer,
wherein the P-type charge generation layer is disposed between the first and second emitting units and wherein the P-type charge generation layer comprises an organic compound having a structure of Chemical Formula 1:

Chemical Formula 1

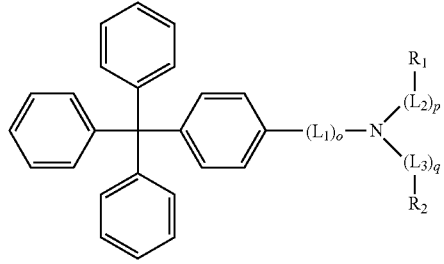

wherein each of $R_1$ and $R_2$ is independently an unsubstituted or substituted $C_5$~$C_{30}$ aryl group or an unsubstituted or substituted $C_4$~$C_{30}$ hetero aryl group, wherein at least one of $R_1$ and $R_2$ is an unsubstituted or substituted $C_{10}$~$C_{30}$ hetero aryl group, which has at least one of oxygen (O) and sulfur (S) in a ring; each of $L_1$, $L_2$, and $L_3$ is independently an unsubstituted or substituted $C_5$~$C_{30}$ arylene group or an unsubstituted or substituted $C_4$~$C_{30}$ hetero arylene group; and each of o, p and q is independently an integer of 0 to 2.

17. The light emitting diode of claim 16, wherein at least one of $R_1$ and $R_2$ has a hetero aromatic moiety selected from the group consisting of dibenzofuranyl, dibenzothiophenyl, xanthenyl, benzo-chromenyl, thianthrenyl, phenoxazinyl, phenothiazinyl and phenoxathinyl, each of which is unsubstituted or substituted.

18. The light emitting diode of claim 16, wherein each of $L_1$, $L_2$, and $L_3$ includes 1 or 2 aromatic rings or 1 or 2 hetero aromatic rings.

19. The light emitting diode of claim 16, wherein the P-type charge generation layer comprises the organic compound doped with a hole injection material.

20. The light emitting diode of claim 16, further comprising an N-type charge generation layer disposed between the first emitting unit and the P-type charge generation layer.

21. The light emitting diode of claim 20, wherein the first emitting unit further comprises a first hole transfer layer disposed between the first electrode and the first emitting material layer, and the second emitting unit further comprises a second hole transfer layer disposed between the P-type charge generation layer and the second emitting material layer.

22. The light emitting diode of claim 21, wherein at least one of the first and second hole transfer layers comprises the organic compound.

23. The light emitting diode of claim 21, wherein the first hole transfer layer comprises a first hole injection layer disposed between the first electrode and the first emitting material layer and a first hole transport layer disposed between the first hole injection layer and the first emitting material layer and the second hole transfer layer comprises a second hole transport layer disposed between the P-type charge generation layer and the second emitting material layer, and
wherein at least one of the first and second hole transport layer comprises the organic compound.

24. The light emitting diode of claim 23, the second hole transfer layer further comprises a second hole injection layer disposed between the P-type generation layer and the second hole transport layer or between the N-type and P-type charge generation layers.

25. The light emitting diode of claim 24, wherein the second hole injection layer includes the organic compound doped with a hole injection material.

26. The light emitting diode of claim 21, wherein the first emitting unit further comprises a first electron blocking layer disposed between the first hole transfer layer and the first emitting material layer, and wherein the second emitting unit further comprises a second electron blocking layer disposed between the second hole transfer layer and the second emitting material layer.

27. The light emitting diode of claim 26, wherein at least one of the first and second electron blocking layers comprises the organic compound.

28. A light emitting device, comprising:
a substrate;
a thin-film transistor disposed over the substrate; and
the light emitting diode according to claim 14,
wherein the light emitting diode is disposed on the substrate and is electrically connected to the thin-film transistor.

29. An organic compound selected from any one of the following structures:

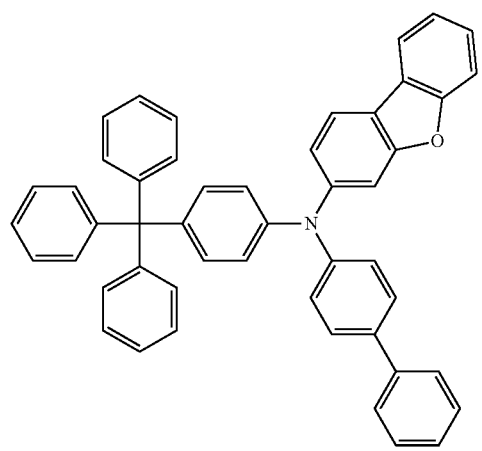

1

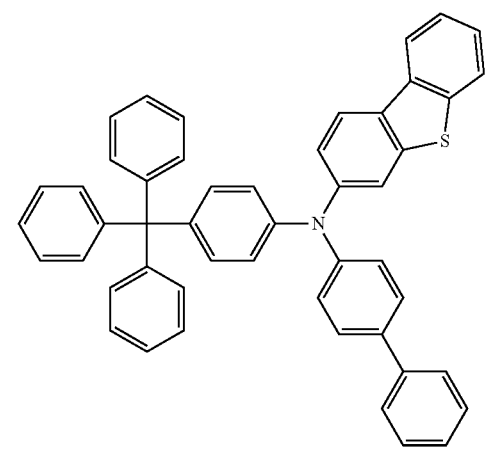

2

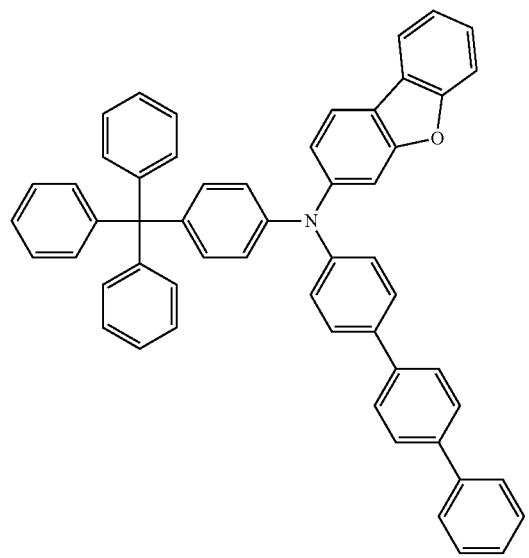

3

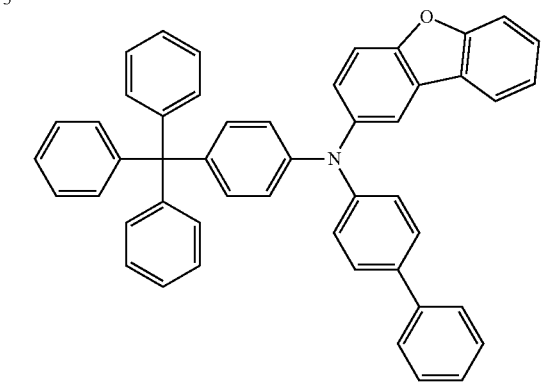

4

-continued
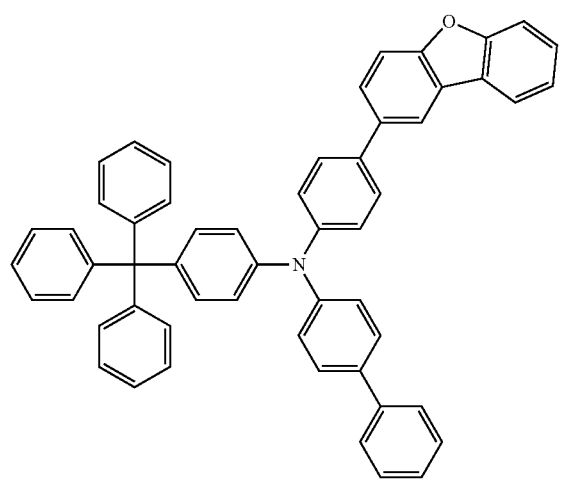
5
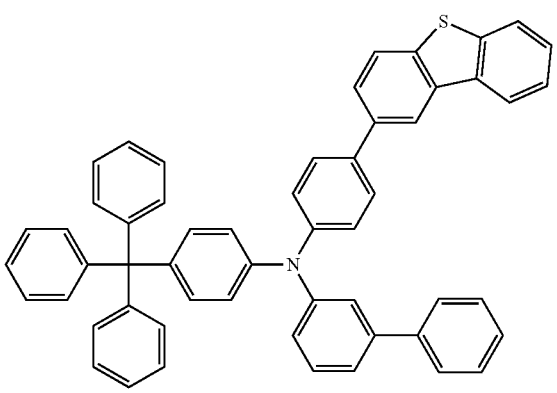
6
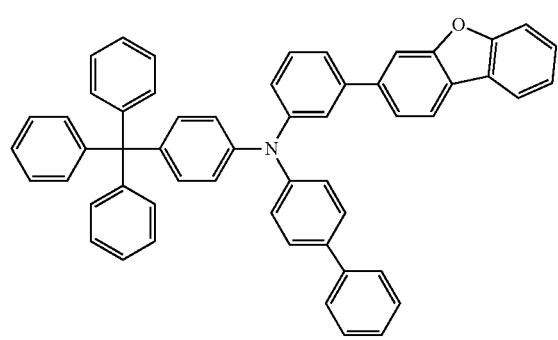
7
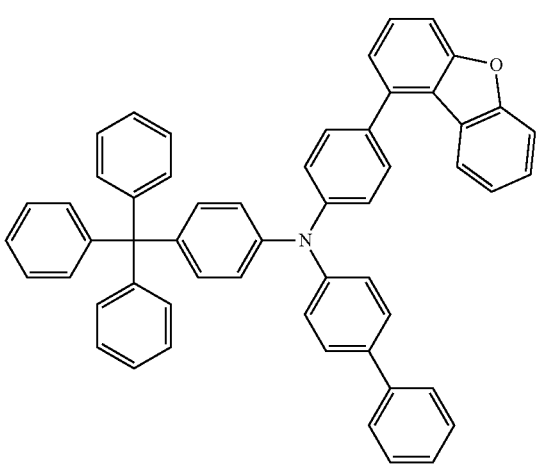
8
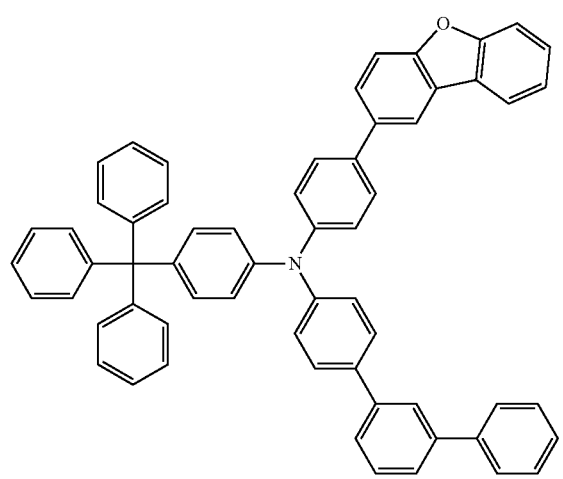
9
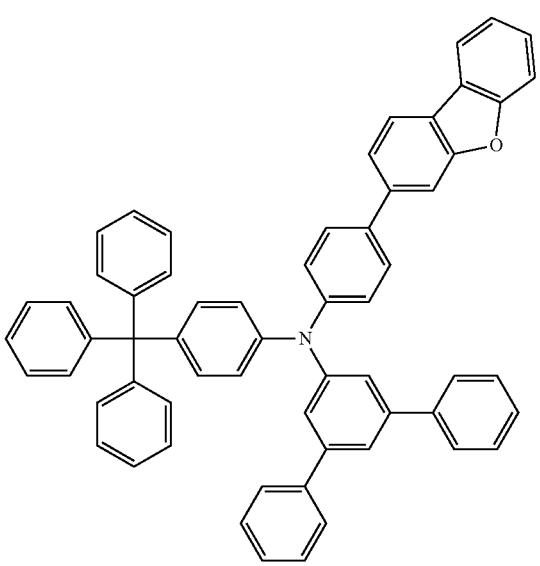
10

-continued
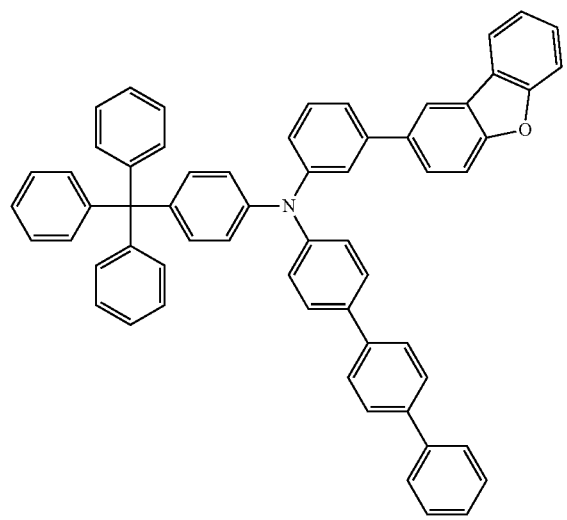
11
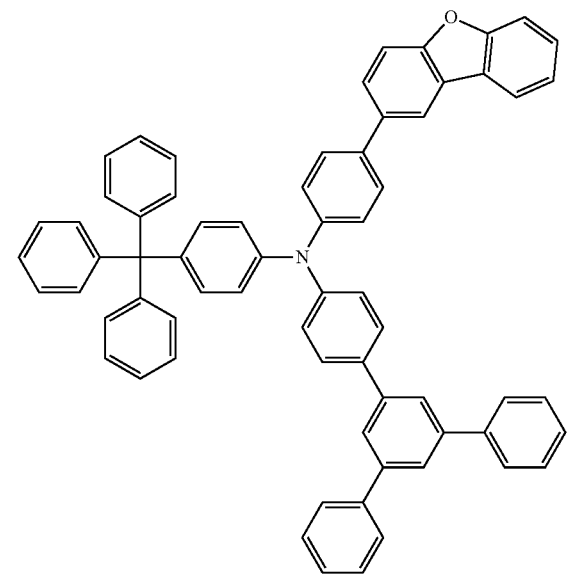
12
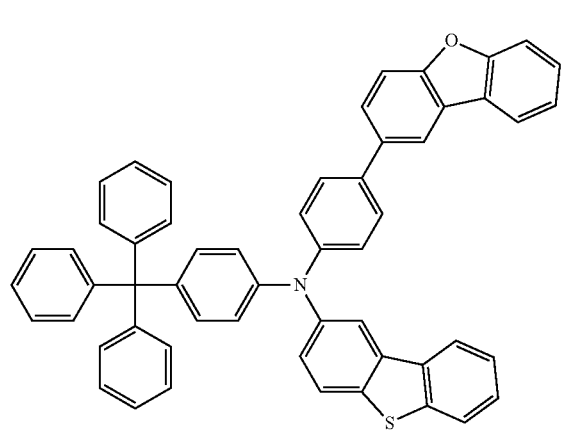
13
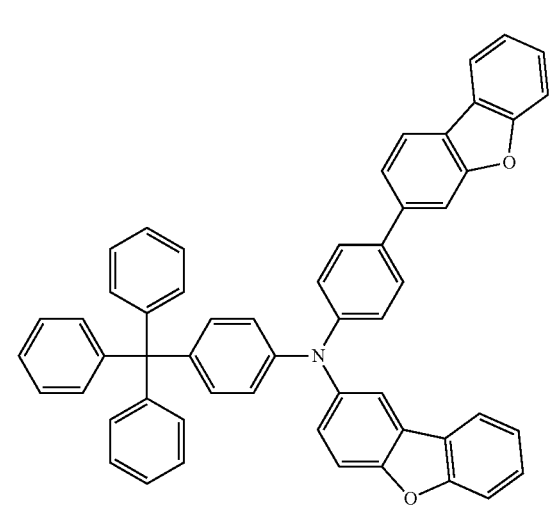
14
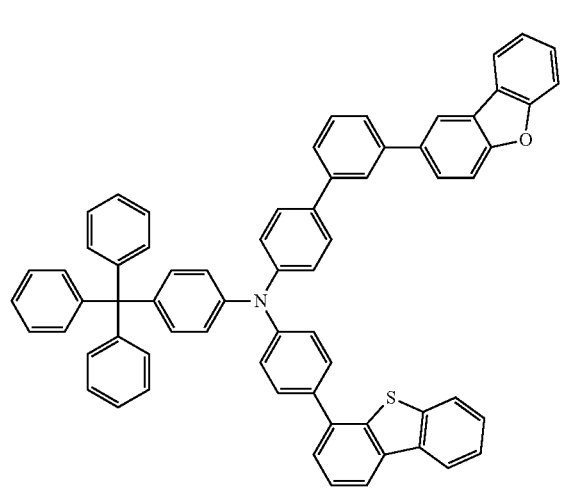
15
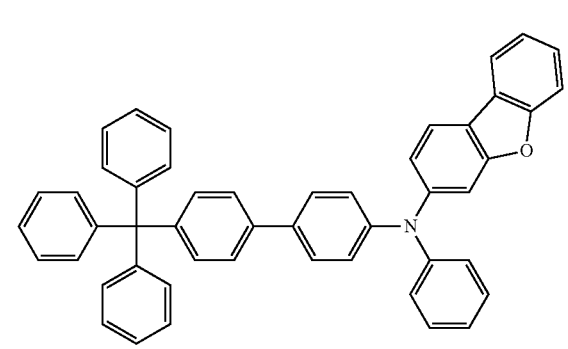
17

-continued
18
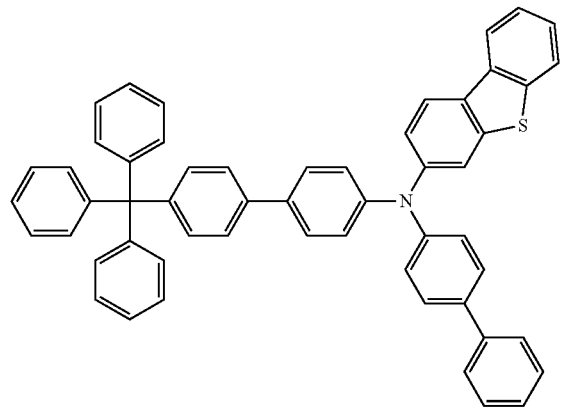
19
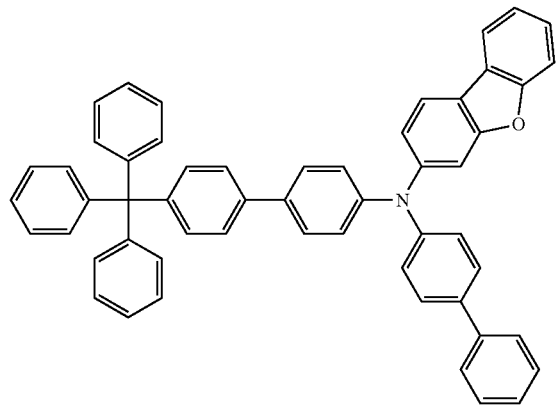
20
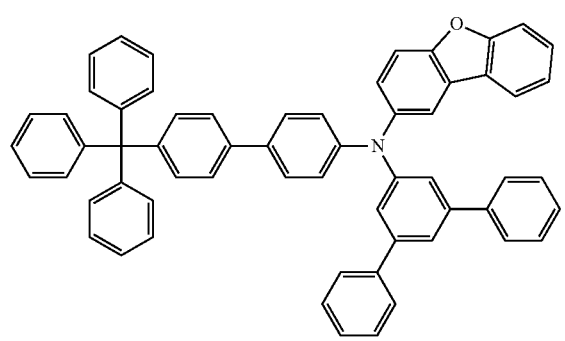
21
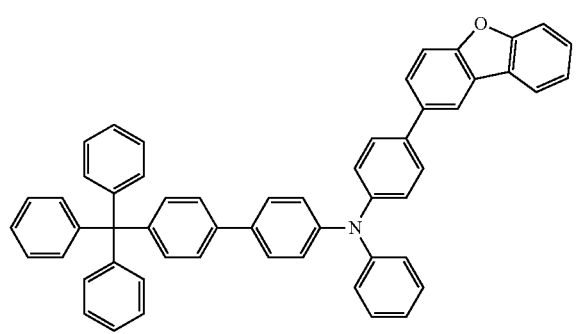
22
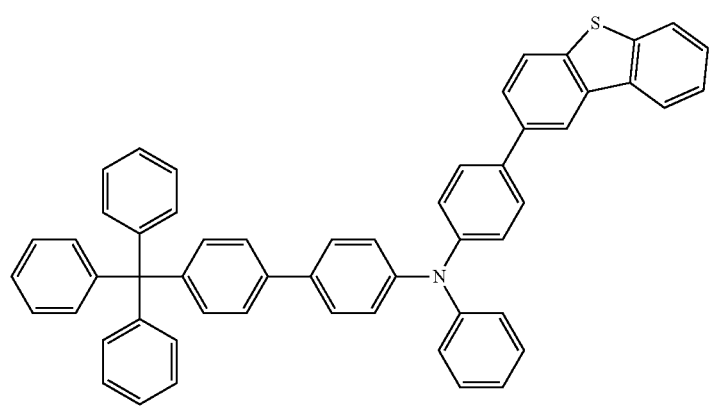
23
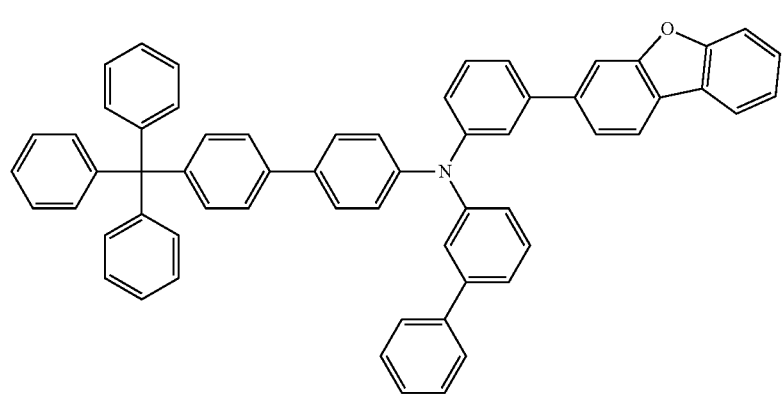

-continued
24
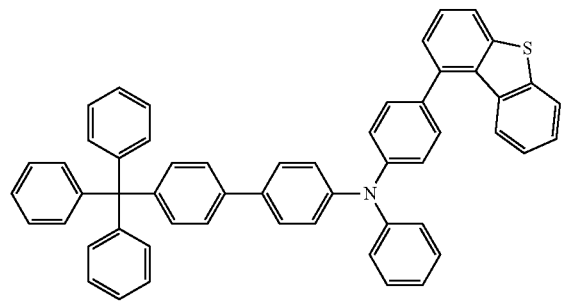
25
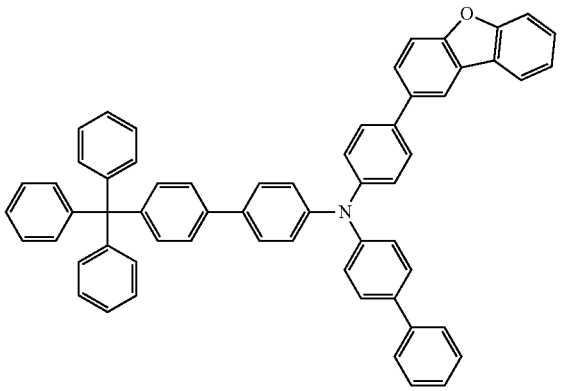
26
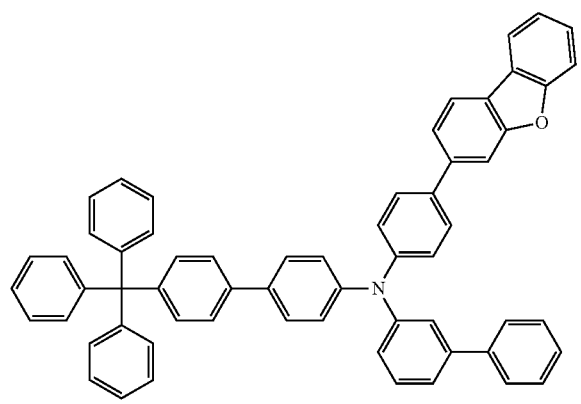
27
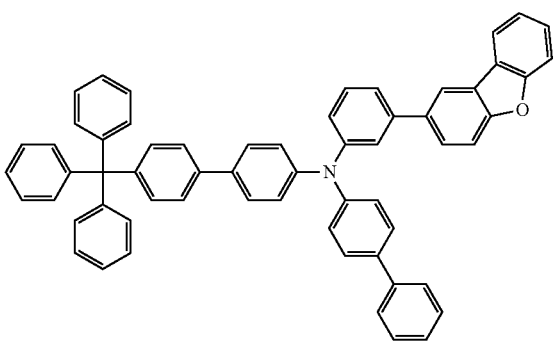
28
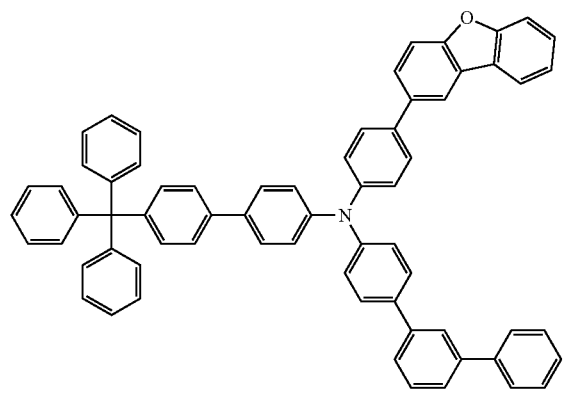
29
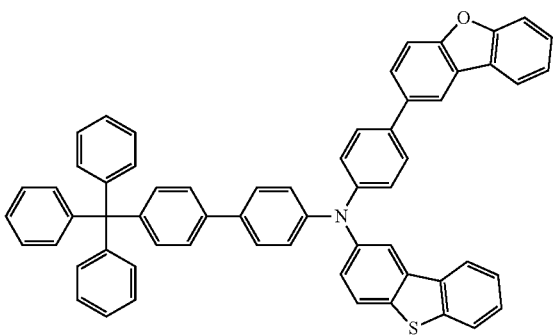
30
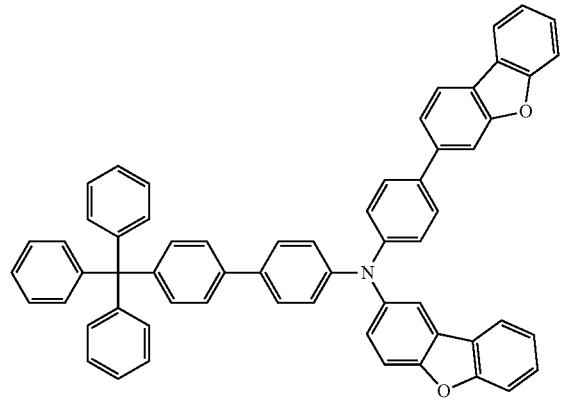
31
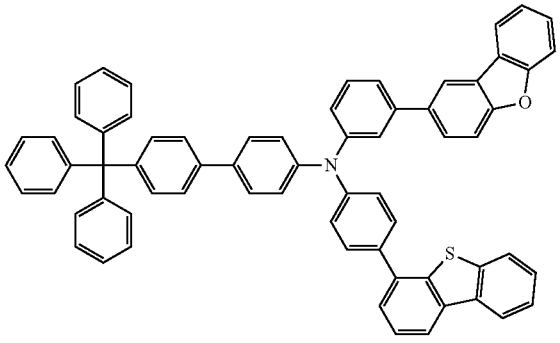

-continued
32
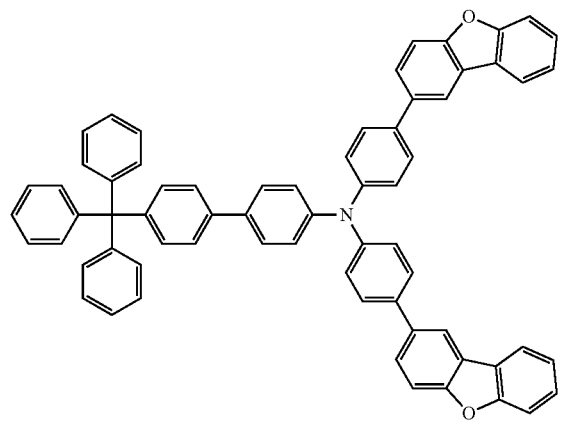
33
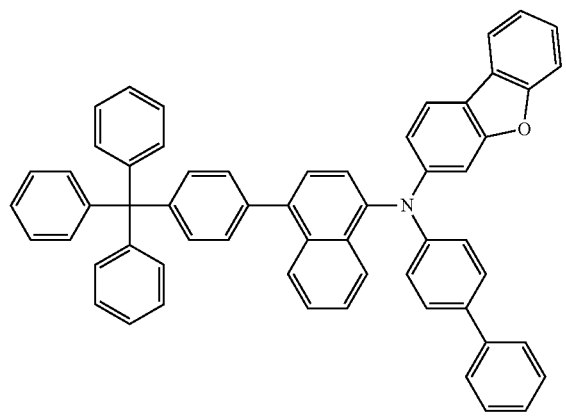
34
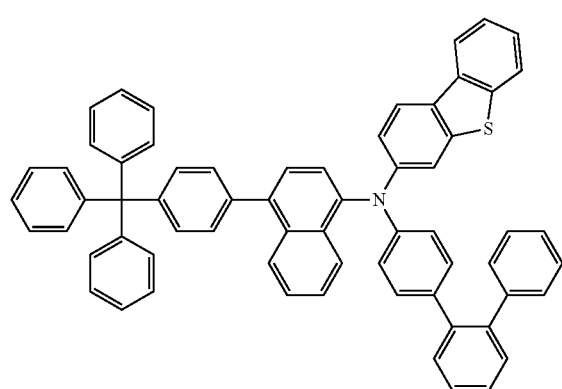
35
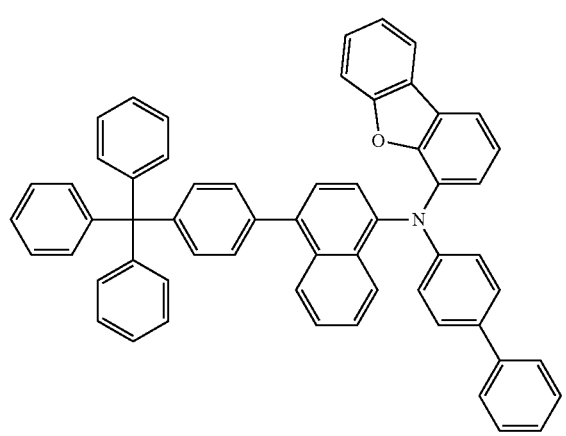
36
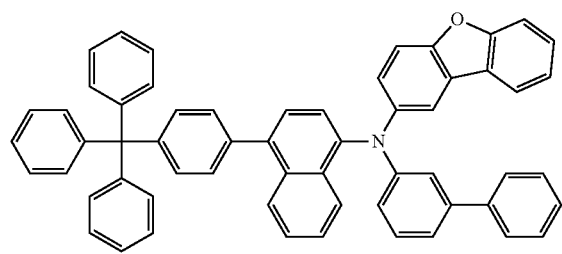
37
38
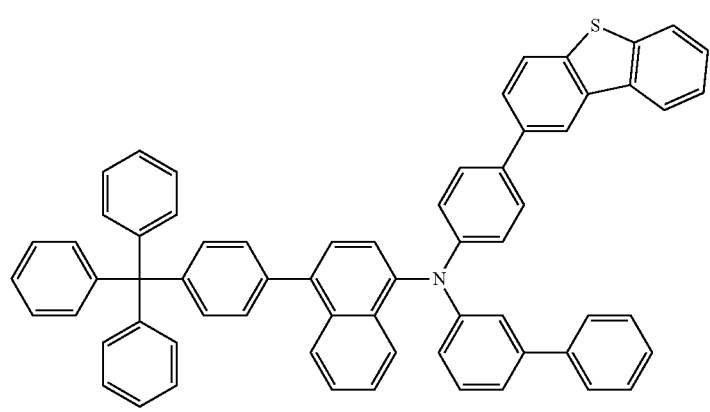

-continued
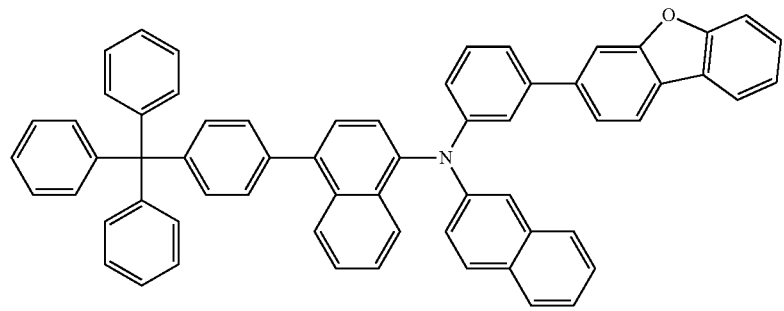
39
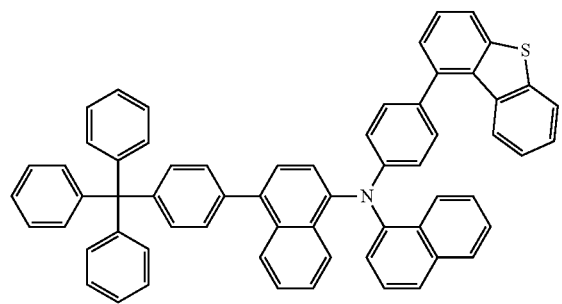
40
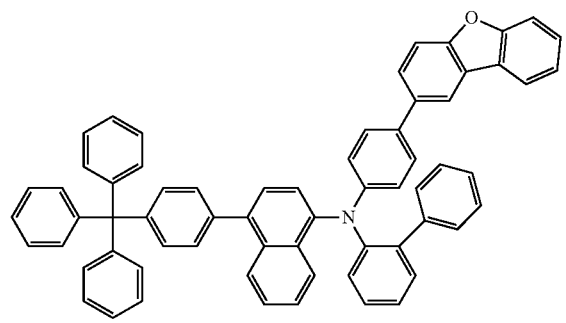
41
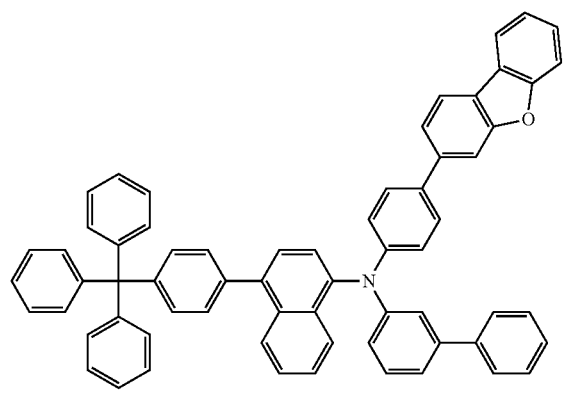
42
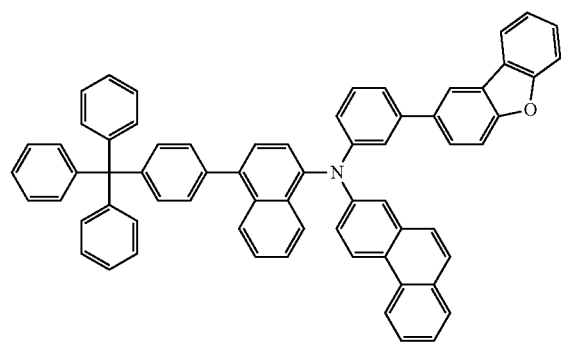
43
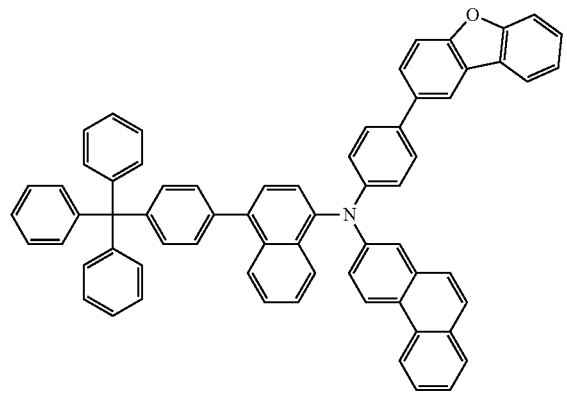
44
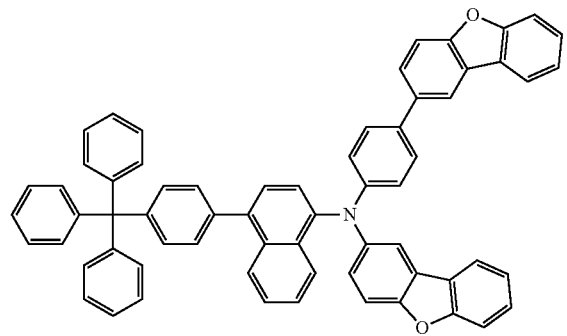
45

46
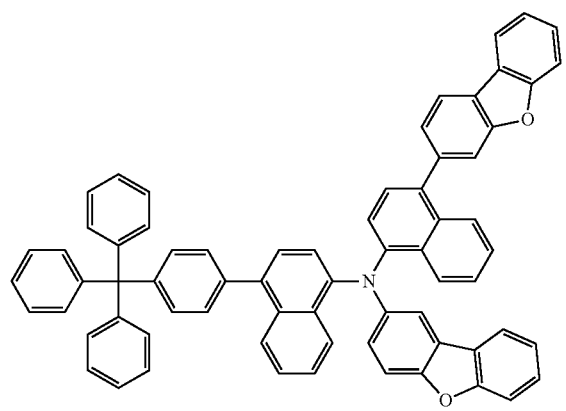
47
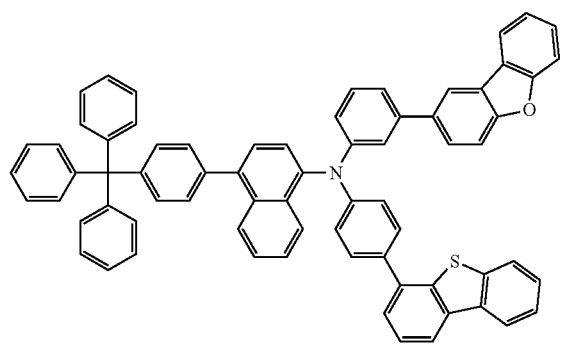
48
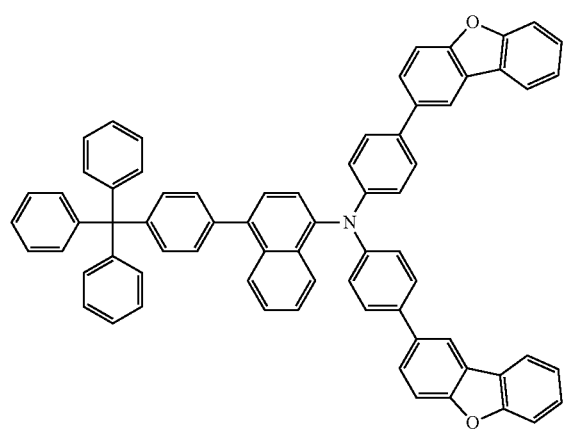
49
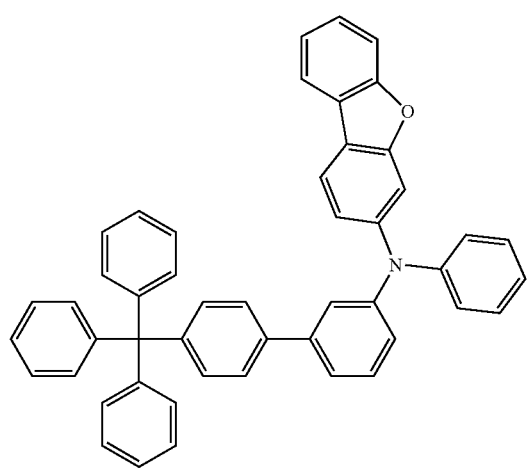
50
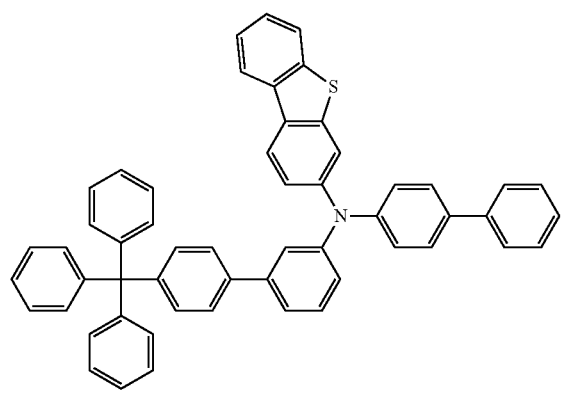
51
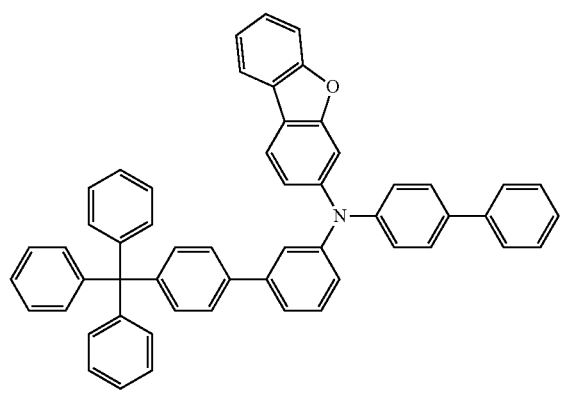

-continued
52
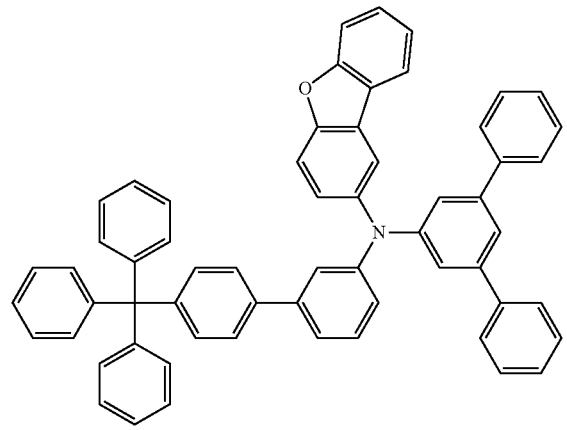
53
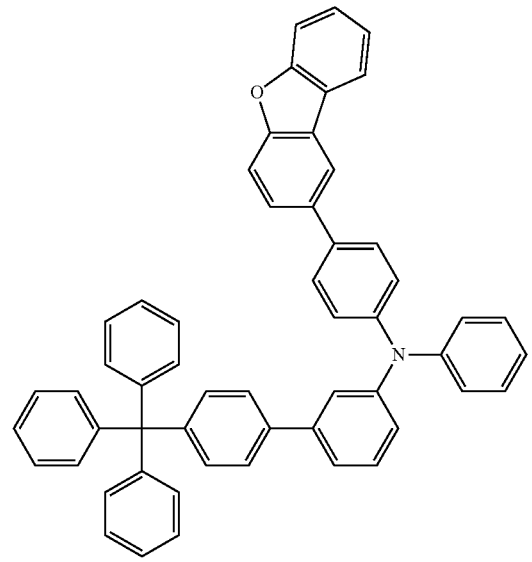
54
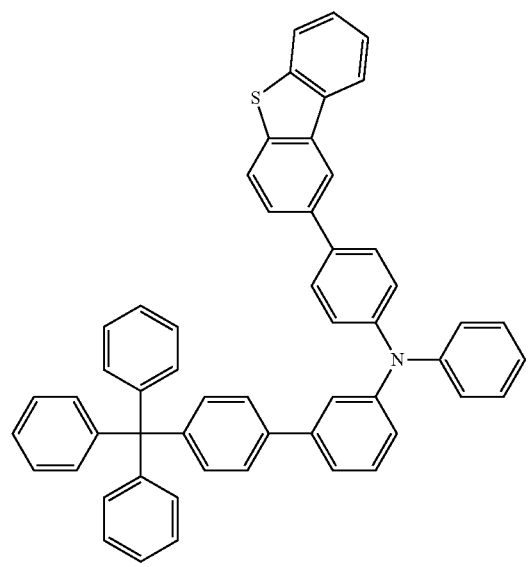
55
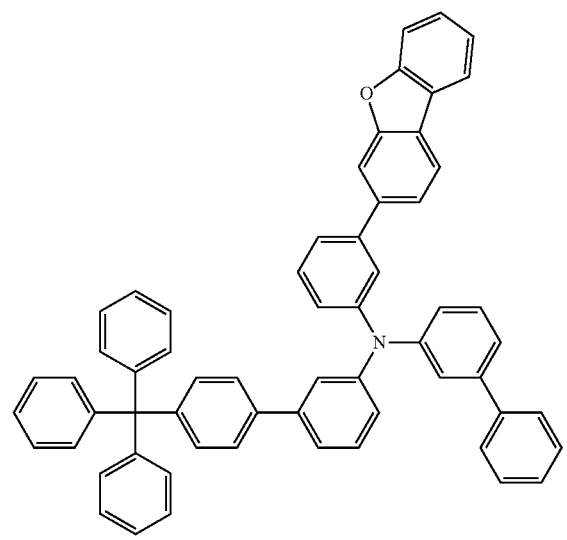
56
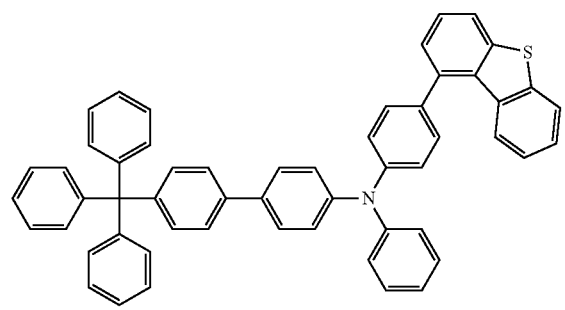
57
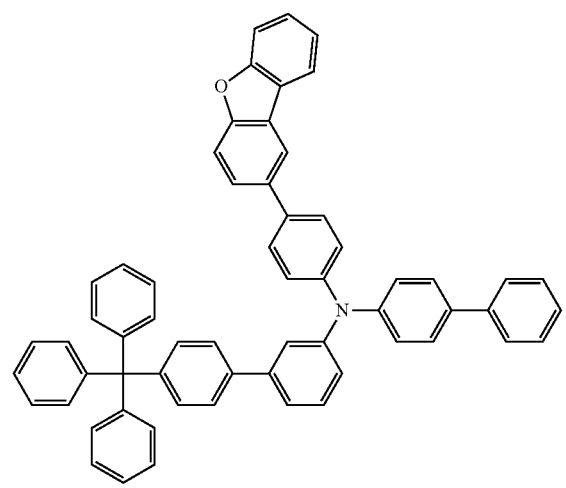

58
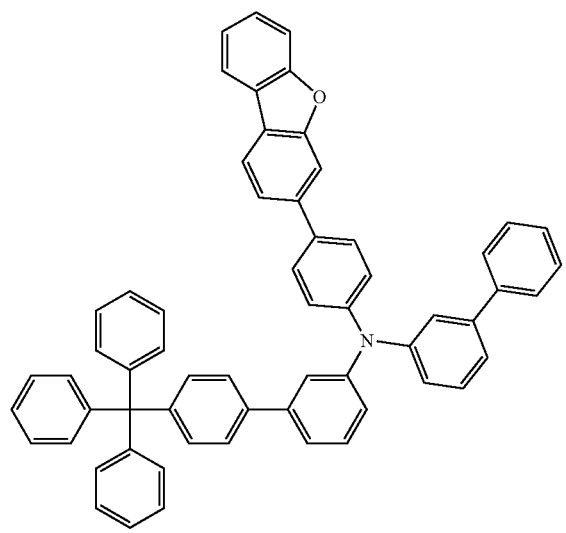
59
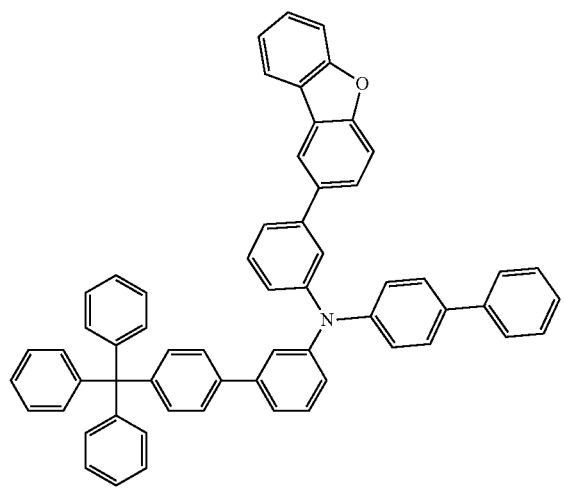
60
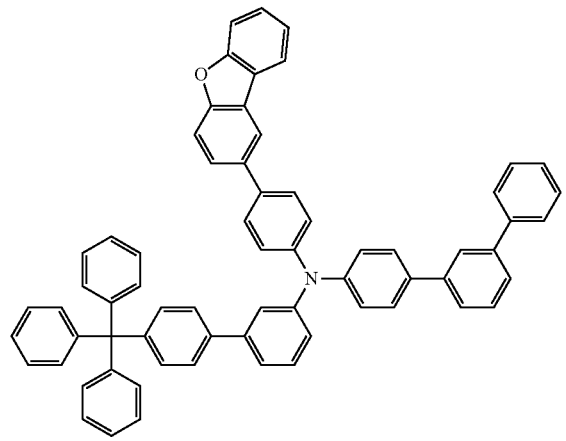
61
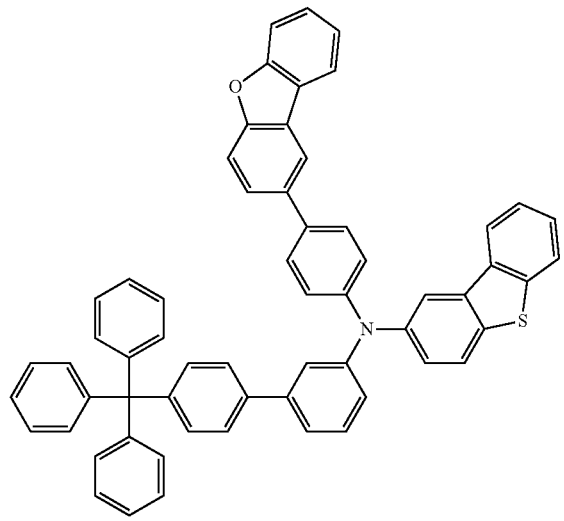

-continued

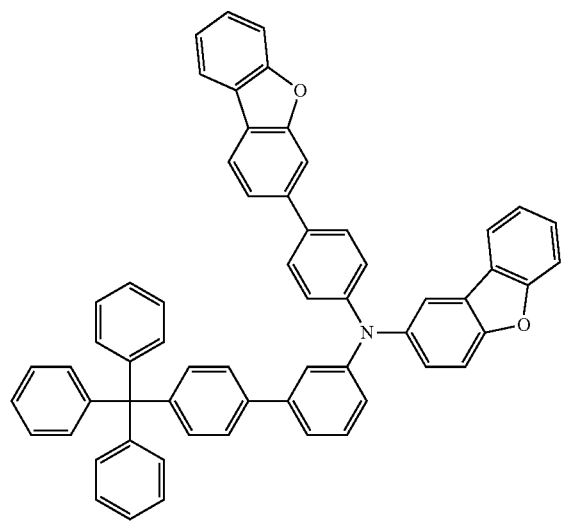
62

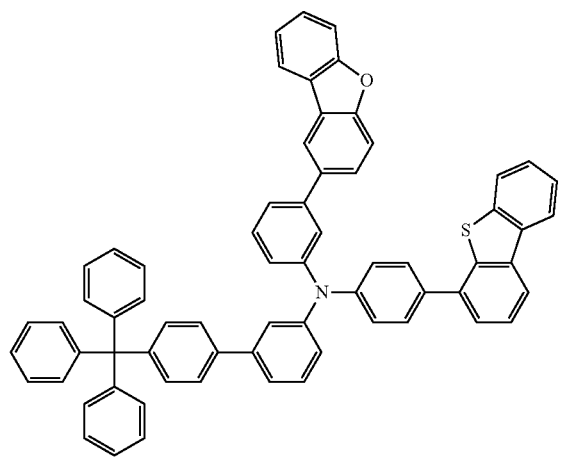
63

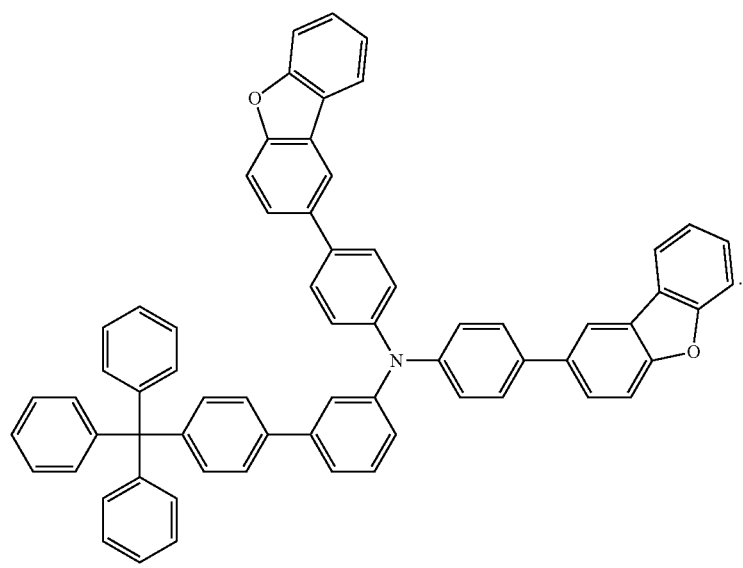
64

30. A light emitting diode, comprising:
a first electrode;
a second electrode facing the first electrode;
an emitting material layer disposed between the first and second electrodes; and
a hole transfer layer disposed between the first electrode and the emitting material layer and comprising an organic compound selected from any one of the following structures:

111 112
1
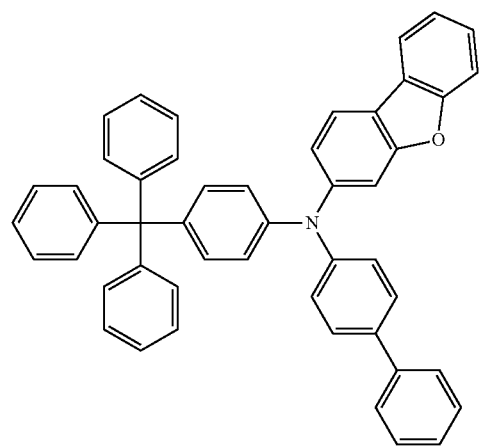
2
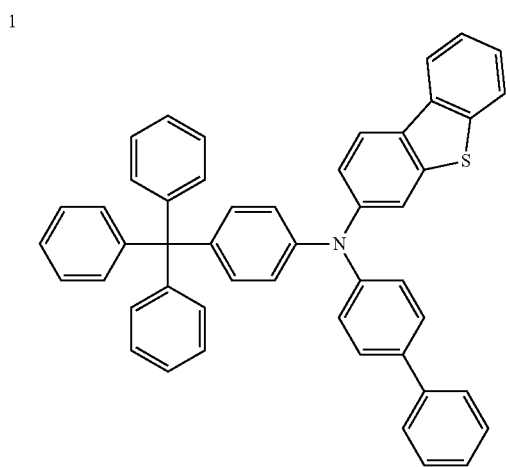
3
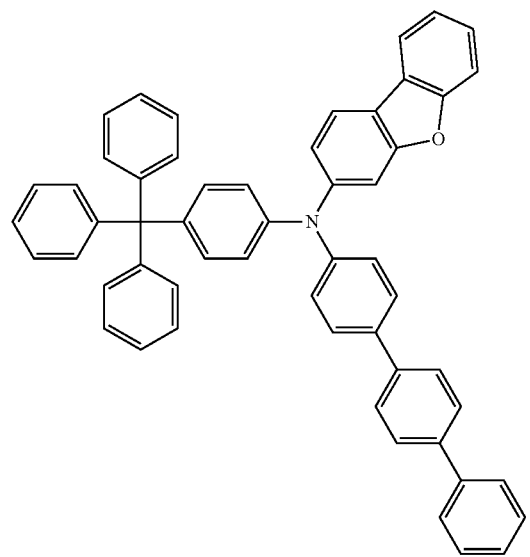
4
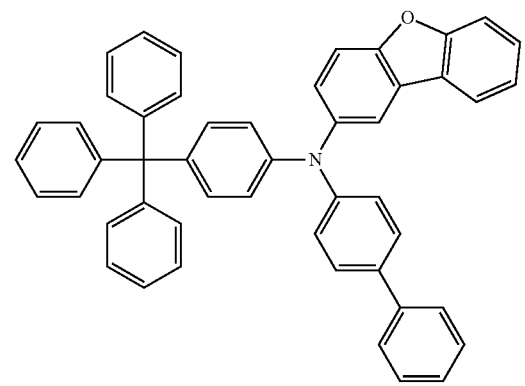
5
6
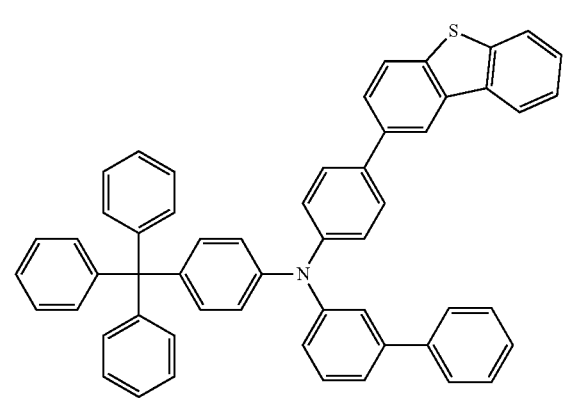

-continued
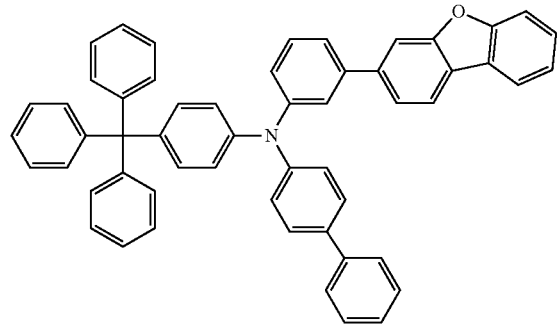
7
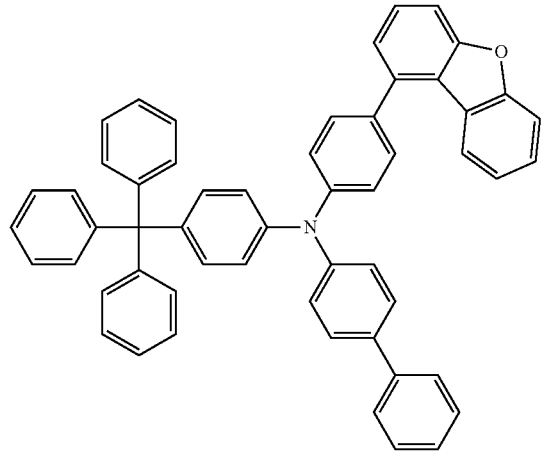
8
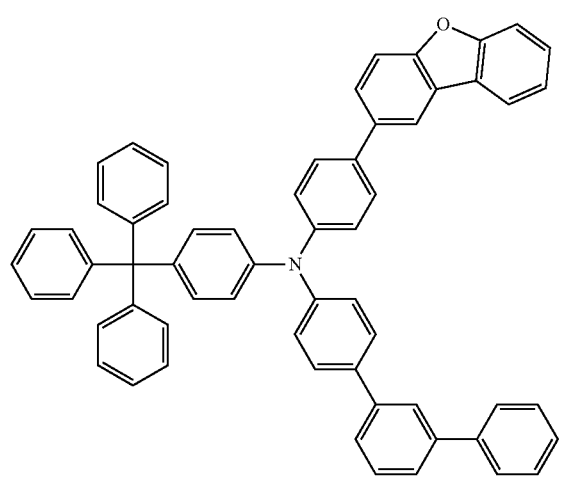
9
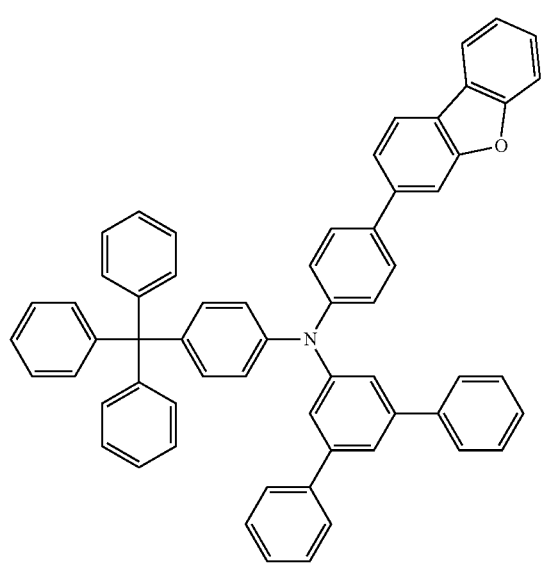
10
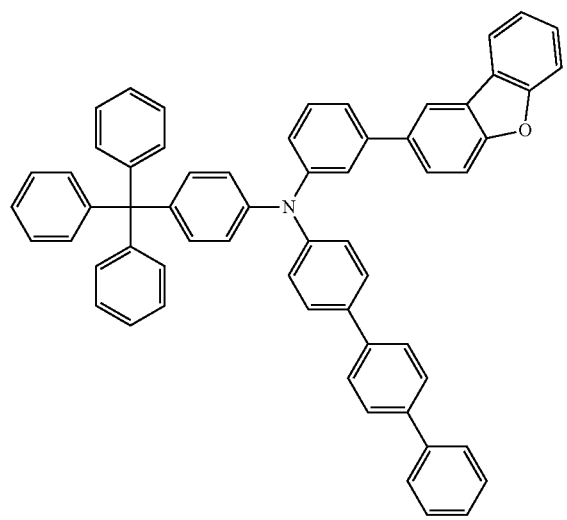
11
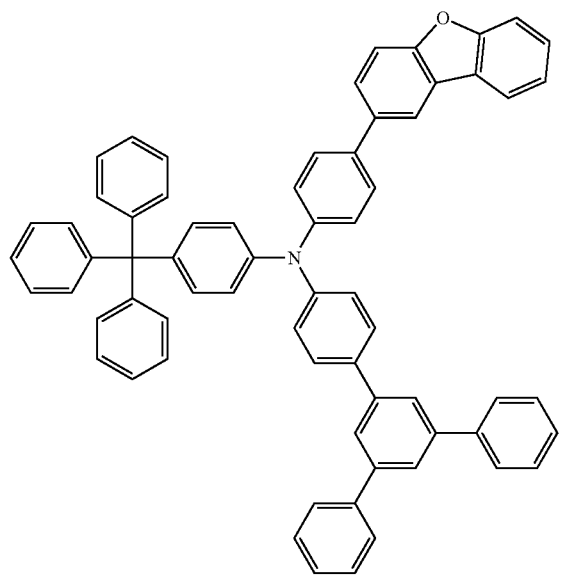
12

-continued
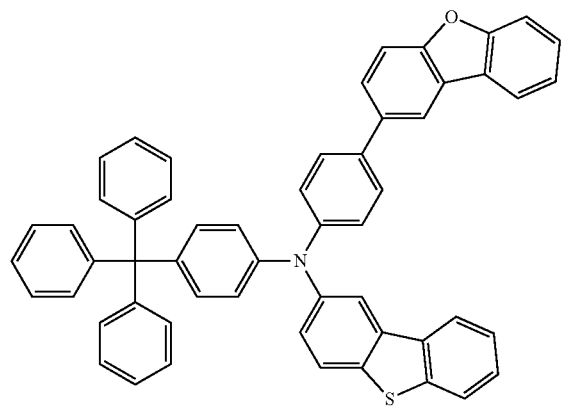
13
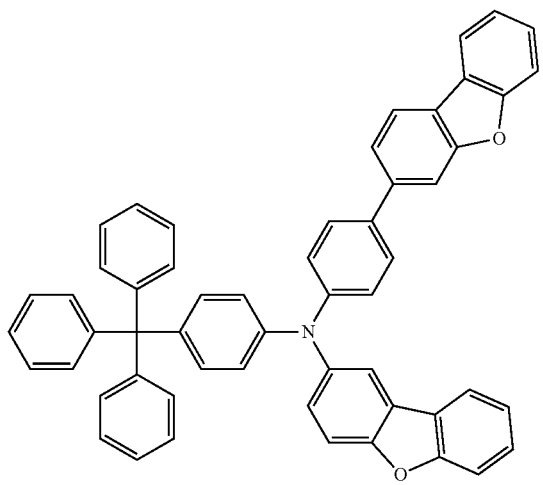
14
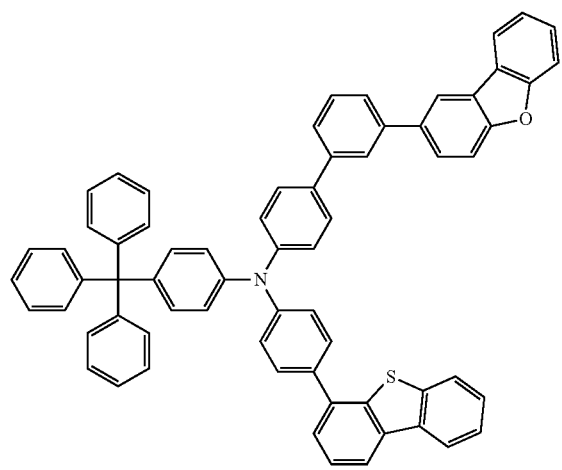
15
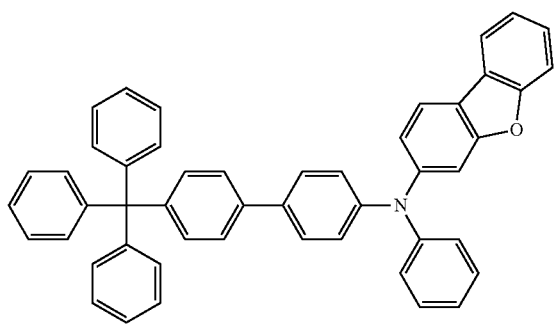
17
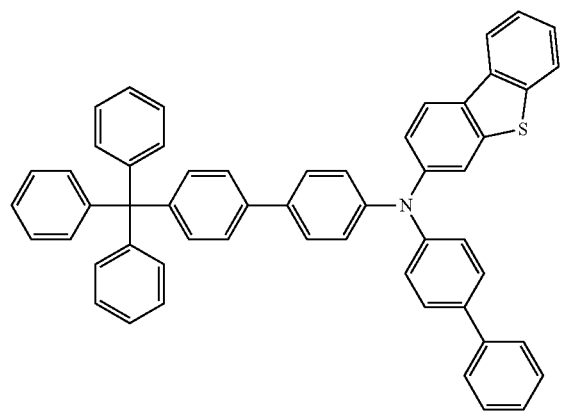
18
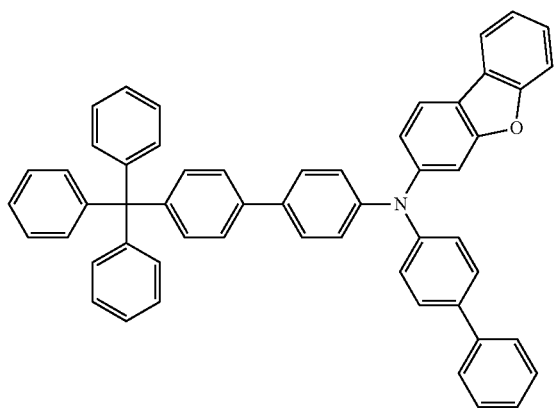
19

-continued
20
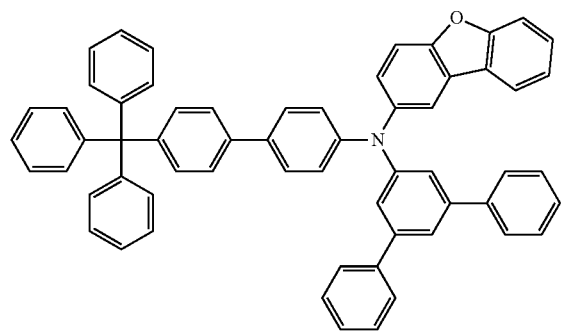
21
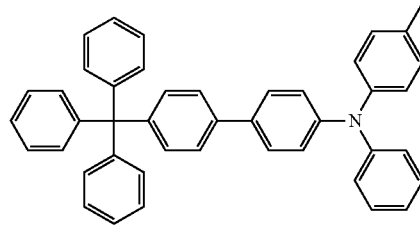
22
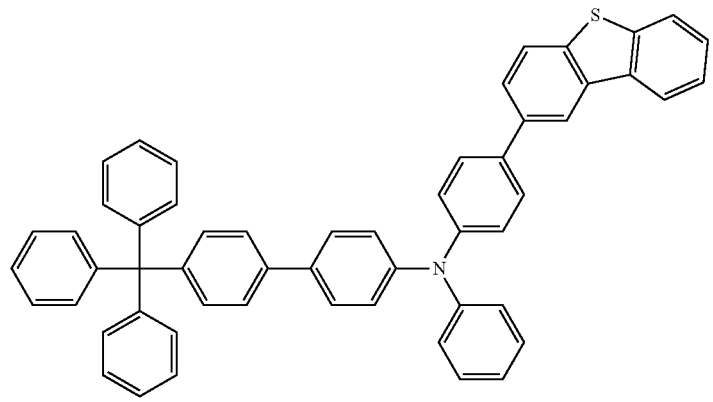
23
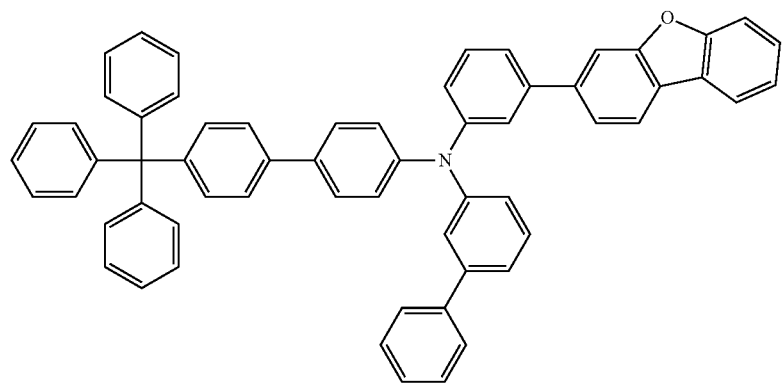
24
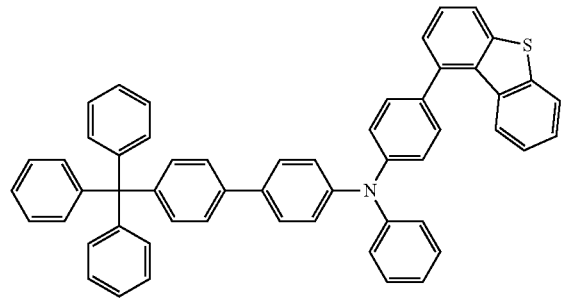
25
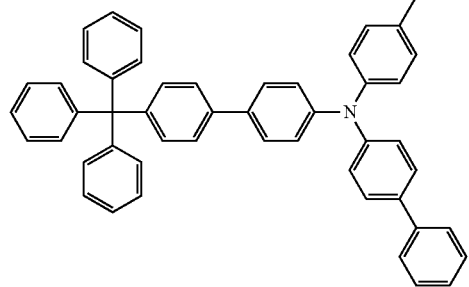

-continued
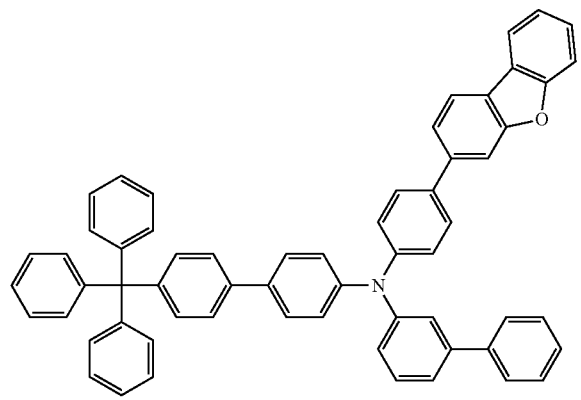
26
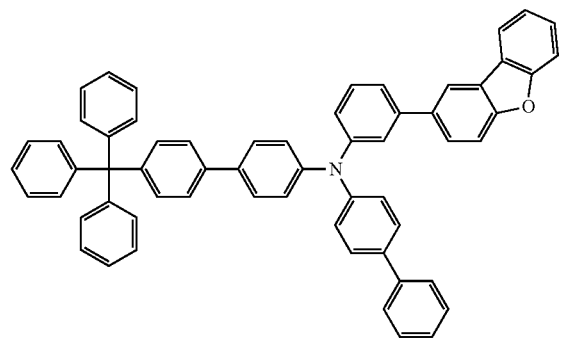
27
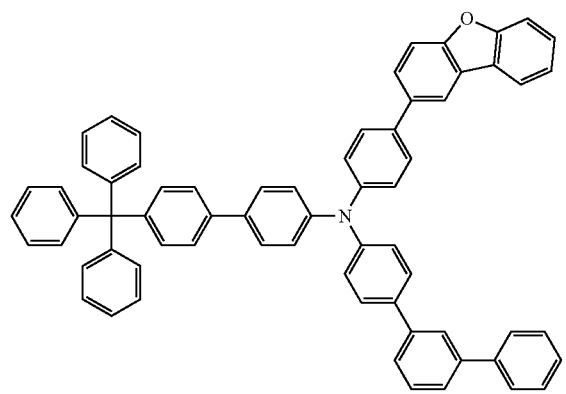
28
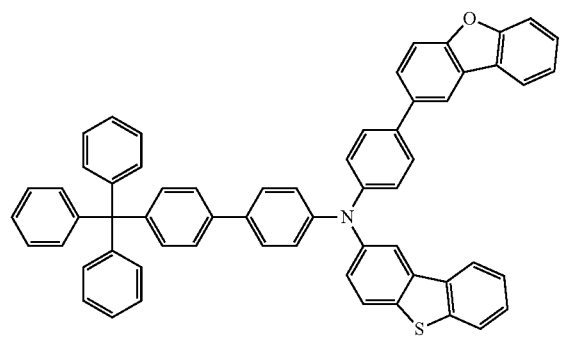
29
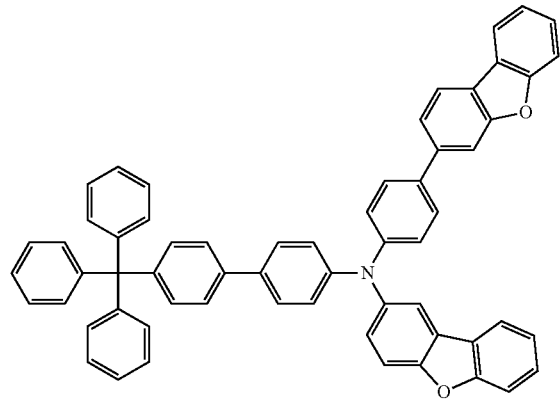
30
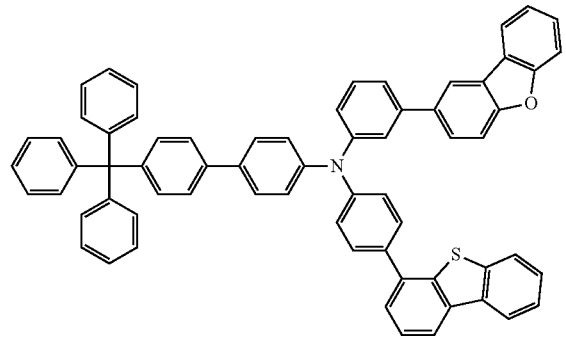
31

-continued
32
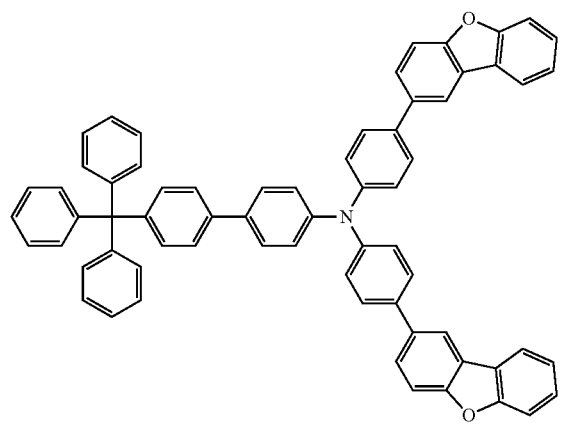
33
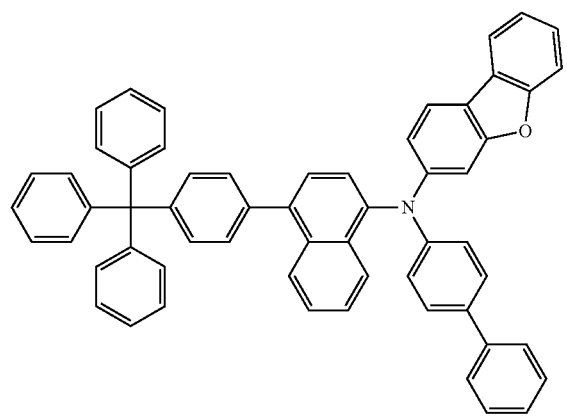
34
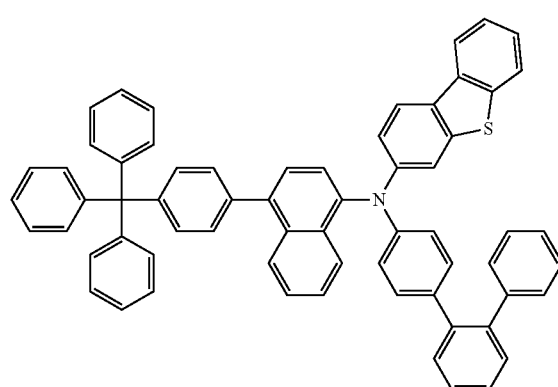
35
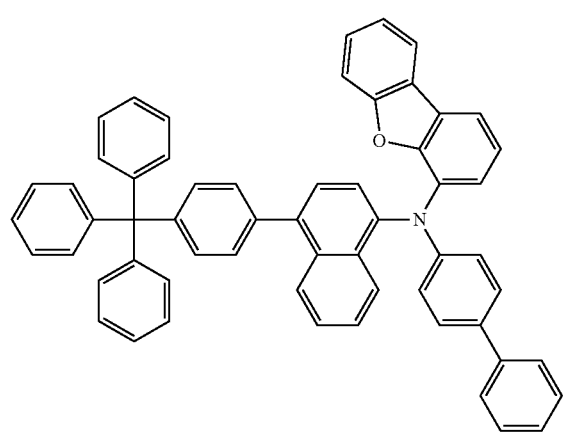
36
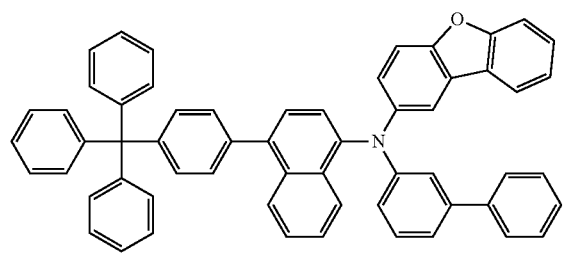
37
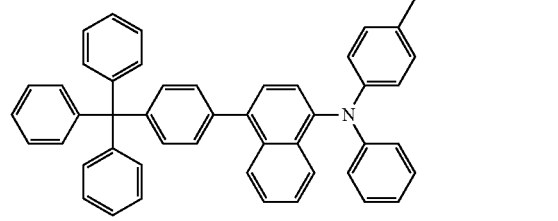
38
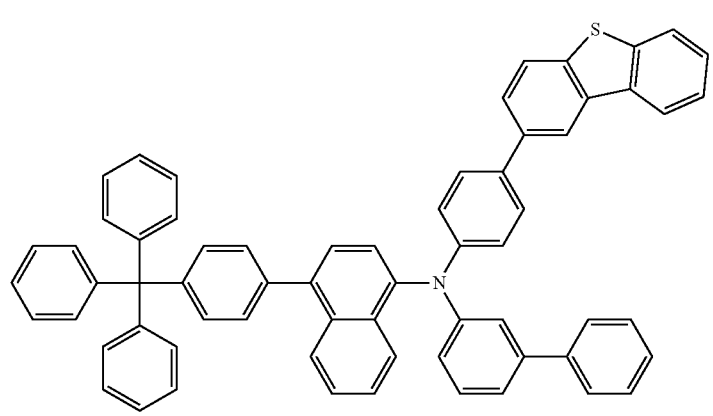

39
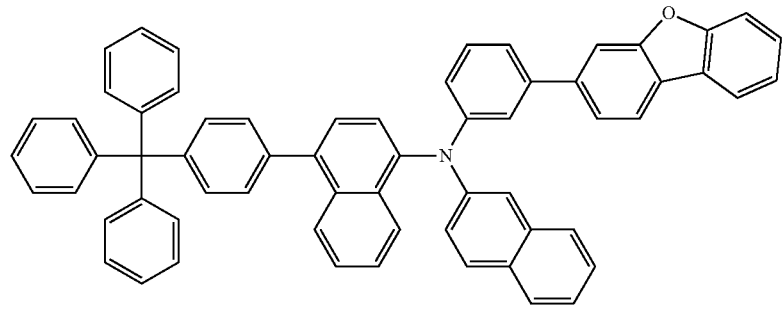
40
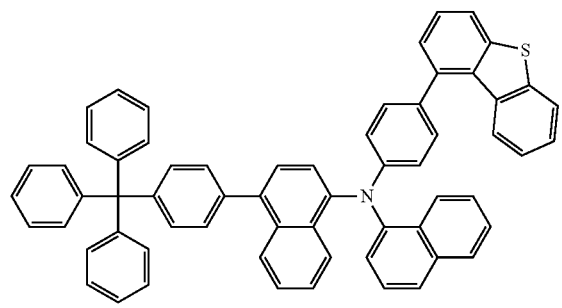
41
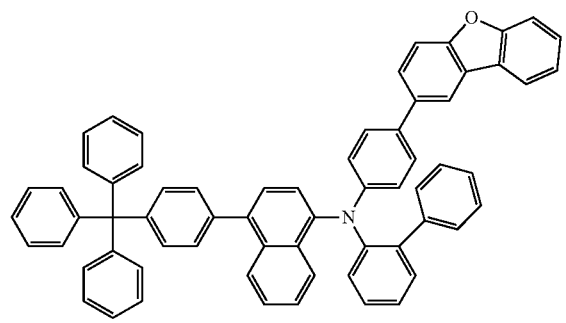
42
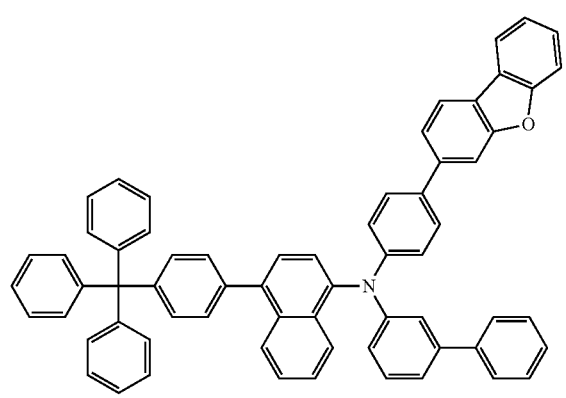
43
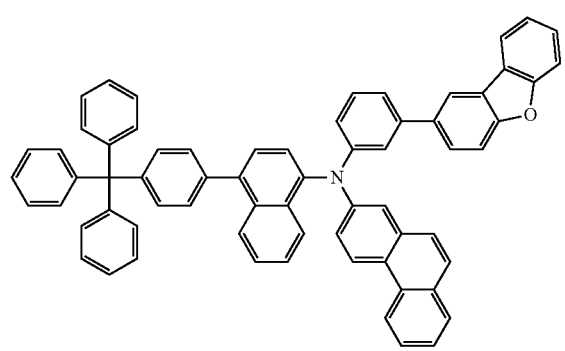
44
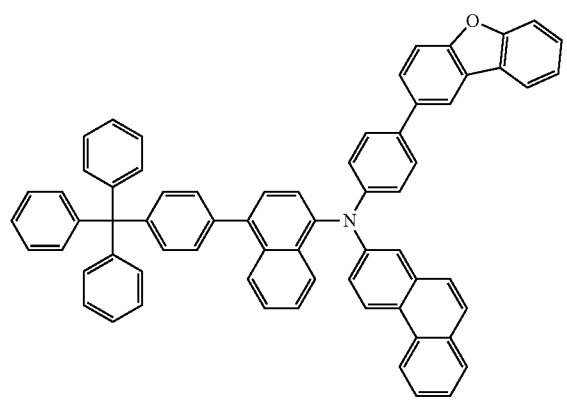
45
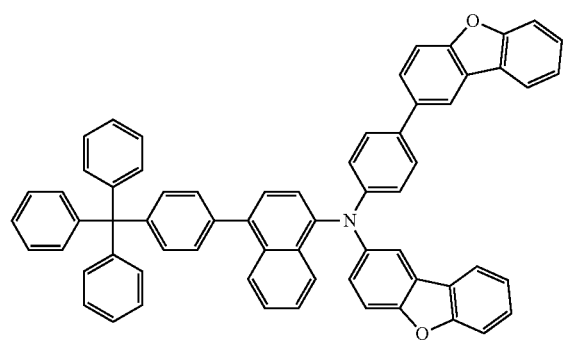

-continued
46
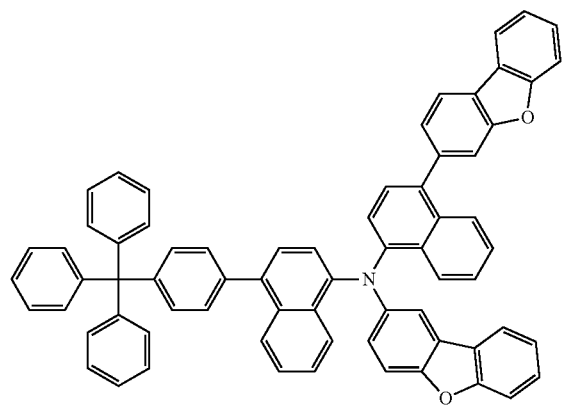
47
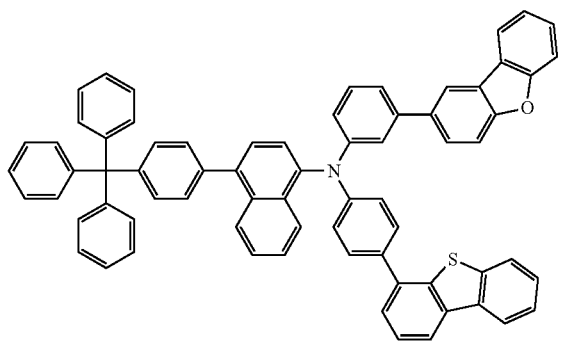
48
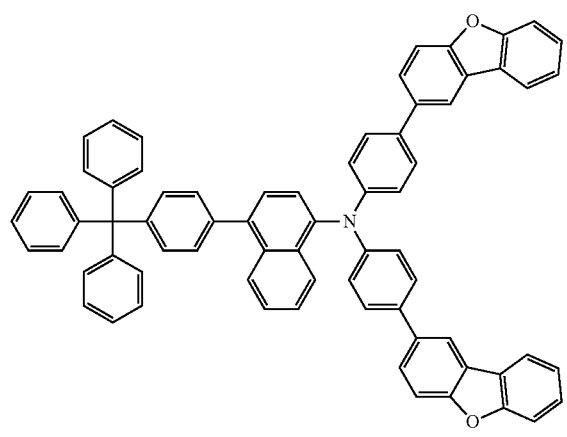
49
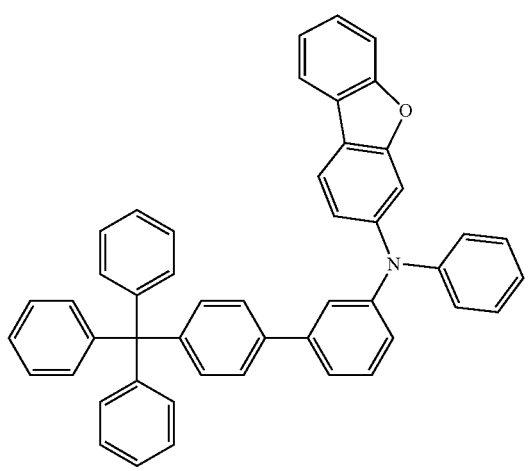
50
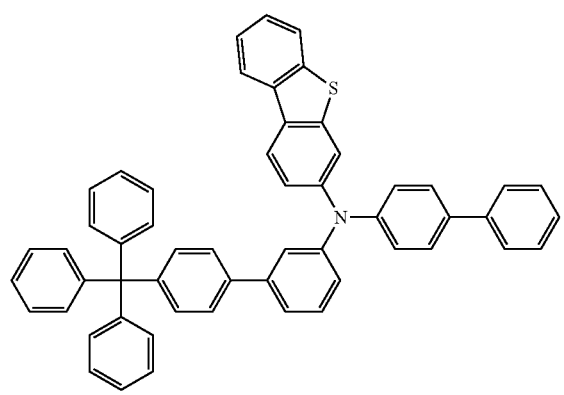
51
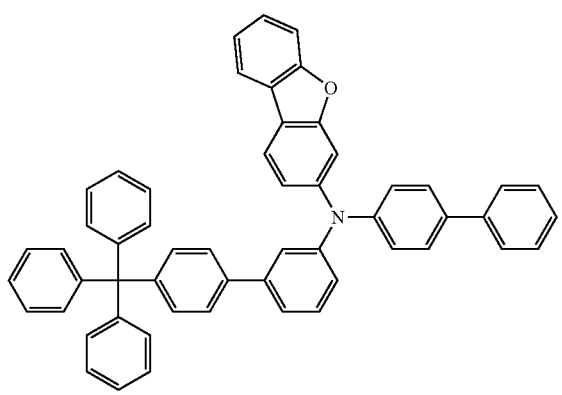

-continued
52
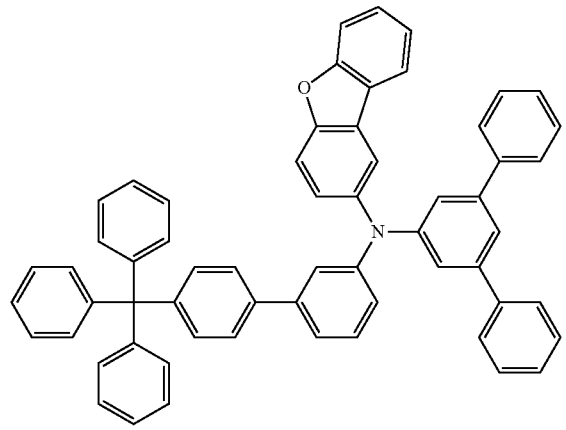
53
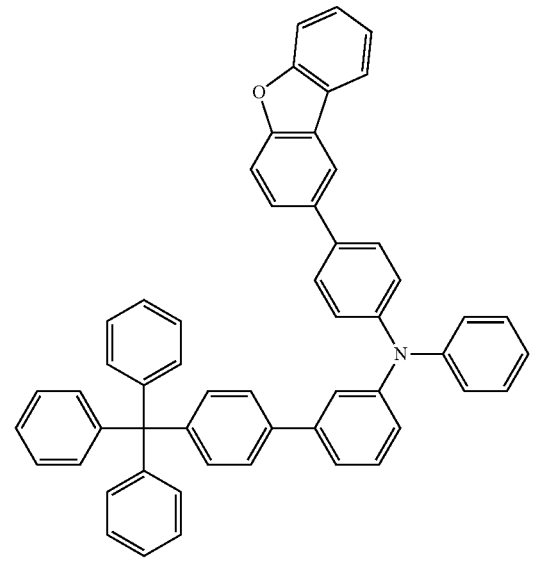
54
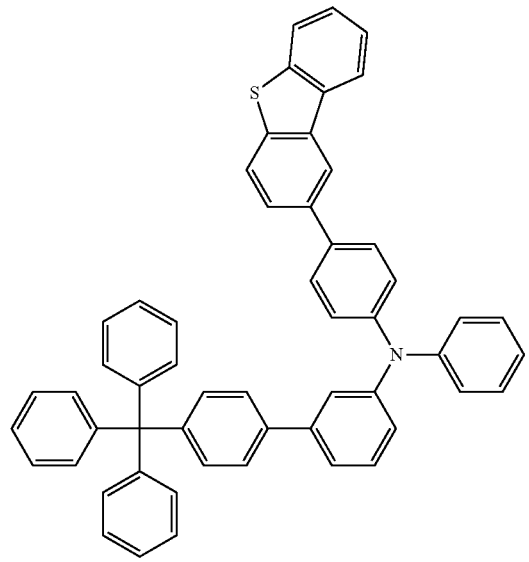
55
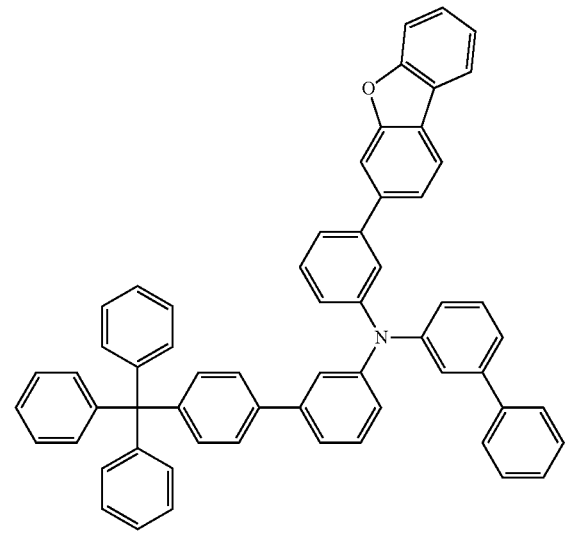
56
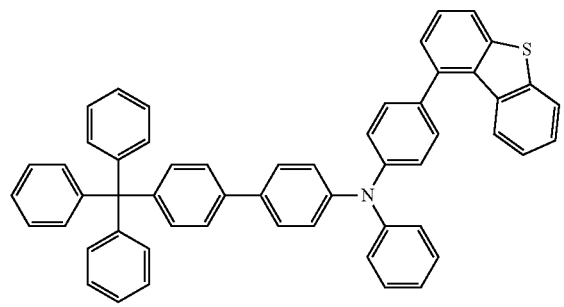
57
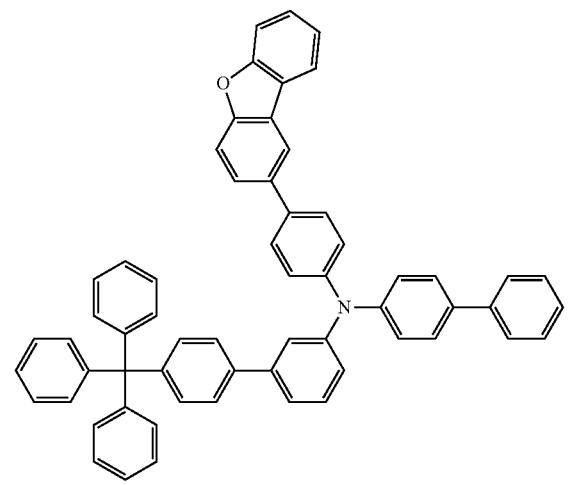

58
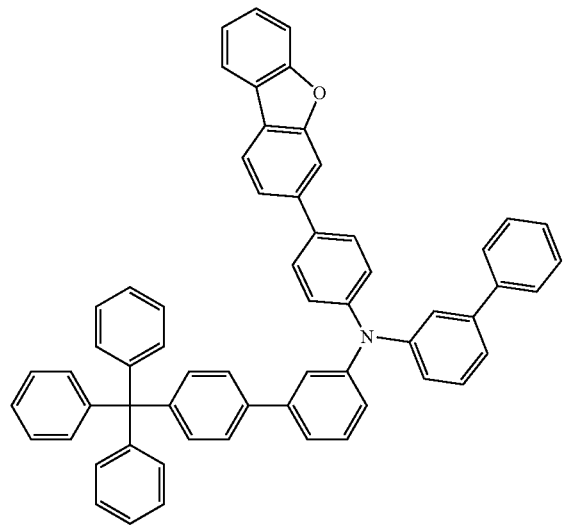
59
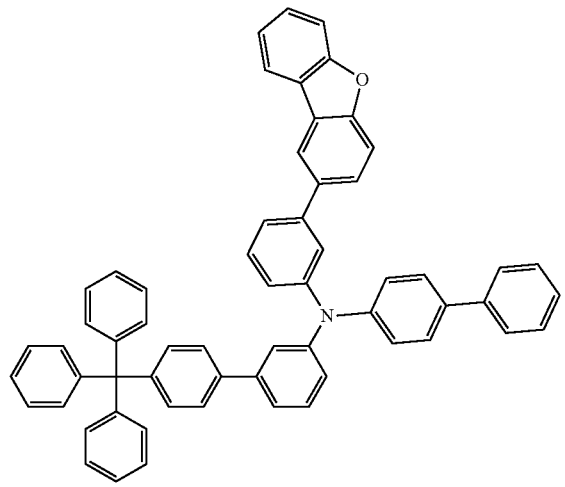
60
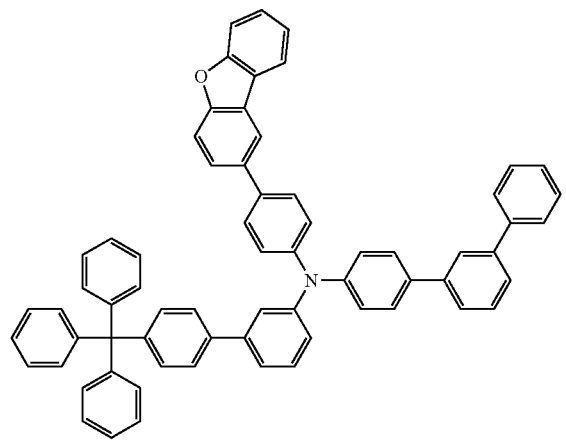
61
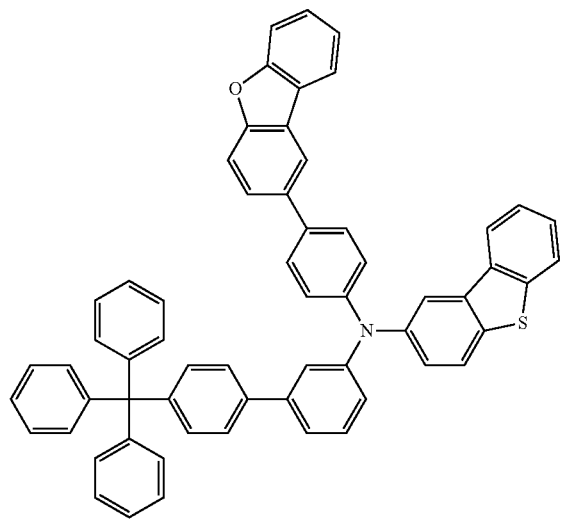
62
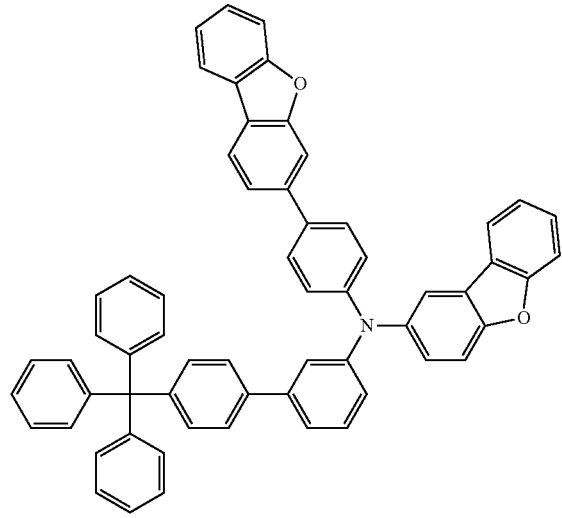
63
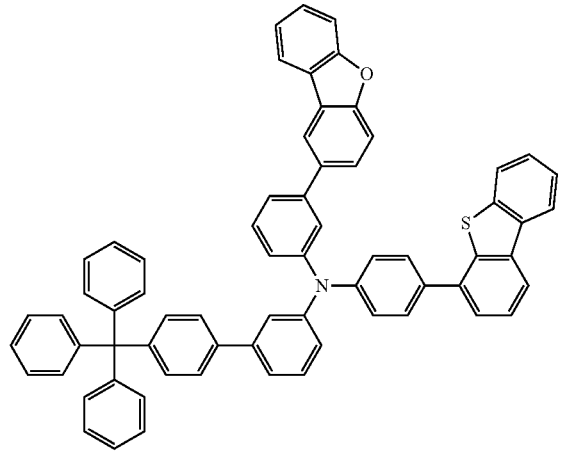

-continued

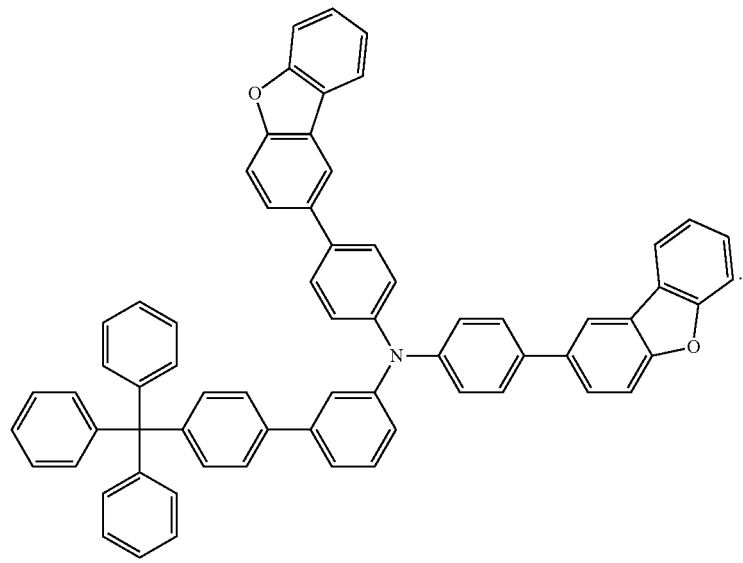

64

31. The light emitting diode of claim 30, wherein the hole transfer layer comprises a hole injection layer and a hole transport layer disposed between the hole injection layer and the emitting material layer, and wherein the hole transport layer comprises the organic compound.

32. The light emitting diode of claim 31, wherein the hole transport layer comprises a host and a dopant, and wherein the host comprises the organic compound.

33. The light emitting diode of claim 31, wherein the hole transport layer comprises a first hole transport layer disposed between the hole injection layer and the emitting material layer and a second hole transport layer disposed between the first hole transport layer and the emitting material layer, and wherein the second hole transport layer comprises the organic compound.

* * * * *